US012606540B2

(12) United States Patent
Chen et al.

(10) Patent No.: US 12,606,540 B2
(45) Date of Patent: Apr. 21, 2026

(54) TRIAZOLONE COMPOUND

(71) Applicant: MEDSHINE DISCOVERY INC., Jiangsu (CN)

(72) Inventors: Shuhui Chen, Shanghai (CN); Zhengxia Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 603 days.

(21) Appl. No.: 17/999,557

(22) PCT Filed: May 24, 2021

(86) PCT No.: PCT/CN2021/095599

§ 371 (c)(1),
(2) Date: Jan. 18, 2023

(87) PCT Pub. No.: WO2021/238881

PCT Pub. Date: Dec. 2, 2021

(65) Prior Publication Data

US 2023/0257362 A1 Aug. 17, 2023

(30) Foreign Application Priority Data

May 29, 2020 (CN) ......................... 202010478375.4
Jul. 24, 2020 (CN) ......................... 202010721277.9
Sep. 8, 2020 (CN) ......................... 202010937150.0
Dec. 7, 2020 (CN) ......................... 202011437576.6
Apr. 2, 2021 (CN) ......................... 202110361719.8

(51) Int. Cl.

| | |
|---|---|
| ***C07D 401/10*** | (2006.01) |
| ***A61P 31/16*** | (2006.01) |
| ***C07D 249/12*** | (2006.01) |
| ***C07D 401/04*** | (2006.01) |
| ***C07D 401/14*** | (2006.01) |
| ***C07D 403/04*** | (2006.01) |

(52) U.S. Cl.

CPC ............ *C07D 401/10* (2013.01); *A61P 31/16* (2018.01); *C07D 249/12* (2013.01); *C07D 401/04* (2013.01); *C07D 401/14* (2013.01); *C07D 403/04* (2013.01)

(58) Field of Classification Search

None
See application file for complete search history.

(56) References Cited

U.S. PATENT DOCUMENTS

2020/0123129 A1 4/2020 Gradl et al.

FOREIGN PATENT DOCUMENTS

| | | | | |
|---|---|---|---|---|
| CN | 107459491 A | 12/2017 | | |
| CN | 109336829 A | 2/2019 | | |
| CN | 110023302 A | 7/2019 | | |
| WO | 2006022442 A1 | 3/2006 | | |
| WO | 2018077944 A2 | 5/2018 | | |
| WO | WO 2018/077923 A1 * | 5/2018 | .......... | C07D 403/12 |

OTHER PUBLICATIONS

Oct. 20, 2021 International Search Report issued in International Patent Application No. PCT/CN2021/095599.
Oct. 8, 2021 Written Opinion of the International Searching Authority issued in International Patent Application No. PCT/CN2021/095599.
Sep. 20, 2023 First Chinese Office Action issued in Chinese application No. 202180036397.8.
Sep. 16, 2023 Chinese Search Report issued in Chinese application No. 202180036397.8.
Dec. 22, 2023 First Japanese Office Action issued in Japanese application No. 2022-573319.
Medicinal Chemistry, Jan. 31, 2016, Meng Fansen et al, p. 385-387.
Jun. 11, 2024 Extended European Search Report issued in Eurasian Patent Application No. 21813193.6.
May 21, 2024 Japanese Office Action issued in Japanese Patent Application No. 2022-573319.
Oct. 22, 2024 Japanese Office Action issued in Japanese Patent Application No. 2022-573319.
Kittaka, Atsushi, Pharmaceutical science Pharmaceutical Chemistry, 2007, p. 142-150.
Satoshi Shuto, Molecular theory of organic drugs, 2012, p. 201-218.
Sun S, Jia Q, Zhang Z. Applications of amide isosteres in medicinal chemistry. Bioorg Med Chem Lett. Sep. 15, 2019;29(18):2535-2550.

* cited by examiner

*Primary Examiner* — Brian J Davis
(74) *Attorney, Agent, or Firm* — Houston Beshining Law Office PLLC; Liangang Ye

(57) ABSTRACT

The present invention discloses a series of triazolone compounds, and specifically discloses a compound and a pharmaceutically acceptable salt thereof as shown in formula (V).

(V)

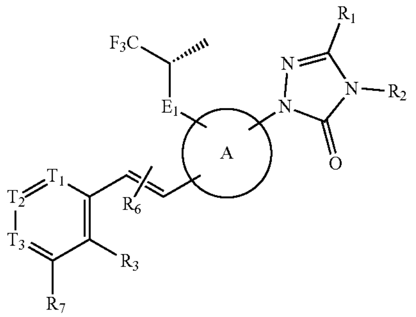

11 Claims, 12 Drawing Sheets

TRIAZOLONE COMPOUND

The present application is a National Stage of International Application No. PCT/CN2021/095599, filed on May 24, 2021, which claims priorities of the Chinese Patent Application No. CN202010478375.4 filed on May 29, 2020, the Chinese Patent Application No. CN202010721277.9 filed on Jul. 24, 2020, the Chinese Patent Application No. CN202010937150.0 filed on Sep. 8, 2020, the Chinese Patent Application No. CN202011437576.6 filed on Dec. 7, 2020, and the Chinese Patent Application No. CN202110361719.8 filed on Apr. 2, 2021, the contents of which are incorporated herein by reference in their entireties.

TECHNICAL FIELD

The present disclosure relates to a series of triazolone compounds, and specifically relates to a compound represented by formula (V) and a pharmaceutically acceptable salt thereof.

BACKGROUND

Dihydroorotate dehydrogenase (DHODH), a kind of iron-containing flavin dependent enzyme, exists in the inner membrane of human mitochondria. It catalyzes the fourth step in the de novo synthesis pathway of pyrimidine nucleotides in nucleic acids in vivo, and is the rate-limiting enzyme for pyrimidine nucleotides synthesis. Pyrimidine nucleotides are necessary for the synthesis of DNA, RNA, glycoproteins and phospholipids in organism; therefore, the synthesis of pyrimidine nucleotides is crucial for cell proliferation and metabolism. When a cell is infected by a virus, the virus needs to rely heavily on nucleosides in the host cell to replicate, therefore, blocking the DHODH pyrimidine synthesis pathway of the host can effectively inhibit virus replication, which not only has broad spectrum antiviral activity, but also can avoid drug-resistant mutations caused by specific targeting of viral proteins. In tumor cells, the demand for pyrimidine nucleotides is far greater than that of normal cells, and the synthesis of pyrimidine nucleotides mainly depends on the de novo synthesis pathway, therefore, inhibition of DHODH can block the synthesis of new pyrimidine nucleotides, resulting in obstacles in the biosynthesis of DNA (including thymine and cytosine), RNA (including uracil and cytosine), glycoproteins and phospholipids, thereby causing cell cycle arrest and inhibiting abnormal cell proliferation. Studies have shown that DHODH is highly expressed in a variety of tumors and is positively related to the poor prognosis of clinical tumor patients, inhibiting the expression of DHODH can inhibit tumor proliferation. In addition, activated lymphocytes also need a lot of nucleic acids for proliferation and metabolism, and are sensitive to the inhibition of DHODH activity, therefore, inhibition of DHODH activity can effectively inhibit the proliferation of activated lymphocytes and the secretion of cytokines, while DHODH inhibitors such as leflunomide and teriflunomide are also effective drugs for treating autoimmune diseases, such as rheumatoid arthritis. To sum up, DHODH has not only become a potential target for anti-tumor therapy, but also an effective target for broad-spectrum anti-virus infection and treatment of autoimmune diseases, it is of great significance to develop and research specific inhibitors against DHODH.

CONTENT OF THE PRESENT INVENTION

The present disclosure provides a compound represented by formula (V) or a pharmaceutically acceptable salt thereof, (V)

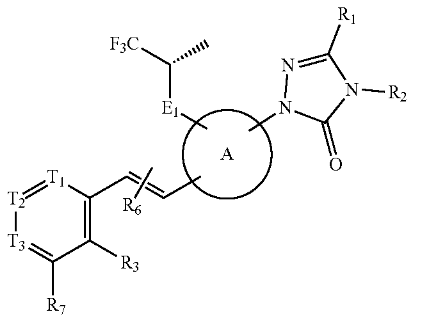

wherein, ring A is selected from phenyl, pyridinyl, pyrrolyl, pyrazolyl, imidazolyl and 1,2,4-triazolyl, and the phenyl, pyridinyl, pyrrolyl, pyrazolyl and imidazolyl are optionally substituted by 1, 2 or 3 $R_a$;

$E_1$ is selected from $CH_2$ and O;

$T_1$ is selected from $CR_4$ and N;

$T_2$ is selected from CH and N;

$T_3$ is selected from $CR_5$ and N;

$R_1$ is selected from $CH_2OH$, COOH and $CONH_2$;

$R_2$ is selected from $C_{1-3}$ alkyl, and the $C_{1-3}$ alkyl is optionally substituted by 1, 2 or 3 $R_b$;

$R_3$ and $R_4$ are each independently selected from H, F, Cl, CN, $CH_3$ and $OCH_3$, and the $CH_3$ and $OCH_3$ are optionally substituted by 1, 2 or 3 $R_c$;

$R_5$ is selected from H, F, Cl and CN;

$R_6$ is selected from H and F;

$R_7$ is selected from H and

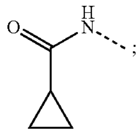

;

each $R_a$ is independently selected from F and Cl;

each $R_b$ is independently selected from F, Cl and Br;

each $R_c$ is independently selected from F, Cl and Br.

In some embodiments of the present disclosure, the $R_2$ is selected from $CH_3$, $CH_2CH_3$, $CH_2CH_2CH_3$ and $CH(CH_3)_2$, and the $CH_3$, $CH_2CH_3$, $CH_2CH_2CH_3$ and $CH(CH_3)_2$ are optionally substituted by 1, 2 or 3 $R_b$, and other variables are as defined in the present disclosure.

In some embodiments of the present disclosure, the $R_2$ is selected from $CH_3$ and $CH_2CH_3$, and other variables are as defined in the present disclosure.

In some embodiments of the present disclosure, the ring A is selected from

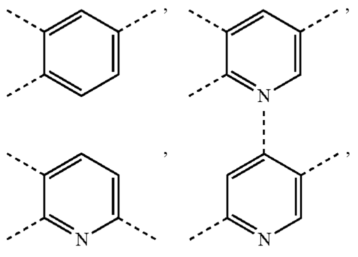

-continued

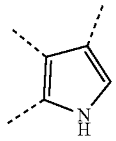
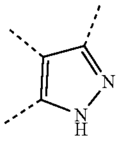
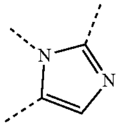
and
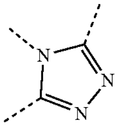

and the

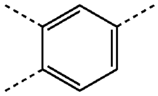
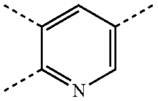
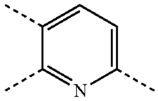
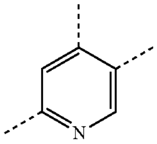
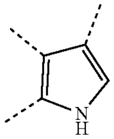
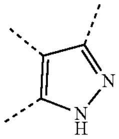
and
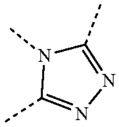

are optionally substituted by 1, 2 or 3 $R_a$, and other variables are as defined in the present disclosure.

In some embodiments of the present disclosure, the ring A is selected from

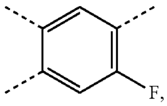
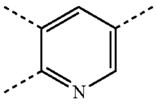
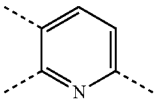
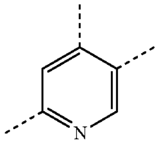
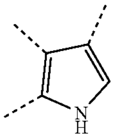
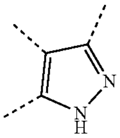
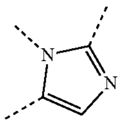
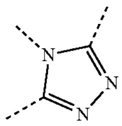
and
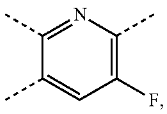

and other variables are as defined in the present disclosure.

In some embodiments of the present disclosure, the structural moiety

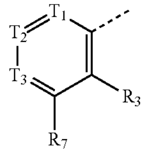

is selected from

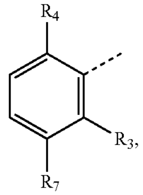
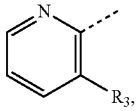
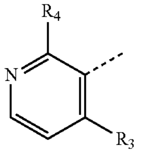
and
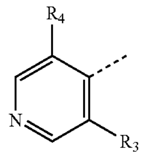
and
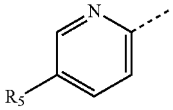

and other variables are as defined in the present disclosure.

In some embodiments of the present disclosure, the structural moiety

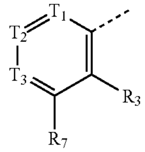

is selected from

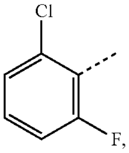
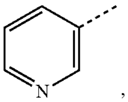
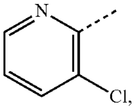
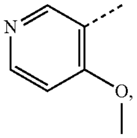
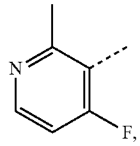
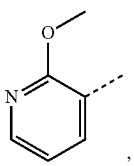
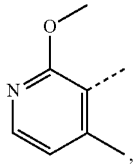
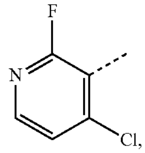
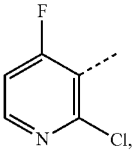
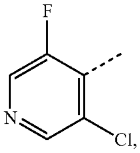
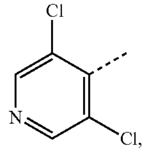
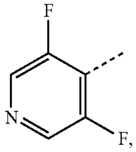
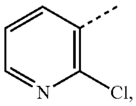

-continued

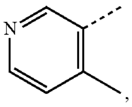,
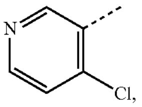
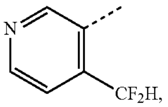

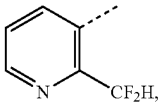
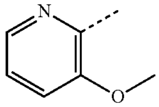,
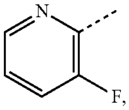

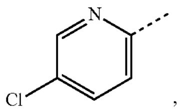,
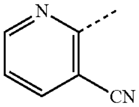 and

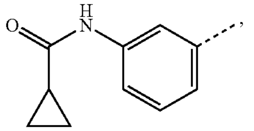

and other variables are as defined in the present disclosure.

In some embodiments of the present disclosure, the structural moiety

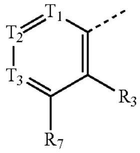

is selected from

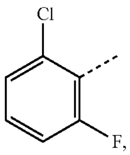
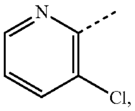
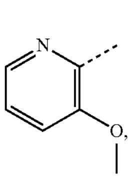
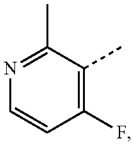
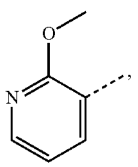
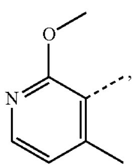
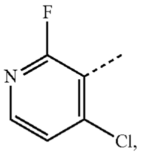
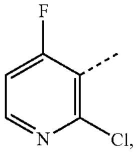
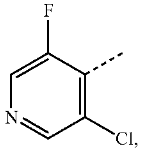
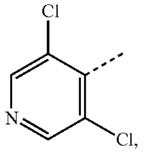

-continued

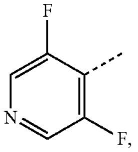
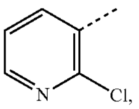
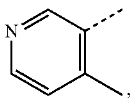,

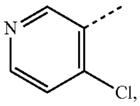
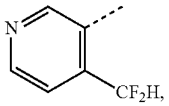
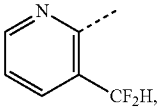

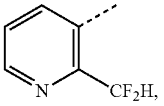
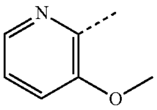,
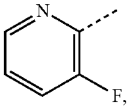

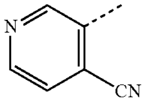 and
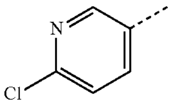,

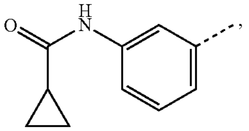

and other variables are as defined in the present disclosure.

The present disclosure provides a compound represented by formula (IV) or a pharmaceutically acceptable salt thereof, (IV)

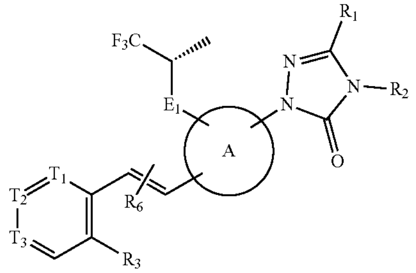

wherein, ring A is selected from phenyl, pyridinyl, pyrrolyl, pyrazolyl, imidazolyl and 1,2,4-triazolyl, and the phenyl, pyridinyl, pyrrolyl, pyrazolyl and imidazolyl are optionally substituted by 1, 2 or 3 $R_a$;

$E_1$ is selected from $CH_2$ and O;

$T_1$ is selected from $CR_4$ and N;

$T_2$ is selected from CH and N;

$T_3$ is selected from $CR_5$ and N;

$R_1$ is selected from $CH_2OH$, COOH and $CONH_2$;

$R_2$ is selected from $C_{1-3}$ alkyl, and the $C_{1-3}$ alkyl is optionally substituted by 1, 2 or 3 $R_b$;

$R_3$ and $R_4$ are each independently selected from H, F, Cl, CN, $CH_3$ and $OCH_3$, and the $CH_3$ and $OCH_3$ are optionally substituted by 1, 2 or 3 $R_c$;

$R_5$ is selected from H, F, Cl and CN;

$R_6$ is selected from H and F;

each $R_a$ is independently selected from F and Cl;

each $R_b$ is independently selected from F, Cl and Br;

each $R_c$ is independently selected from F, Cl and Br.

In some embodiments of the present disclosure, the $R_2$ is selected from $CH_3$, $CH_2CH_3$, $CH_2CH_2CH_3$ and $CH(CH_3)_2$, and the $CH_3$, $CH_2CH_3$, $CH_2CH_2CH_3$ and $CH(CH_3)_2$ are optionally substituted by 1, 2 or 3 $R_b$, and other variables are as defined in the present disclosure.

In some embodiments of the present disclosure, the $R_2$ is selected from $CH_3$ and $CH_2CH_3$, and other variables are as defined in the present disclosure.

In some embodiments of the present disclosure, the ring A is selected from

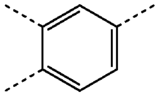,
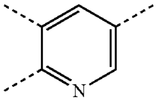,
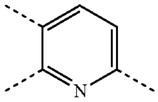,
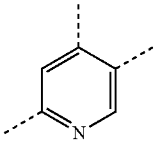,
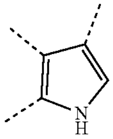,
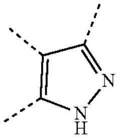,
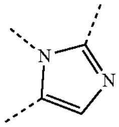
and
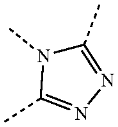, and the

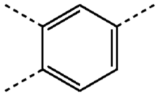,
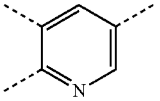,
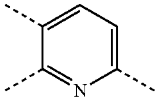,
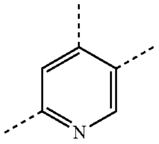,
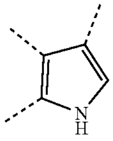,
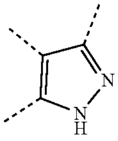
and
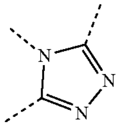

are optionally substituted by 1, 2 or 3 $R_a$, and other variables are as defined in the present disclosure.

In some embodiments of the present disclosure, the ring A is selected from

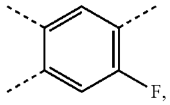
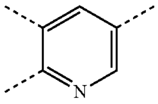,
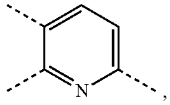,
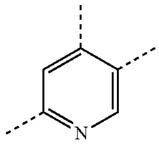,
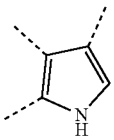,
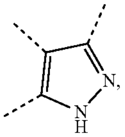
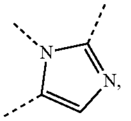
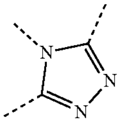
and
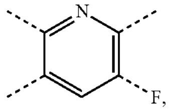

and other variables are as defined in the present disclosure.

In some embodiments of the present disclosure, the structural moiety

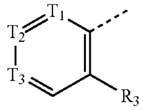

is selected from

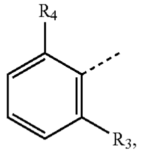
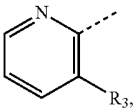
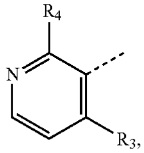
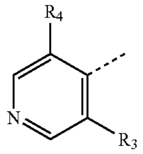
and
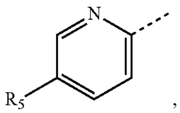, and other variables are as defined in the present disclosure.

In some embodiments of the present disclosure, the structural moiety

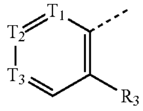

is selected from

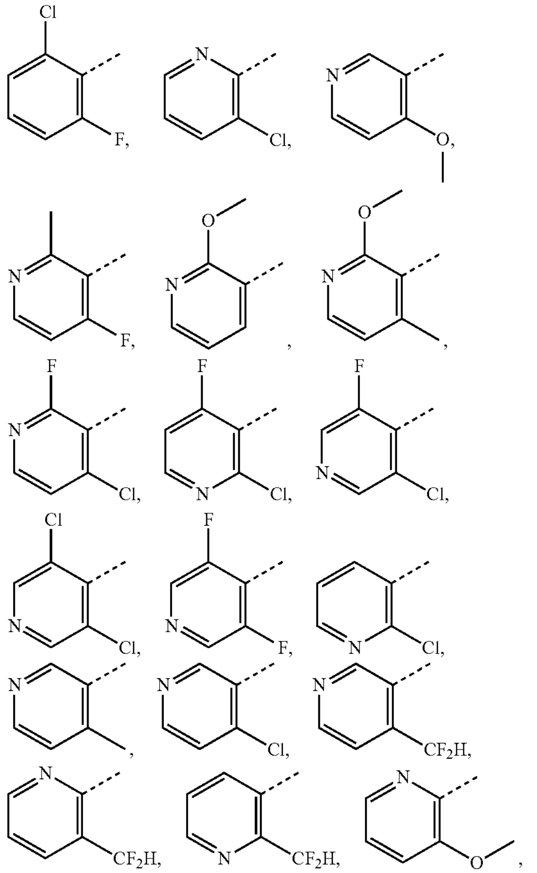

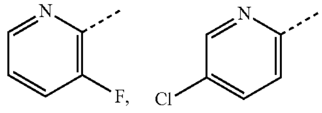

and

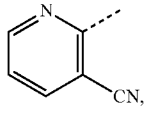

and other variables are as defined in the present disclosure.

The present disclosure provides a compound represented by formula (I) or a pharmaceutically acceptable salt thereof, (I)

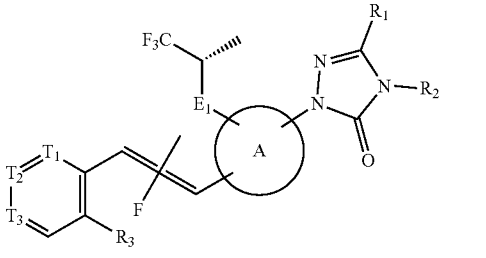

wherein, ring A is selected from phenyl, pyridinyl, pyrrolyl, pyrazolyl, imidazolyl and 1,2,4-triazolyl, and the phenyl, pyridinyl, pyrrolyl, pyrazolyl and imidazolyl are optionally substituted by 1, 2 or 3 $R_a$;

$E_1$ is selected from $CH_2$ and O;

$T_1$ is selected from $CR_4$ and N;

$T_2$ and $T_3$ are each independently selected from CH and N;

$R_1$ is selected from $CH_2OH$, COOH and $CONH_2$;

$R_2$ is selected from $C_{1-3}$ alkyl, and the $C_{1-3}$ alkyl is optionally substituted by 1, 2 or 3 $R_b$;

$R_3$ and $R_4$ are each independently selected from H, F, Cl, $CH_3$ and $OCH_3$;

each $R_a$ is independently selected from F and Cl;

each $R_b$ is independently selected from F, Cl and Br.

In some embodiments of the present disclosure, the $R_2$ is selected from $CH_3$, $CH_2CH_3$, $CH_2CH_2CH_3$ and $CH(CH_3)_2$, and the $CH_3$, $CH_2CH_3$, $CH_2CH_2CH_3$ and $CH(CH_3)_2$ are optionally substituted by 1, 2 or 3 $R_b$, and other variables are as defined in the present disclosure.

In some embodiments of the present disclosure, the $R_2$ is selected from $CH_3$ and $CH_2CH_3$, and other variables are as defined in the present disclosure.

In some embodiments of the present disclosure, the ring A is selected from

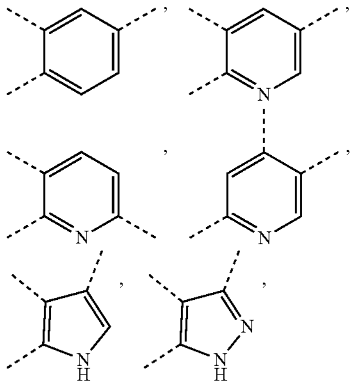

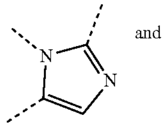

and

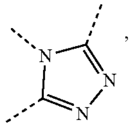

and the

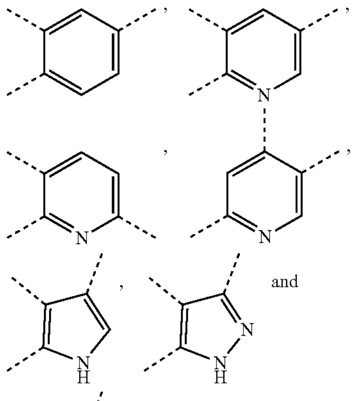

and

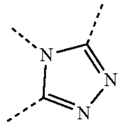

are optionally substituted by 1, 2 or 3 $R_a$, and other variables are as defined in the present disclosure.

In some embodiments of the present disclosure, the ring A is selected from

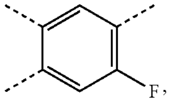 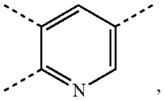 , 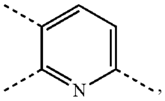 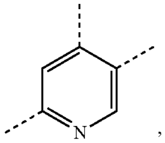 , 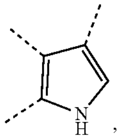 , 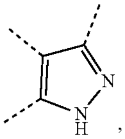 , 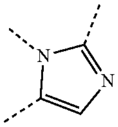 and 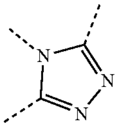 , and other variables are as defined in the present disclosure.

In some embodiments of the present disclosure, the structural moiety

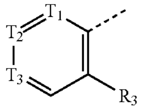

is selected from

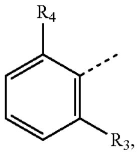 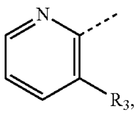 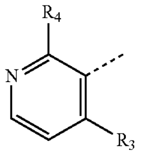 and 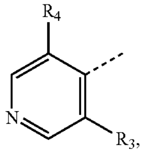

and other variables are as defined in the present disclosure.

In some embodiments of the present disclosure, the structural moiety

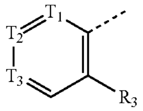

is selected from

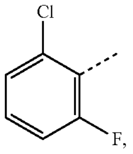 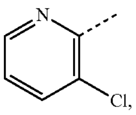 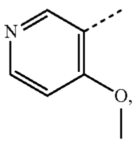

-continued

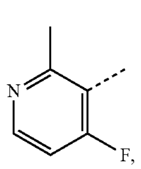 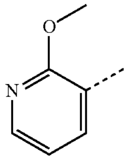 , 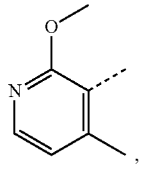 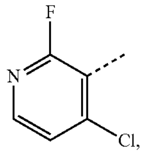 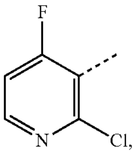 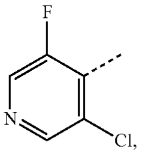 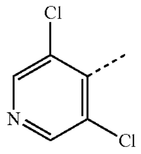 and 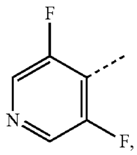

and other variables are as defined in the present disclosure.

In some embodiments of the present disclosure, the structural moiety

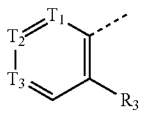

is selected from

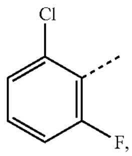 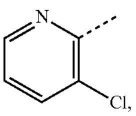 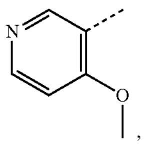 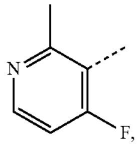 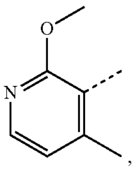 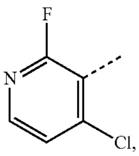 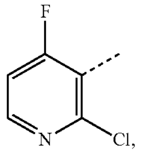 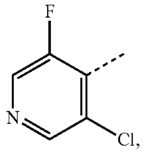 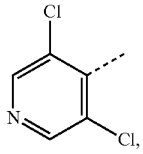 and 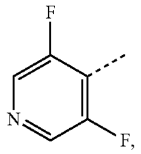

and other variables are as defined in the present disclosure.

The present disclosure provides a compound represented by formula (I) or a pharmaceutically acceptable salt thereof, (I)

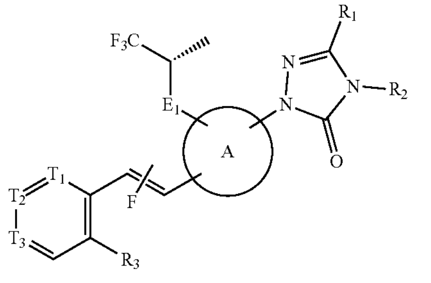

wherein, ring A is selected from phenyl, pyridinyl, pyrrolyl, pyrazolyl, imidazolyl and 1,2,4-triazolyl, and the phenyl, pyridinyl, pyrrolyl, pyrazolyl and imidazolyl are optionally substituted by 1, 2 or 3 $R_a$;

$E_1$ is selected from $CH_2$ and O;

$T_1$ is selected from $CR_4$ and N;

$T_2$ and $T_3$ are each independently selected from CH and N;

$R_1$ is selected from $CH_2OH$, COOH and $CONH_2$;

$R_2$ is selected from $C_{1-3}$ alkyl, and the $C_{1-3}$ alkyl is optionally substituted by 1, 2 or 3 $R_b$;

$R_3$ and $R_4$ are each independently selected from F, Cl, $CH_3$ and $OCH_3$;

each $R_a$ is independently selected from F and Cl;

each $R_b$ is independently selected from F, Cl and Br.

In some embodiments of the present disclosure, the $R_2$ is selected from $CH_3$, $CH_2CH_3$, $CH_2CH_2CH_3$ and $CH(CH_3)_2$, and the $CH_3$, $CH_2CH_3$, $CH_2CH_2CH_3$ and $CH(CH_3)_2$ are optionally substituted by 1, 2 or 3 $R_b$, and other variables are as defined in the present disclosure.

In some embodiments of the present disclosure, the $R_2$ is selected from $CH_3$ and $CH_2CH_3$, and other variables are as defined in the present disclosure.

In some embodiments of the present disclosure, the ring A is selected from

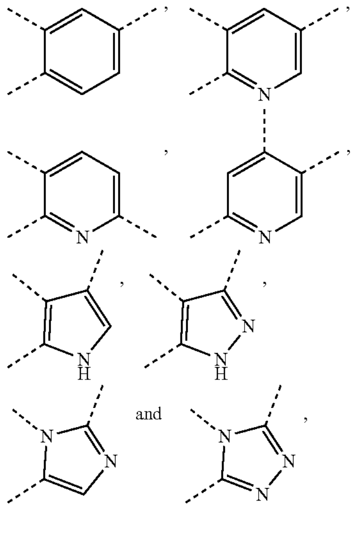

and the

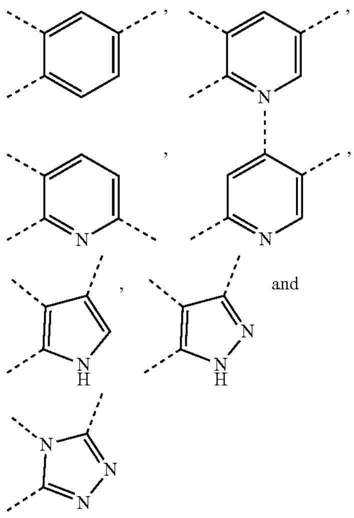

are optionally substituted by 1, 2 or 3 $R_a$, and other variables are as defined in the present disclosure.

In some embodiments of the present disclosure, the ring A is selected from

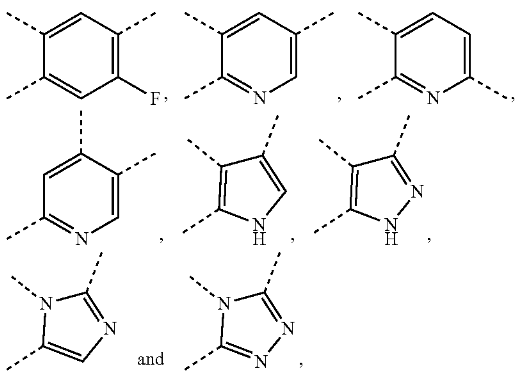

and other variables are as defined in the present disclosure.

In some embodiments of the present disclosure, the structural moiety

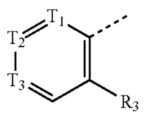

is selected from

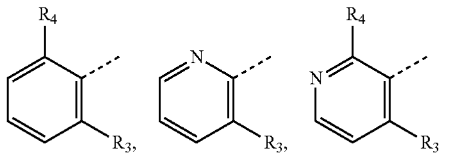

and

-continued

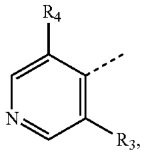

and other variables are as defined in the present disclosure.

In some embodiments of the present disclosure, the structural moiety

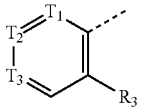

is selected from

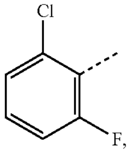
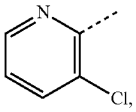
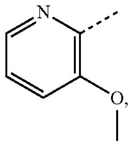
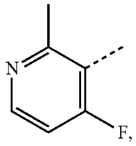
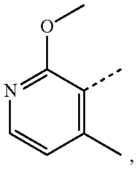
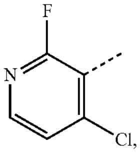
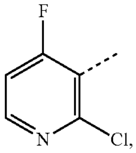
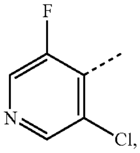
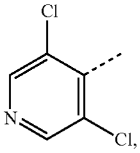
and
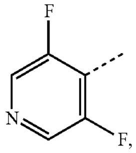

and other variables are as defined in the present disclosure.

In some embodiments of the present disclosure, the compound or the pharmaceutically acceptable salt thereof is selected from, (I-1)

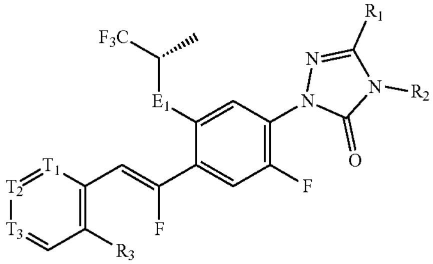

-continued (I-2)

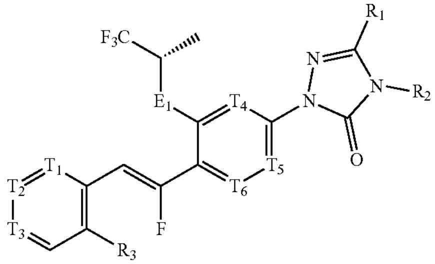

(I-3)

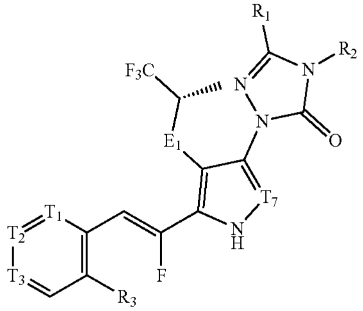

(I-4)

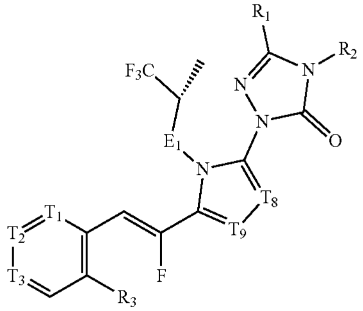

(IV-1)

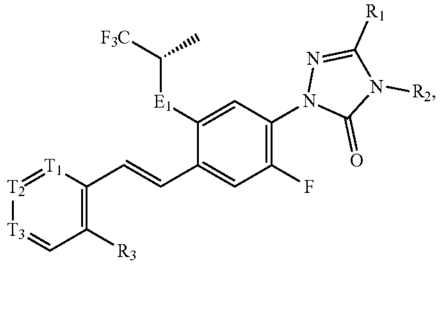

wherein, $T_4$, $T_5$, $T_6$, $T_7$, $T_8$ and $T_9$ are each independently selected from CH and N; $E_1$, $T_1$, $T_2$, $T_3$, $R_1$, $R_2$ and $R_3$ are as defined in the present disclosure.

There are also some embodiments of the present disclosure obtained by an arbitrary combination of the above variables.

The present disclosure also provides a compound represented by the following formula or a pharmaceutically acceptable salt thereof,

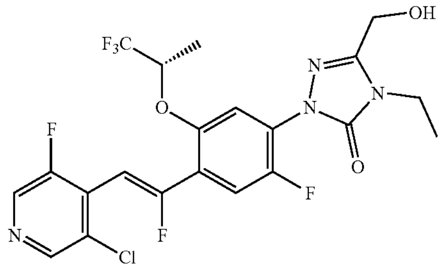
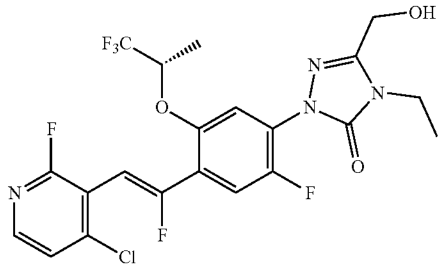
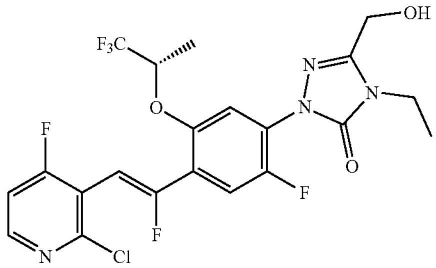
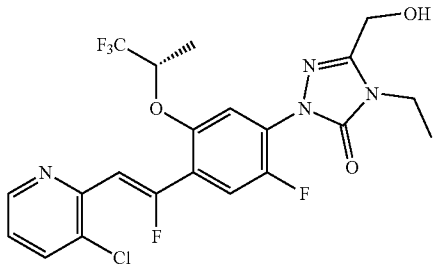
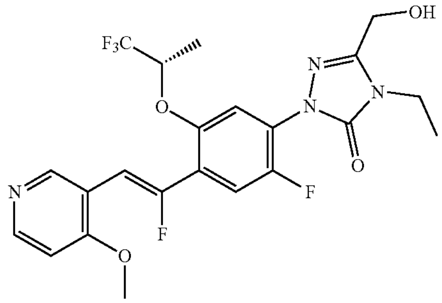
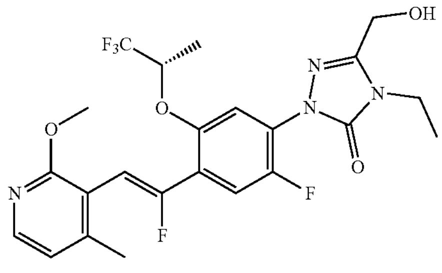
-continued
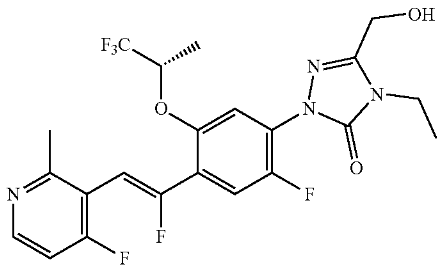
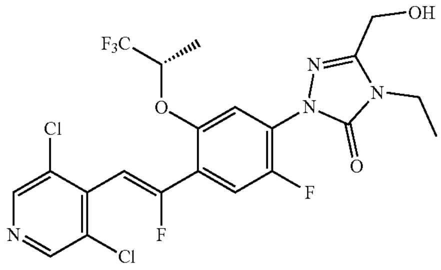
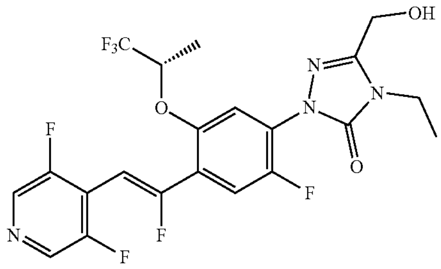
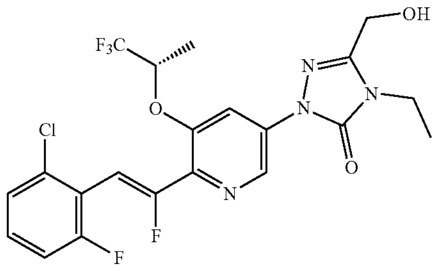
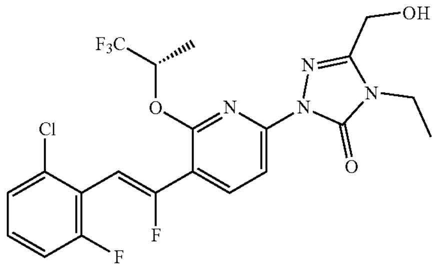
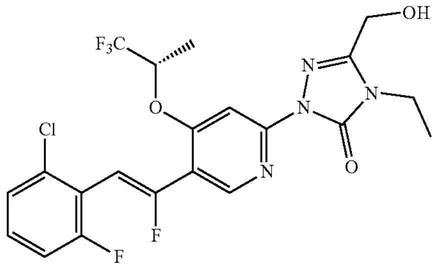

-continued
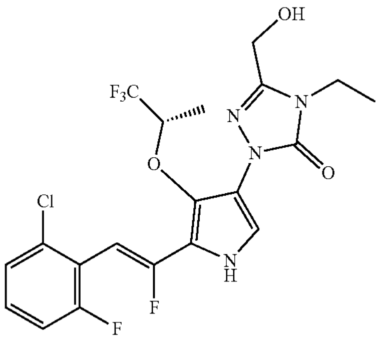
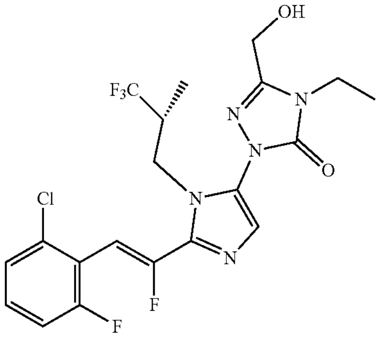
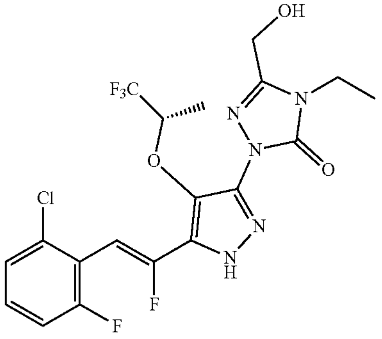
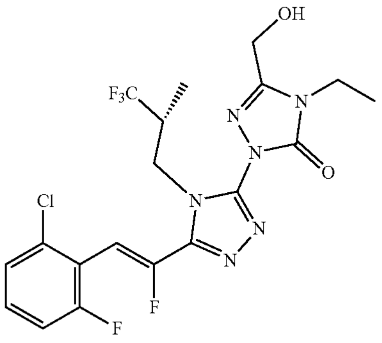
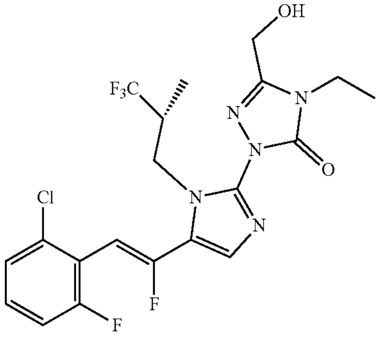
-continued
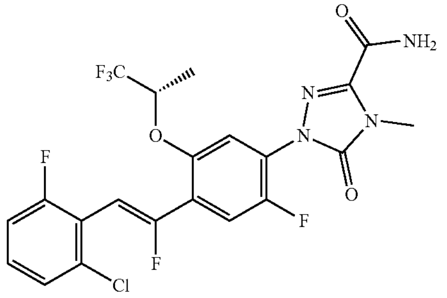
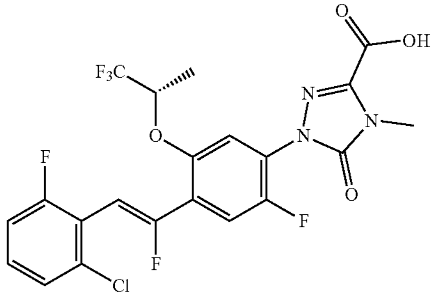
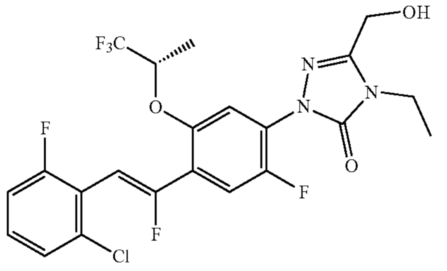
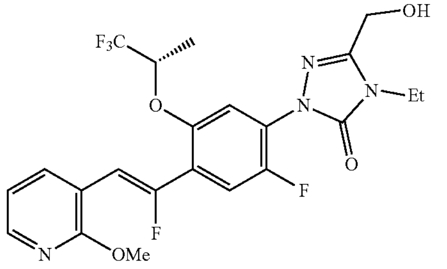
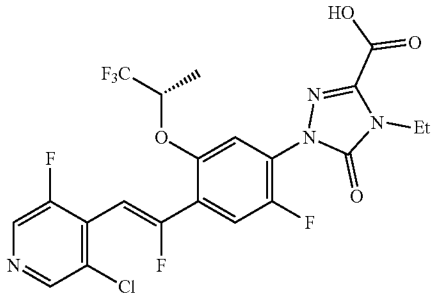
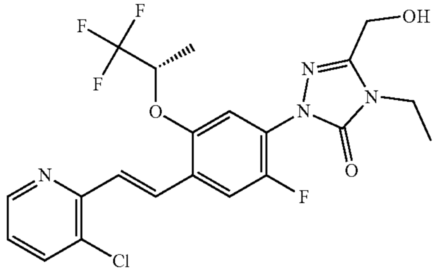

-continued
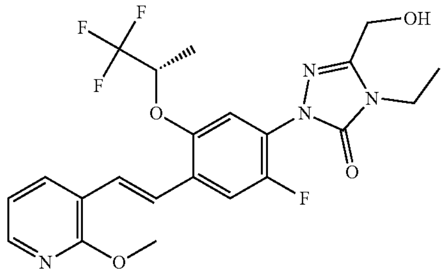
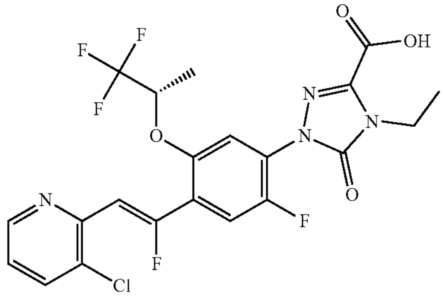
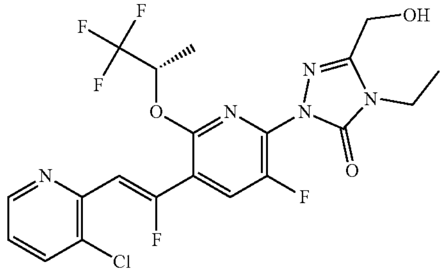
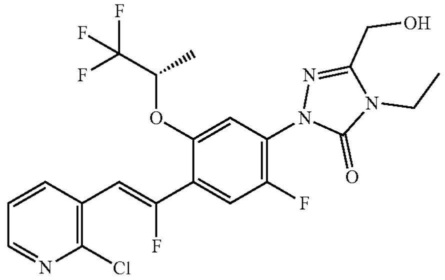
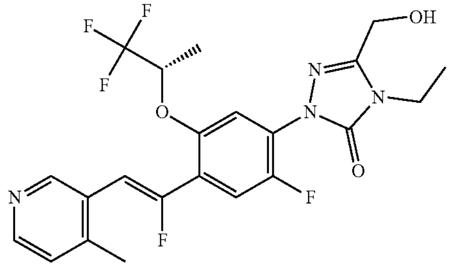
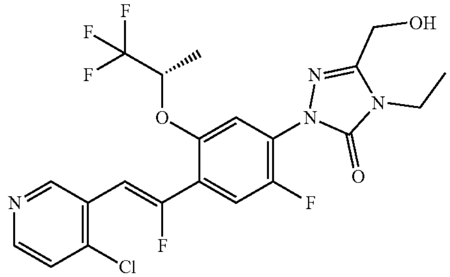
-continued
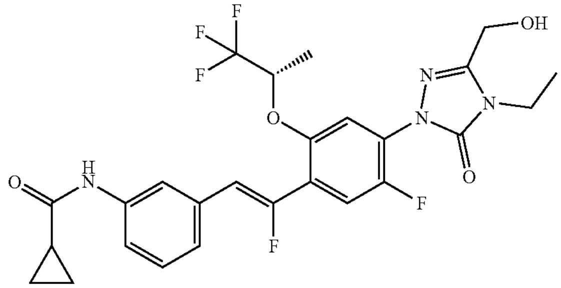
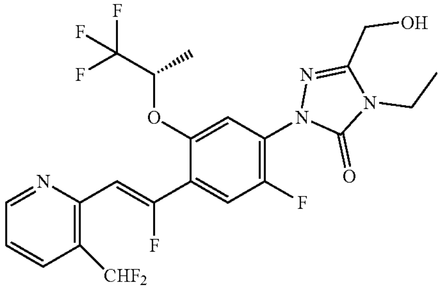
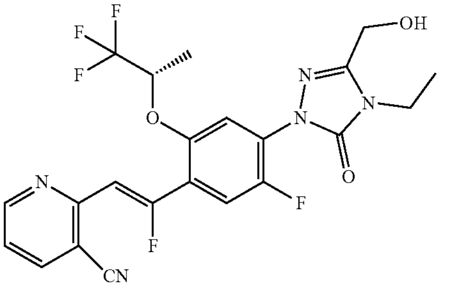
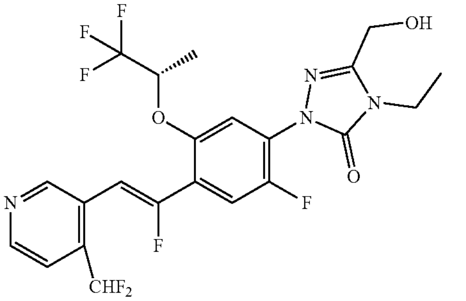
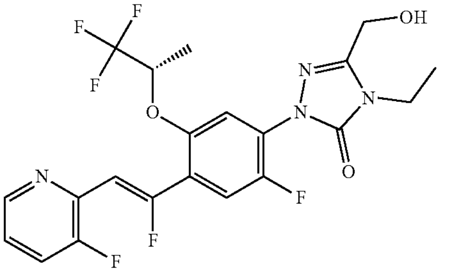
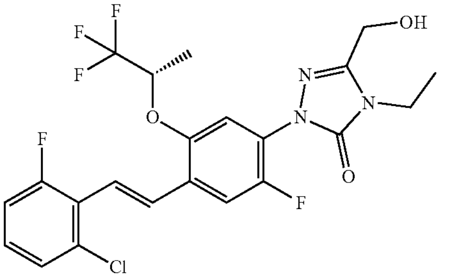

-continued
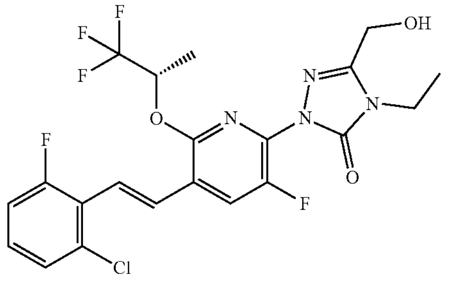
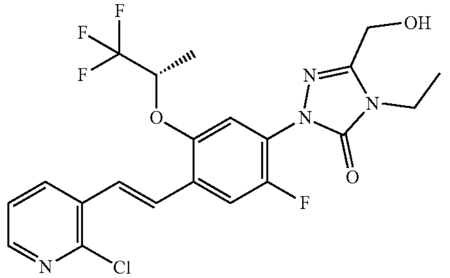
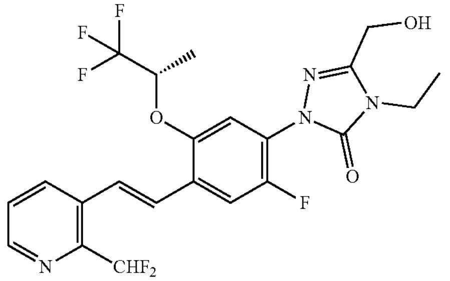
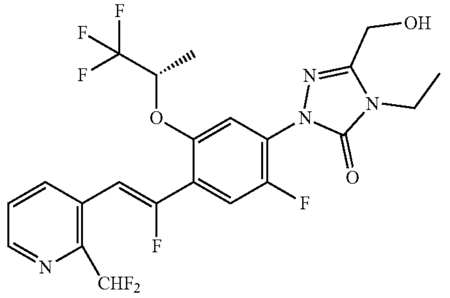
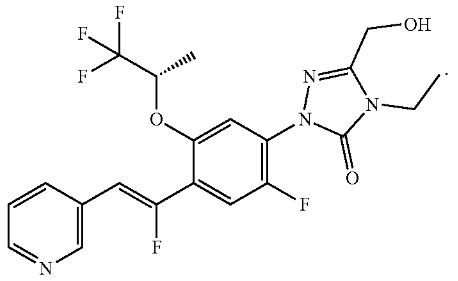
The present disclosure also provides a use of the compound or the pharmaceutically acceptable salt thereof in the manufacture of a medicament for treating diseases related to DHODH.
The compound of the present disclosure can be prepared by the following methods:
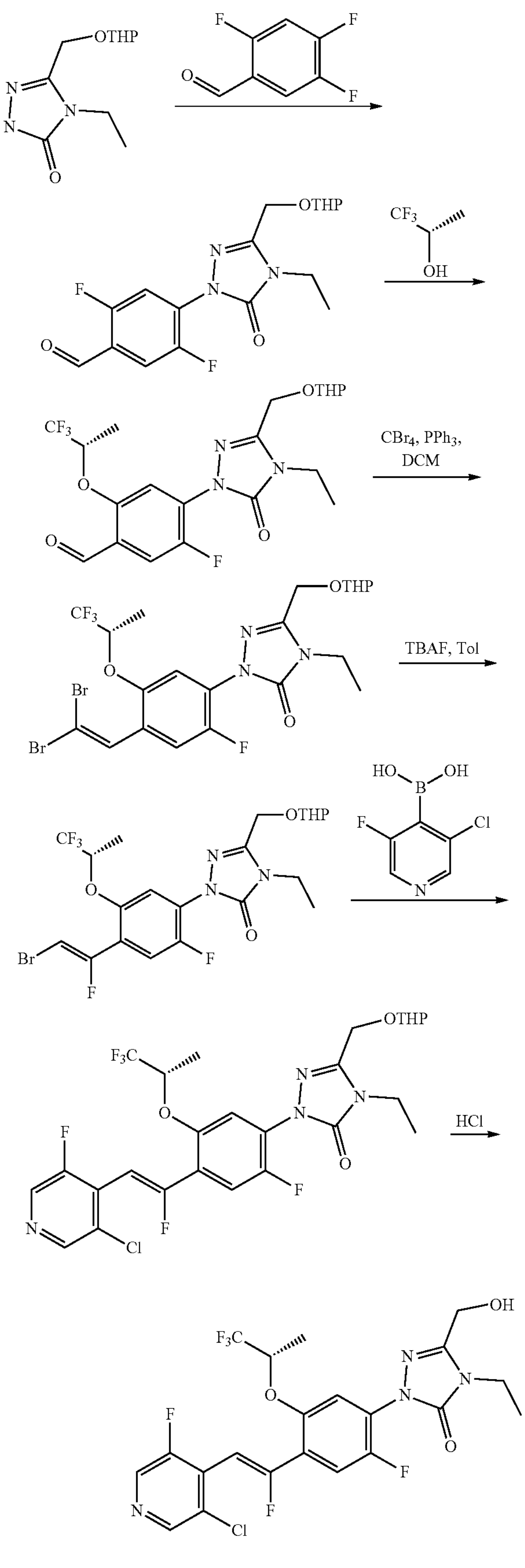

Technical Effect

The compound of the present disclosure has strong inhibitory activity against DHODH enzyme and influenza virus replication. At the same time, the compound of the present disclosure can also effectively inhibit the proliferation of activated PBMC, and has excellent anti-inflammatory activity in vitro. The compound of the present disclosure also has excellent pharmacokinetic properties, including permeability in vitro, metabolic stability in vivo, long half-life of IV and PO, good drug exposure and high oral absorption bioavailability, and efficacy in vivo shows obvious anti-inflammatory effects. In the off-target study, it does not inhibit other kinase targets, but has excellent selectivity for the inhibition against DHODH enzyme.

Relevant Definitions

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt may be obtained by bringing the compound into contact with a sufficient amount of base in a pure solution or a suitable inert solvent. The pharmaceutically acceptable base addition salt includes a salt of sodium, potassium, calcium, ammonium, organic ammonia or magnesium, or similar salts. When the compound of the present disclosure contains a relatively basic functional group, an acid addition salt may be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When the enumerative linking group does not indicate the direction for linking, the direction for linking is arbitrary, for example, the linking group L contained in

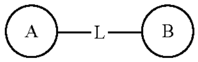

is -M-W—, then -M-W— can link ring A and ring B to form

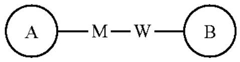

in the direction same as left-to-right reading order, and form

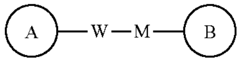

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (  ), a straight dashed bond (  )

or a wavy line ( 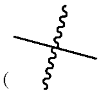 ).

For example, the straight solid bond in —$OCH_3$ means that it is linked to other groups through the oxygen atom in the group; the straight dashed bonds in

means that it is linked to other groups through the two ends of nitrogen atom in the group; the wave lines in

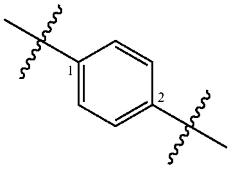 [SMILES: *c1ccc(*)cc1]

means that the phenyl group is linked to other groups through carbon atoms at position 1 and position 2;

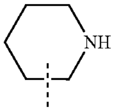

means that it can be linked to other groups through any linkable sites on the piperidinyl by one chemical bond, including at least four types of linkage, including

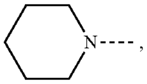 , 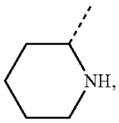 , 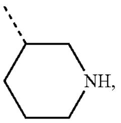 , 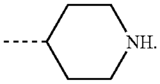

Even though the H atom is drawn on the —N—,

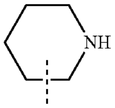

still includes the linkage of

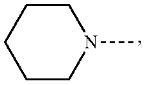

merely when one chemical bond was connected, the H of this site will be reduced by one to the corresponding monovalent piperidinyl;

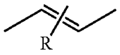

means that R can be arbitrarily connected at both ends of the double bond, which means

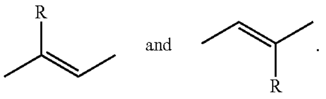

Unless otherwise specified, the term "$C_{1-6}$ alkyl" refers to a linear or branched saturated hydrocarbon group having 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl and t-butyl), amyl (including n-amyl, isoamyl and neopentyl), hexyl and the like.

Unless otherwise specified, the term "$C_{1-3}$ alkyl" refers to a linear or branched saturated hydrocarbon group having 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

The following abbreviations are used in the present disclosure: DIBAL-H refers to diisobutylaluminum hydride.

The compounds are named according to the conventional naming principles in the art or by ChemDraw® software, and the commercially available compounds use the supplier catalog names.

DETAILED DESCRIPTION OF THE PREFERRED EMBODIMENT

Figure 1:
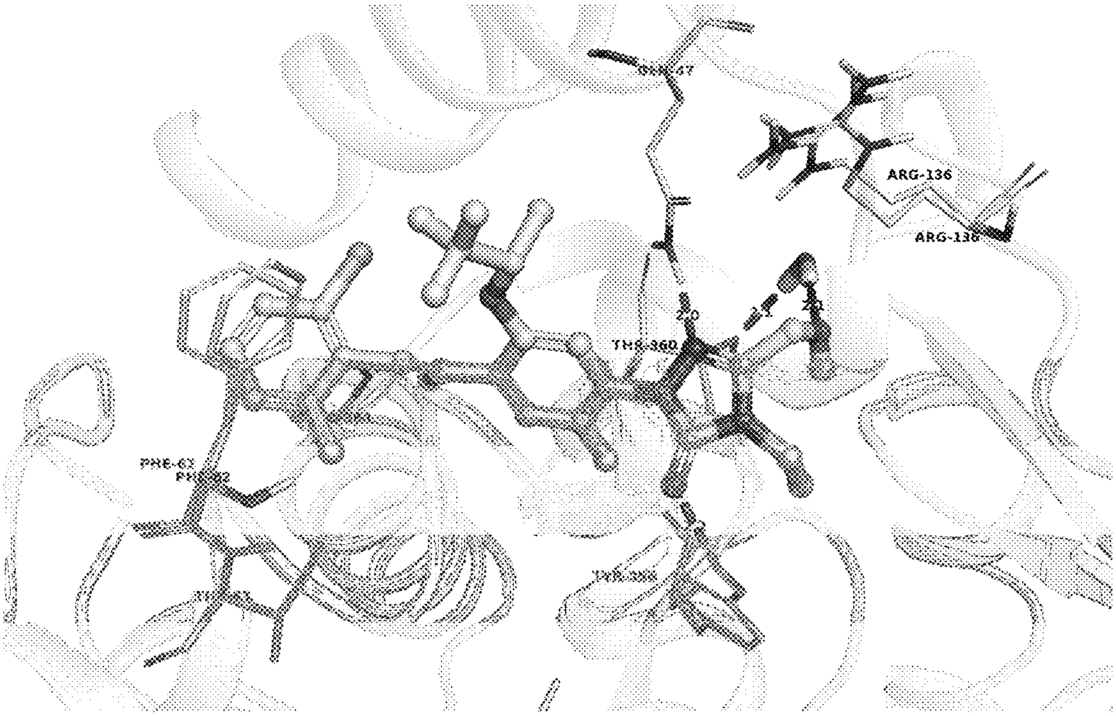
FIG. 1 is the molecular docking diagram of compound 1 and DHODH.
Figure 2:
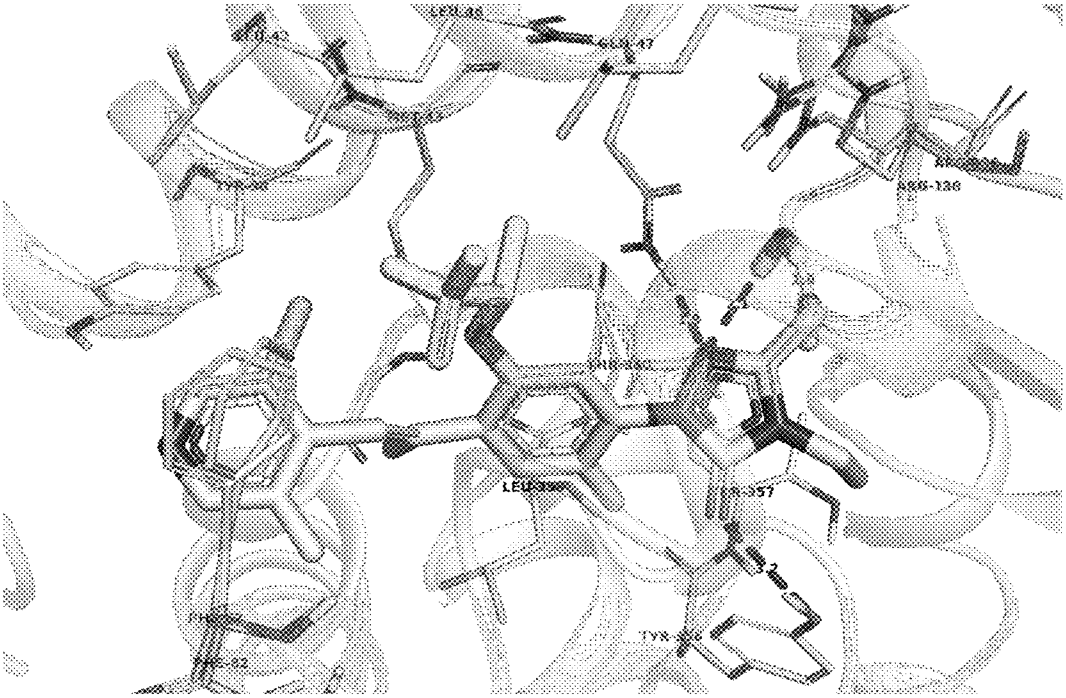
FIG. 2 is the molecular docking diagram of compound 2 and DHODH.
Figure 3:
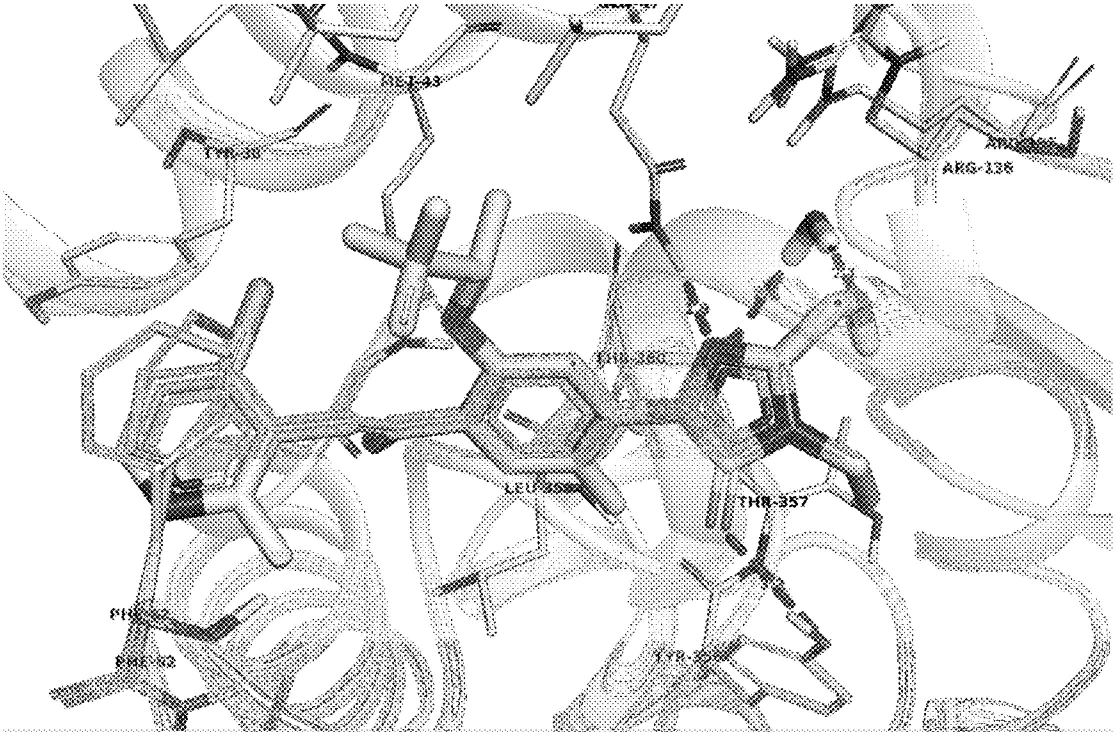
FIG. 3 is the molecular docking diagram of compound 3 and DHODH.
Figure 4:
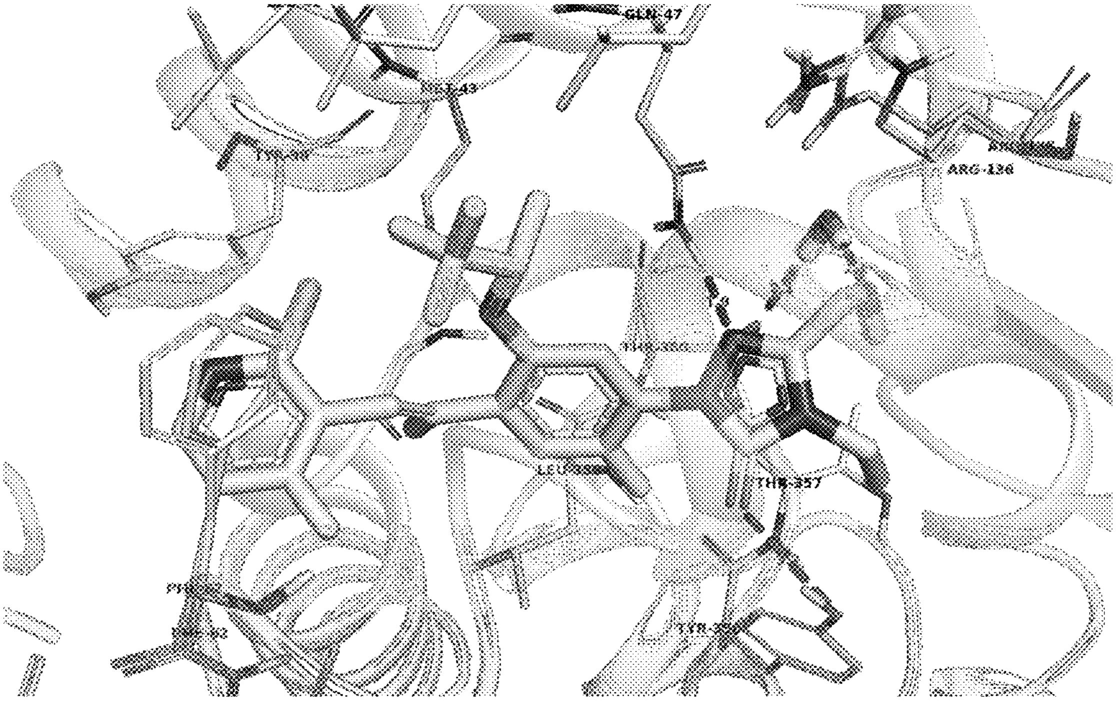
FIG. 4 is the molecular docking diagram of compound 4 and DHODH.
Figure 5:
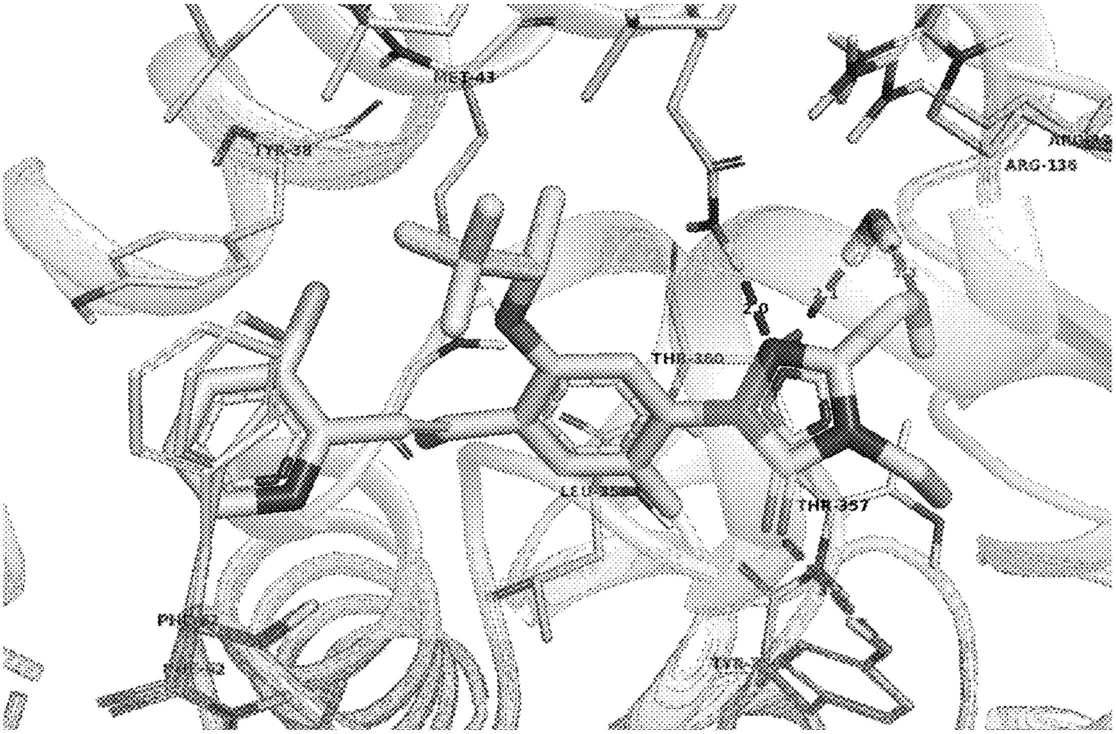
FIG. 5 is the molecular docking diagram of compound 5 and DHODH.
Figure 6:
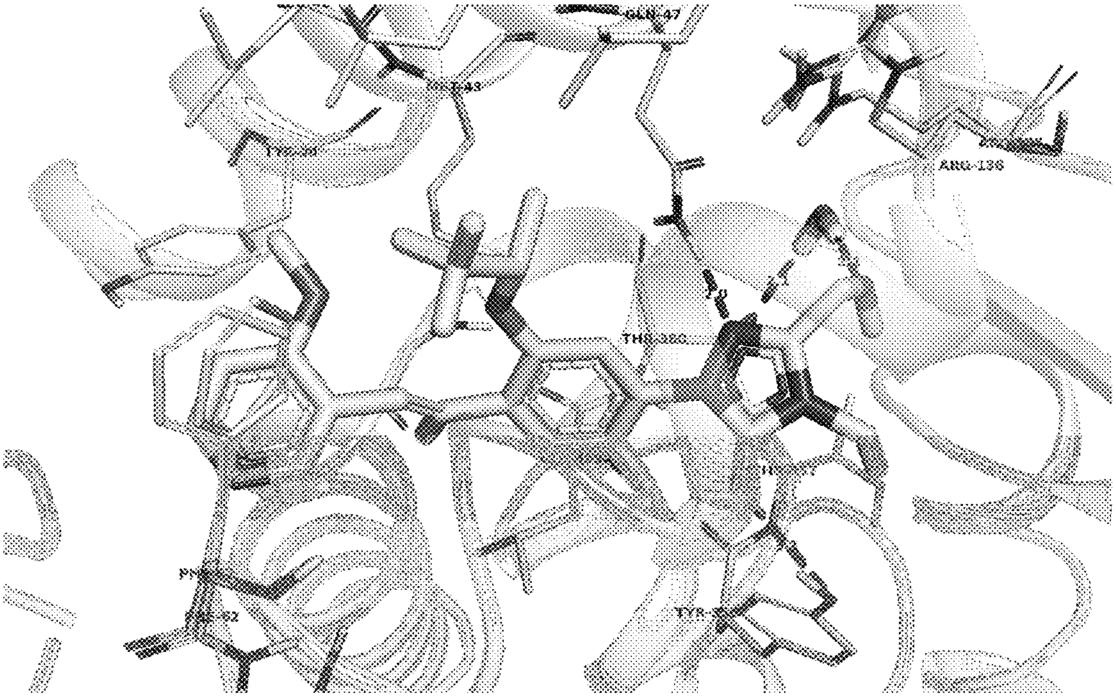
FIG. 6 is the molecular docking diagram of compound A and DHODH.
Figure 7:
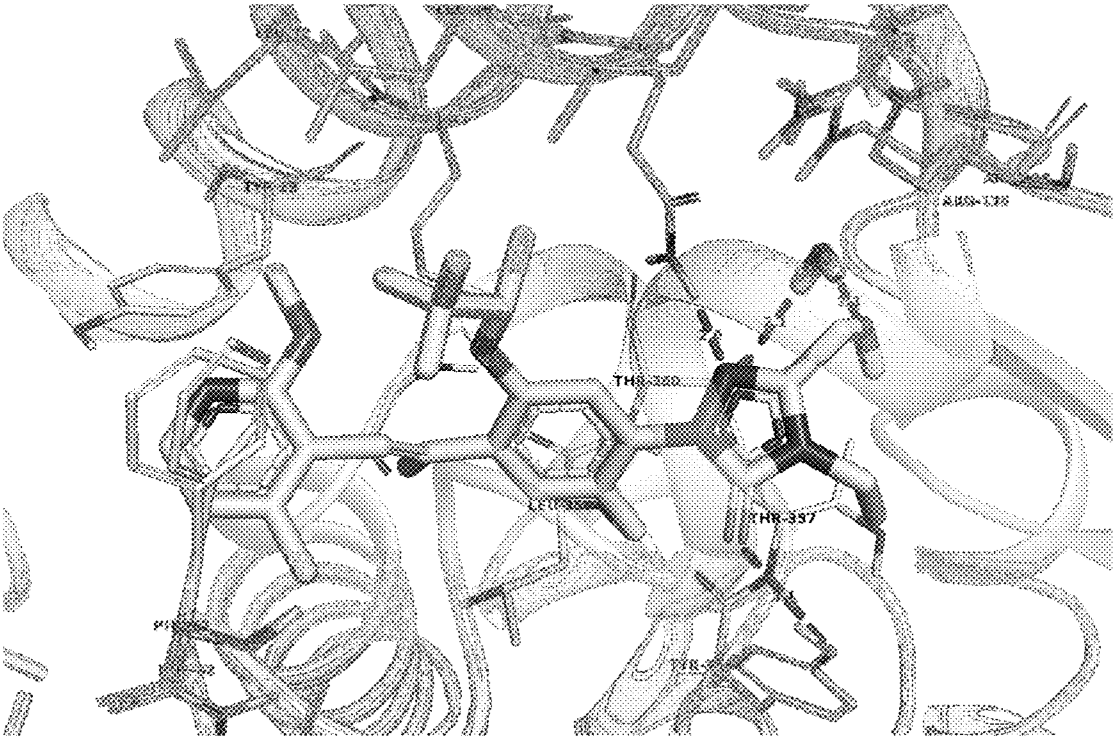
FIG. 7 is the molecular docking diagram of compound 7 and DHODH.
Figure 8:
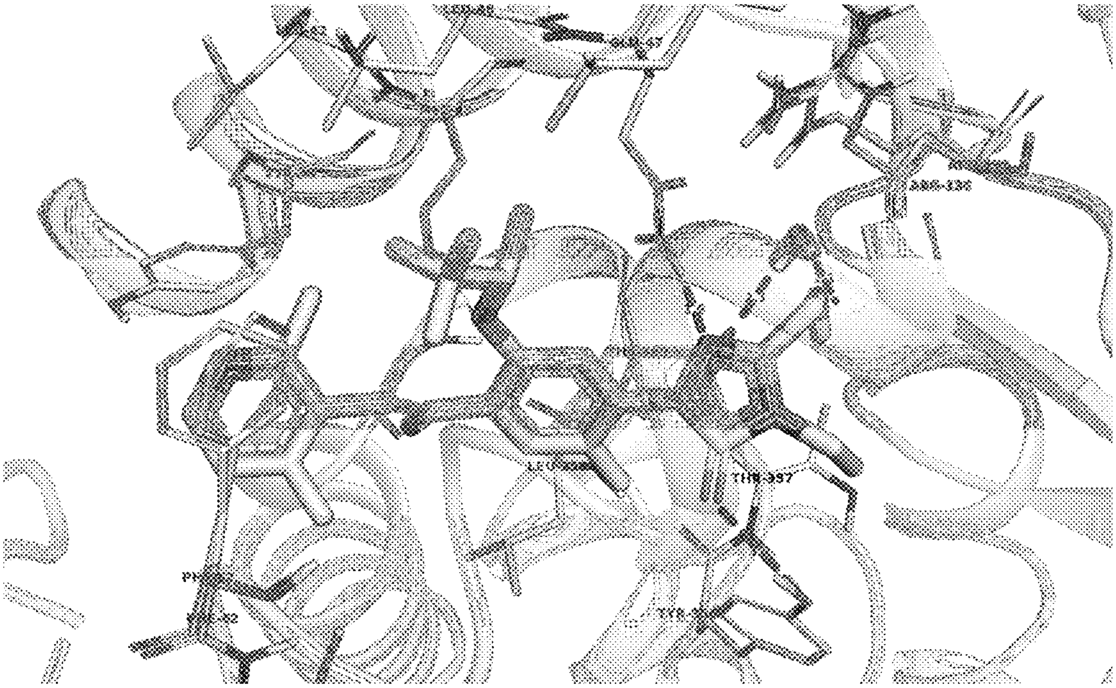
FIG. 8 is the molecular docking diagram of compound 8 and DHODH.
Figure 9:
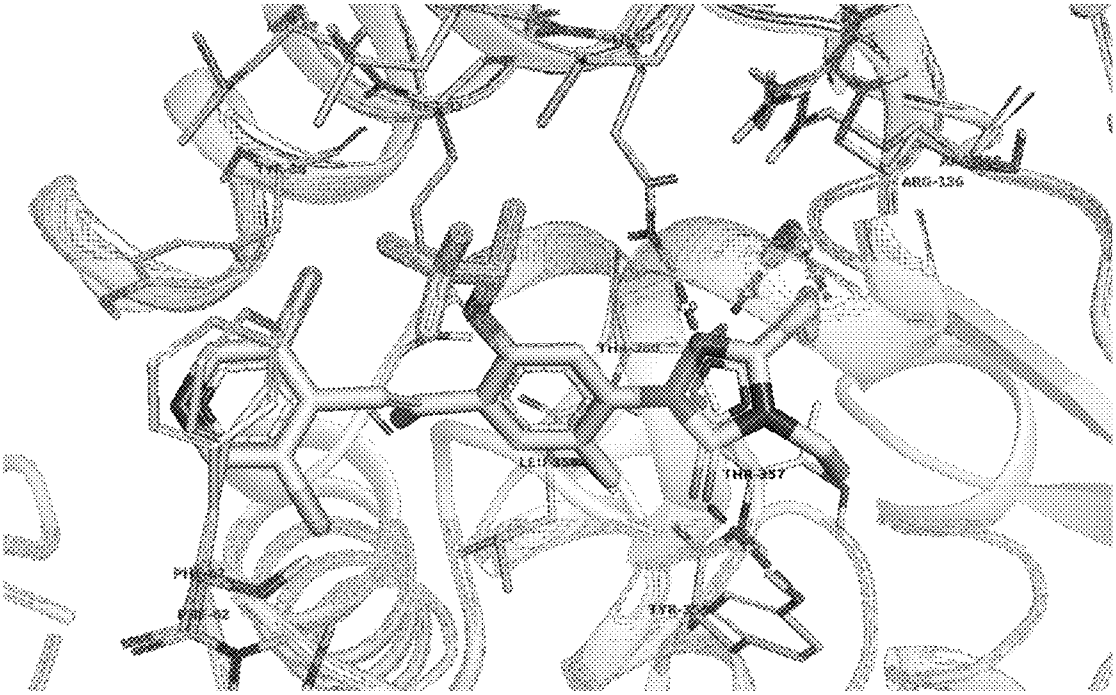
FIG. 9 is the molecular docking diagram of compound 9 and DHODH.
Figure 10:
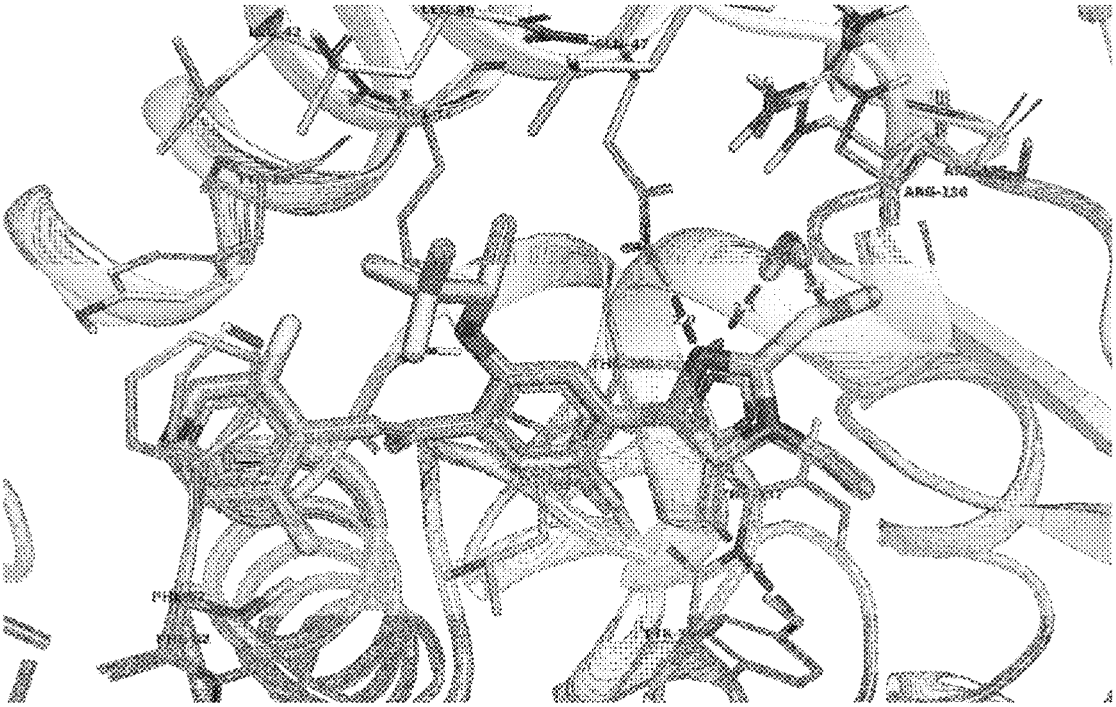
FIG. 10 is the molecular docking diagram of compound 10 and DHODH.
Figure 11:
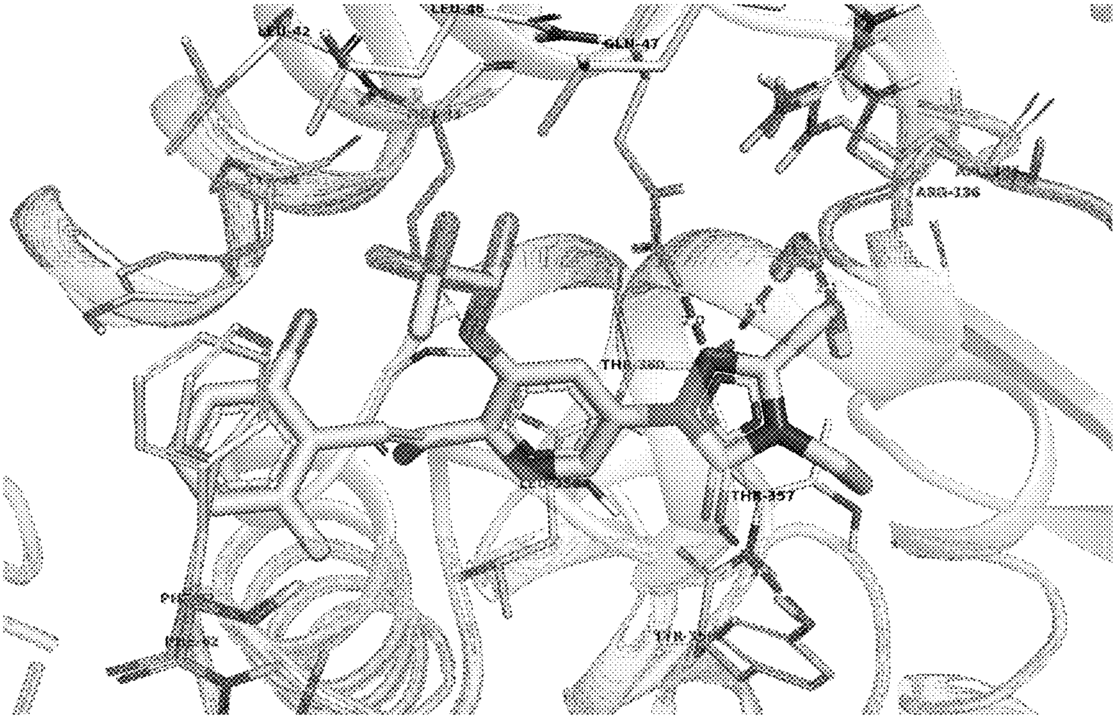
FIG. 11 is the molecular docking diagram of compound 11 and DHODH.
Figure 12:
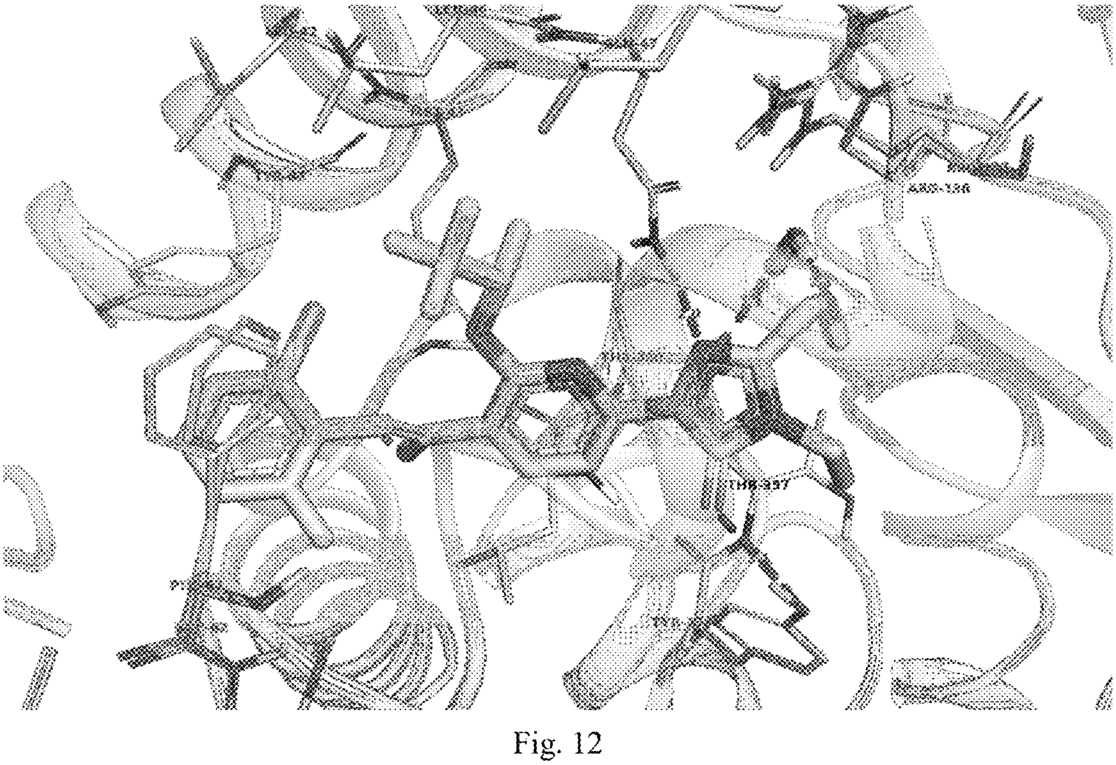
FIG. 12 is the molecular docking diagram of compound 12 and DHODH.
Figure 13:
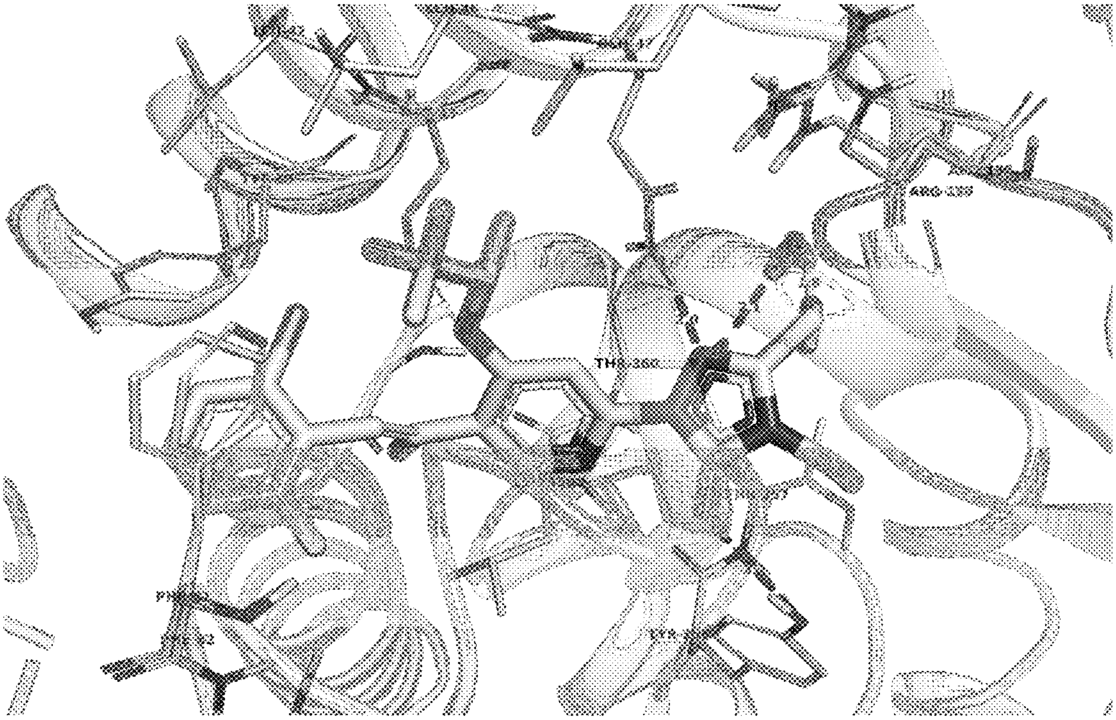
FIG. 13 is the molecular docking diagram of compound 13 and DHODH.
Figure 14:
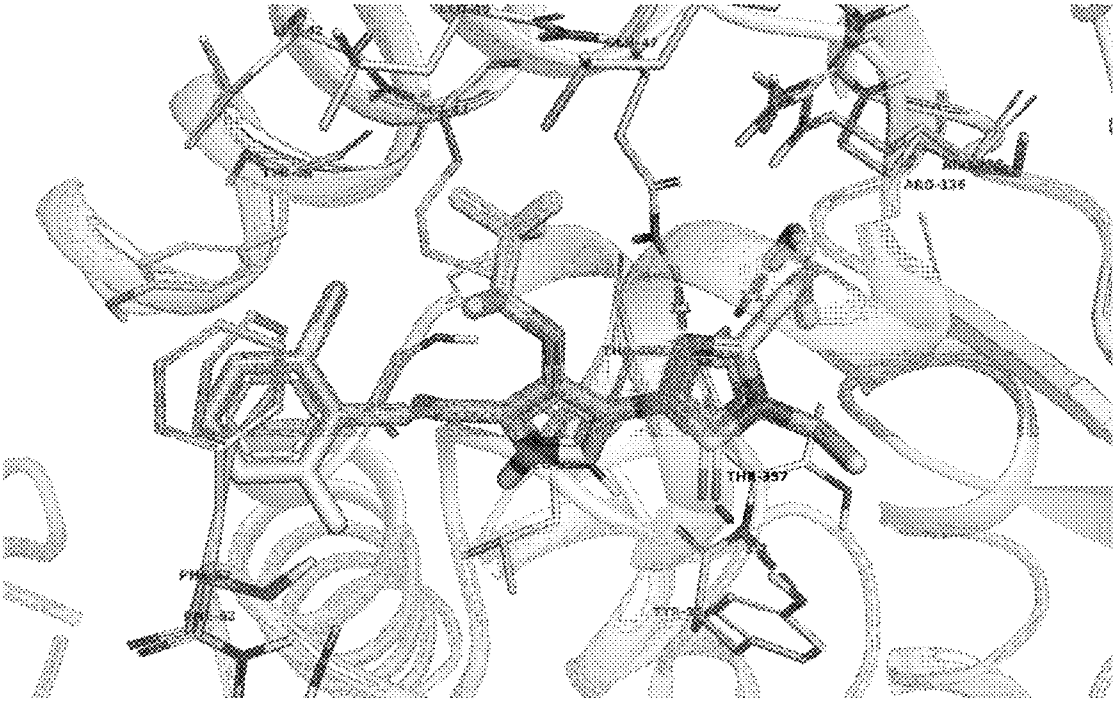
FIG. 14 is the molecular docking diagram of compound 14 and DHODH.
Figure 15:
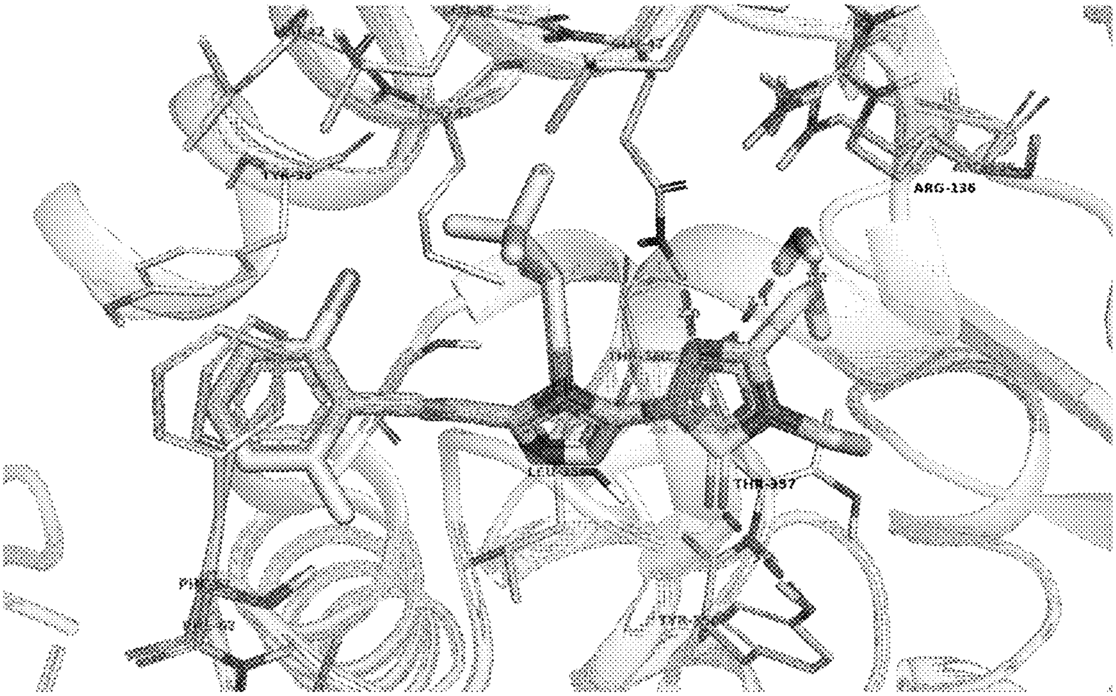
FIG. 15 is the molecular docking diagram of compound 15 and DHODH.
Figure 16:
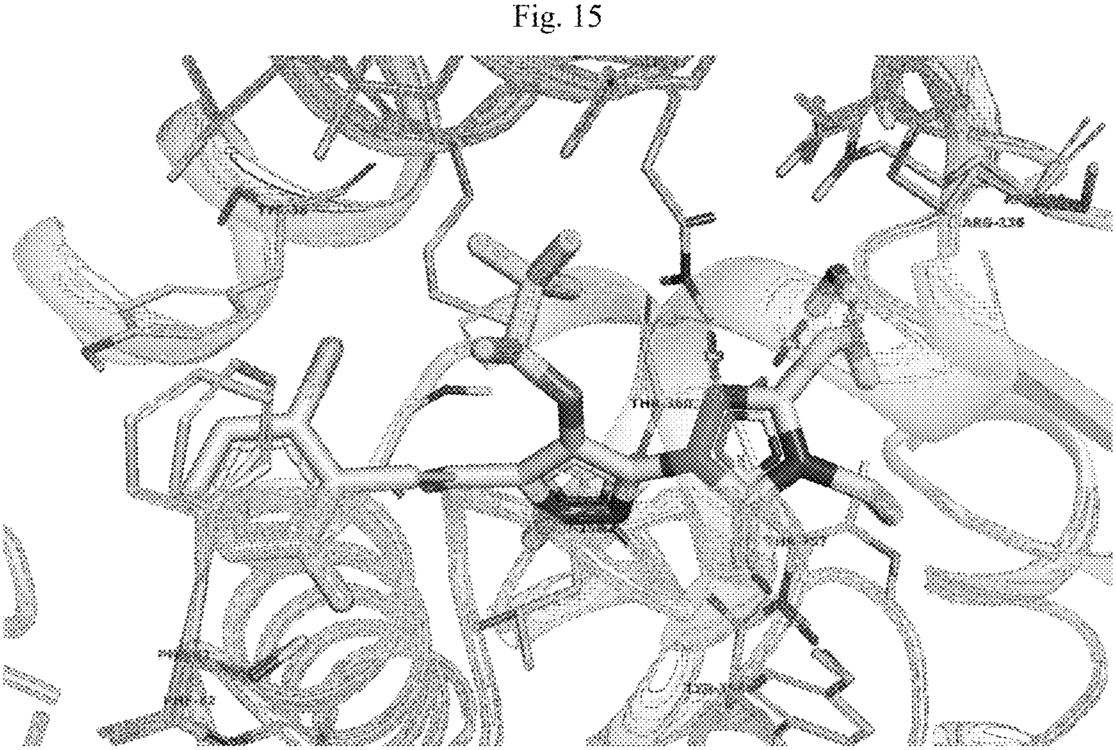
FIG. 16 is the molecular docking diagram of compound 16 and DHODH.
Figure 17:
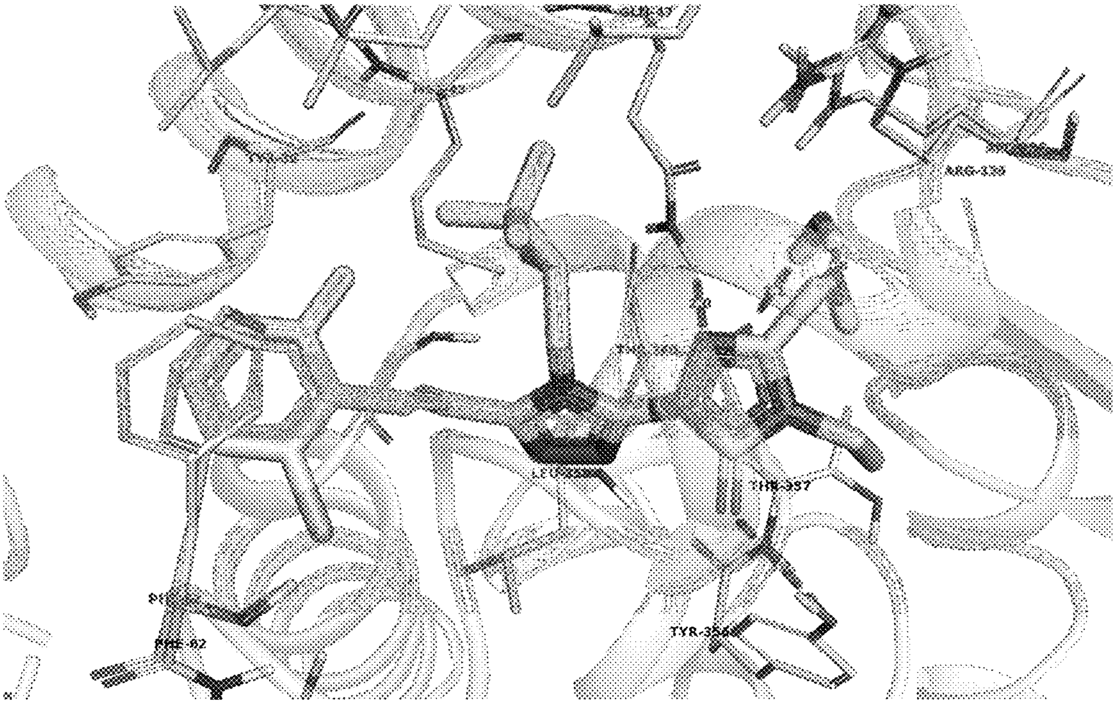
FIG. 17 is the molecular docking diagram of compound 17 and DHODH.
Figure 18:
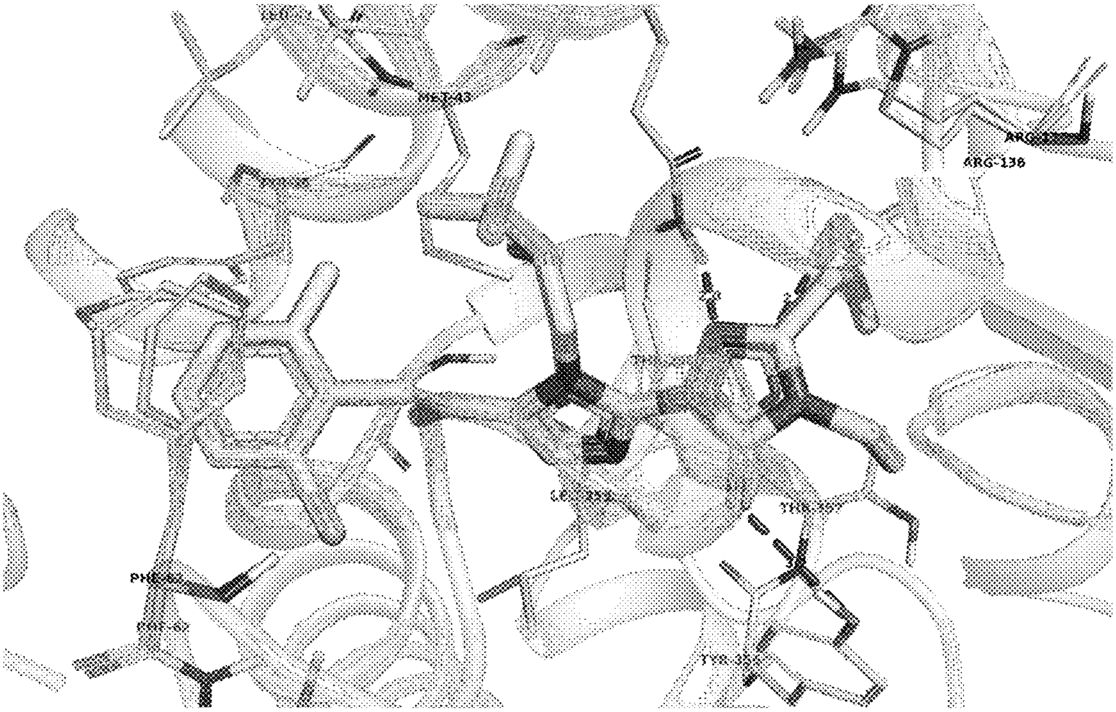
FIG. 18 is the molecular docking diagram of compound 18 and DHODH.
Figure 19:
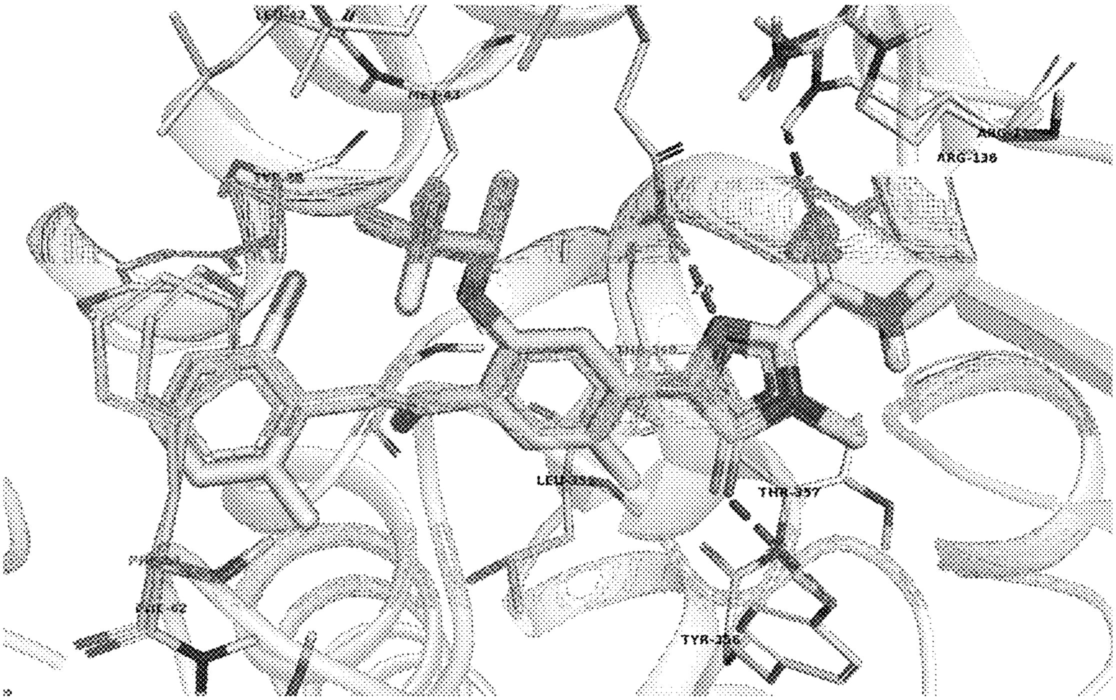
FIG. 19 is the molecular docking diagram of compound 19 and DHODH.
Figure 20:
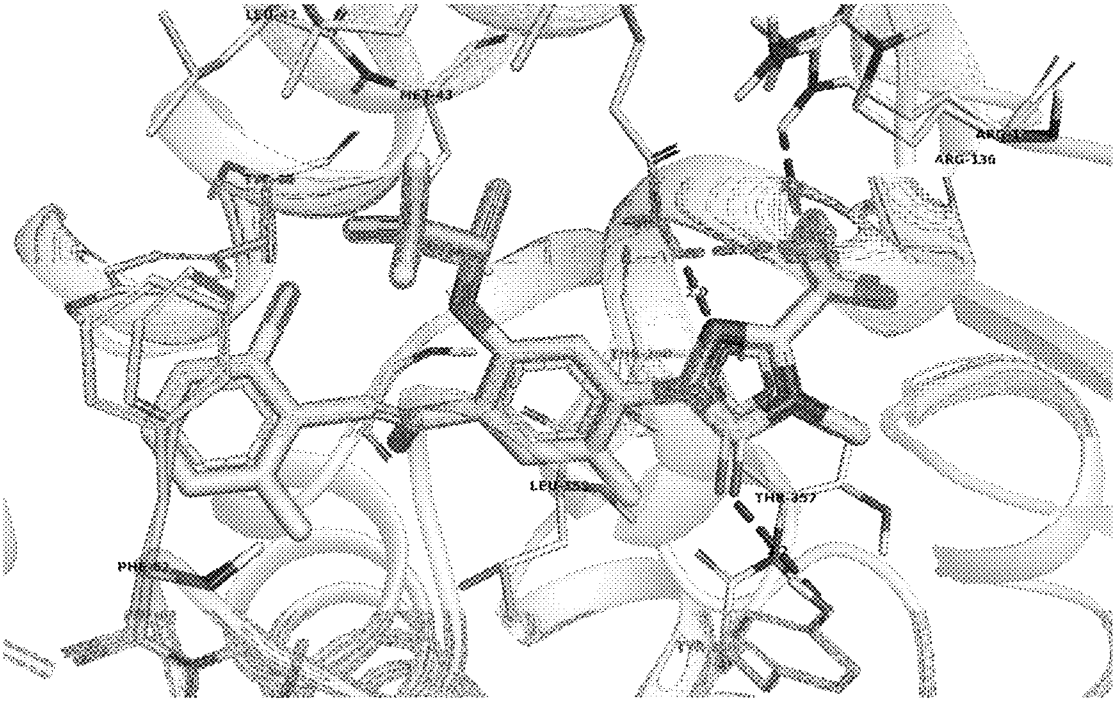
FIG. 20 is the molecular docking diagram of compound 20 and DHODH.

The present disclosure is described in detail by the embodiments below, but it does not mean that there are any adverse restrictions on the present disclosure. The present disclosure has been described in detail herein, and its specific embodiments have also been disclosed. For one skilled in the art, it is obvious to make various modifications and improvements to the embodiments of the present disclosure without departing from the spirit and scope of the present disclosure.

Calculation Example 1
Prediction of the Binding Mode of the Compound of the Present Disclosure to DHODH:
Compound 1
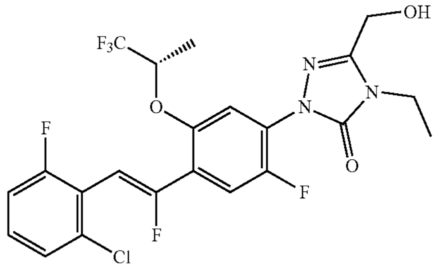
Compound 2
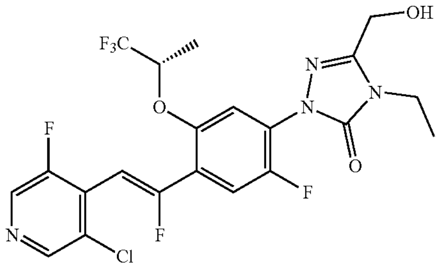
Compound 3
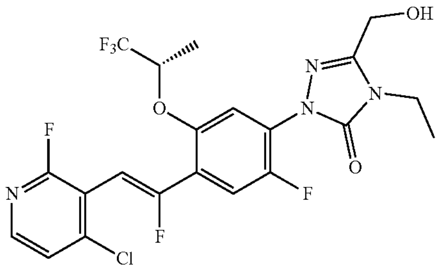
Compound 4
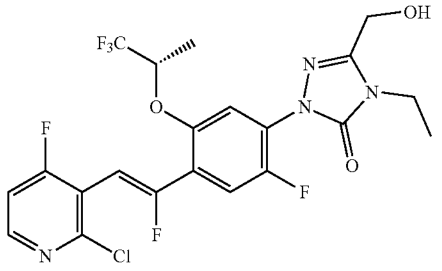
Compound 5
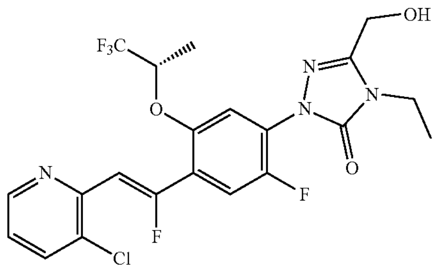
-continued
Compound A
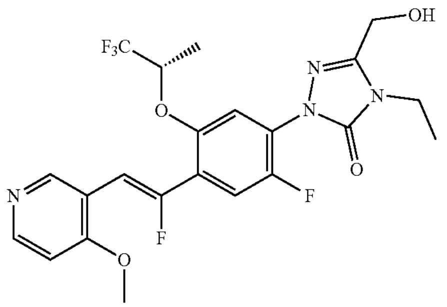
Compound 7
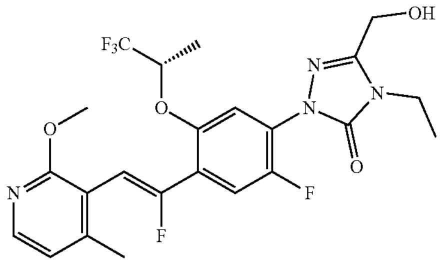
Compound 8
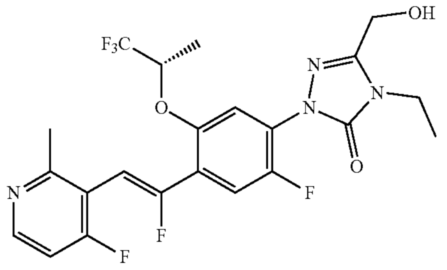
Compound 9
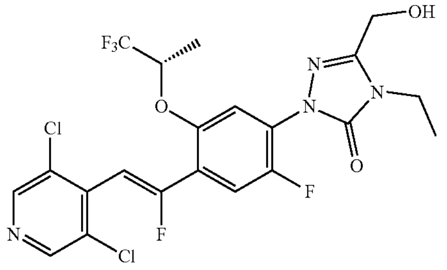
Compound 10
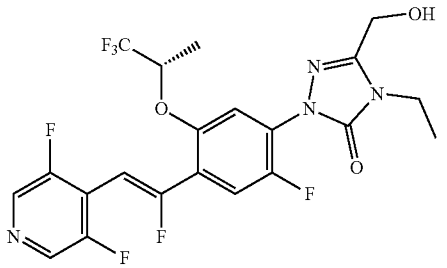

-continued
Compound 11
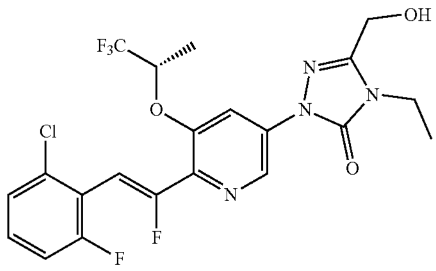
Compound 12
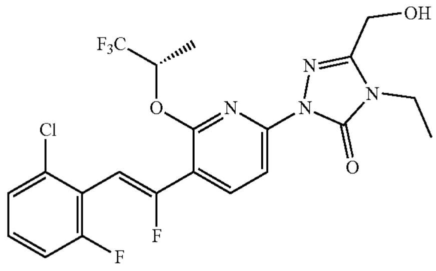
Compound 13
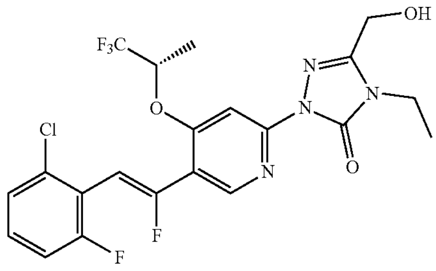
Compound 14
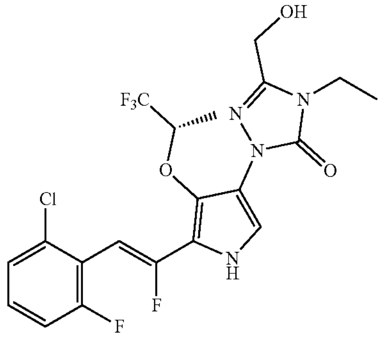
Compound 15
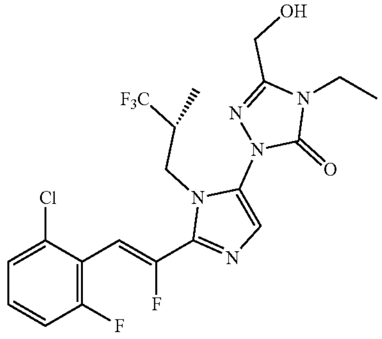
-continued
Compound 16
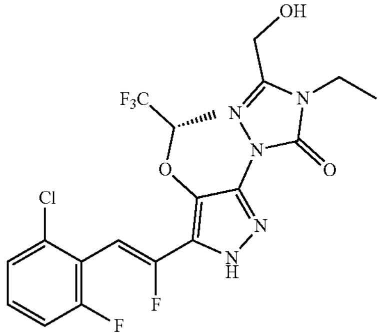
Compound 17
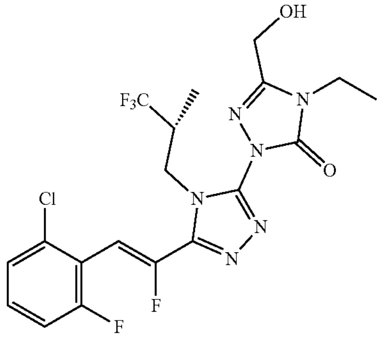
Compound 18
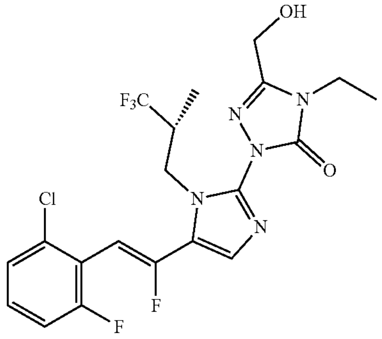
Compound 19
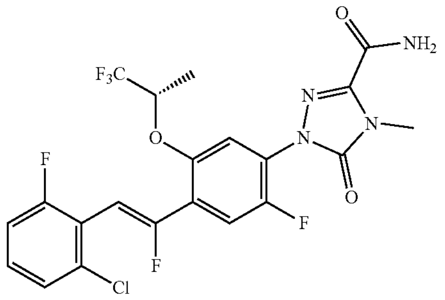

-continued

Compound 20

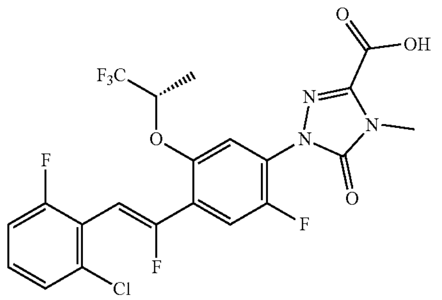

Molecular docking was performed by using GlideSP[1] in Maestro (Schrödinger version 2017-2) and the default options. The cocrystal structure of DHODH (PDB TD code: 6QU7) was selected as the docking template. For the preparation of protein, hydrogen atoms were added using the protein preparation wizard module of Maestro [2] and the OPLS3 force field was used. For the preparation of ligand, 3D structure was generated and energy minimization was performed using LigPrep [3]. A 30 Å docking grid was generated using the ligand centroid in the 6QU7 crystal structure. The ligand was then removed and the example compound was placed during molecular docking. The type of protein receptor-ligand interaction was analyzed, and then a reasonable docking conformation was selected and saved according to the calculated docking score and globalStrain value. The molecular docking diagrams of the compounds of the present disclosure are as shown in FIGS. 1 to 20.

[1] Glide, Schrödinger, LLC, New York, NY, 2017.

[2] Maestro, Schrödinger, LLC, New York, NY, 2017.

[3] LigPrep, Schrödinger, LLC, New York, NY, 2017.

Conclusion: The compounds of the present disclosure have a better binding mode with DHODH protein.

Example 1: Synthesis of Compound 6

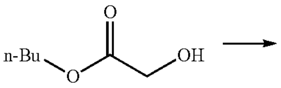

6-1

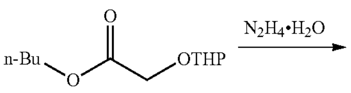

6-2

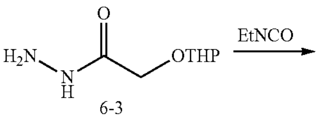

6-3

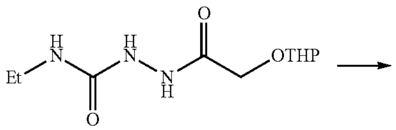

6-4

-continued

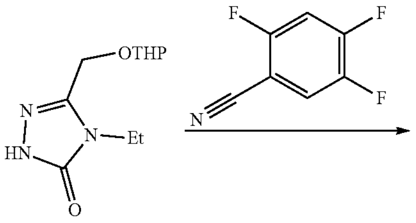

6-5

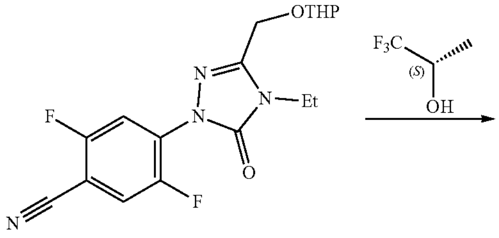

6-6

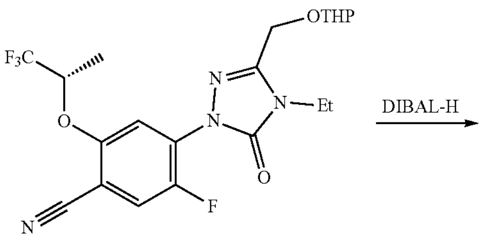

6-7

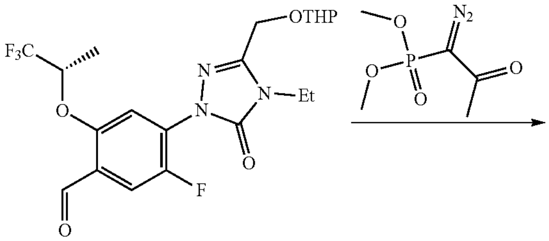

6-8

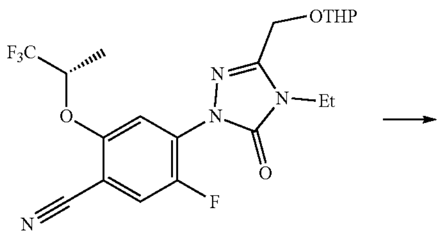

6-9

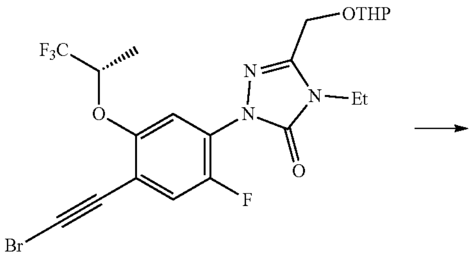

6-10

-continued

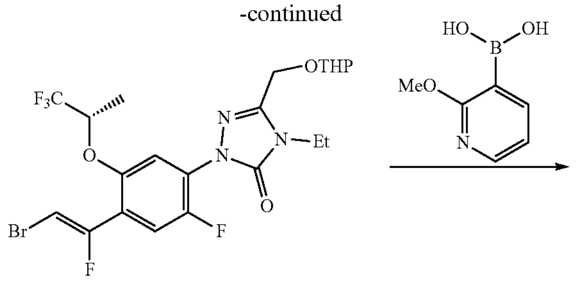

6-11

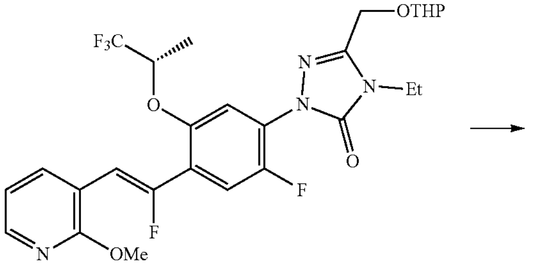

6-12

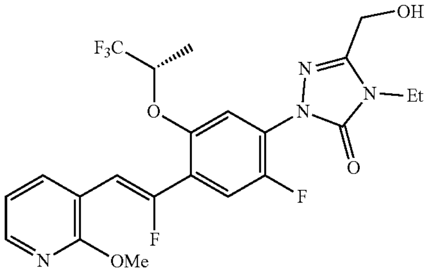

Compound 6

Step 1: Preparation of Compound 6-2

Compound 6-1 (10 g, 75.67 mmol, 9.80 mL, 1 eq) was dissolved in dichloromethane (100 mL), then p-toluenesulfonic acid (195.45 mg, 1.14 mmol, 0.015 eq) and 3,4-dihydro-2H-pyran (7.64 g, 90.80 mmol, 8.30 mL, 1.2 eq) were added and stirred at 25° C. for 16 hours. The raw materials were completely reacted, and saturated sodium bicarbonate solution (100 mL) was added to the reaction solution and stirred for 10 min, then the organic phase was separated. The aqueous phase was extracted with dichloromethane (50 mL*3), and all the organic phases were combined and washed with saturated brine (100 mL*3), dried over anhydrous sodium sulfate, filtered and the filtrate was concentrated under reduced pressure. The crude product was purified by column chromatography (petroleum ether: ethyl acetate=1:0-100:3) to obtain compound 6-2.

$^1$H NMR (400 MHz, $CDCl_3$) δ 4.73 (t, J=3.26 Hz, 1H), 4.20 (s, 2H), 4.15 (dt, J=2.01, 6.65 Hz, 2H), 3.82-3.89 (m, 1H), 3.51 (dtd, J=1.88, 4.06, 11.07 Hz, 1H), 1.80-1.91 (m, 1H), 1.71-1.77 (m, 2H), 1.60-1.67 (m, 2H), 1.56-1.60 (m, 1H), 1.49-1.56 (m, 2H), 1.31-1.42 (m, 2H), 0.92 (t, J=7.40 Hz, 3H).

Step 2: Preparation of Compound 6-3

Compound 6-2 (11.7 g, 54.10 mmol, 1 eq) and hydrazine hydrate (4.78 g, 81.15 mmol, 4.64 mL, content of 85%, 1.5 eq) were added to a 100 mL three-necked reaction flask and stirred at 60° C. for 3 hours. The raw materials were completely reacted, and the reaction solution was cooled to room temperature, then water (40 mL) was added. Methyl tert-butyl ether (10 mL) was added for extraction, and the aqueous phase was collected. The aqueous solution of compound 6-3 was obtained, which was directly fed to the next step without purification.

Step 3: Preparation of Compound 6-4

Compound 6-3 (9.4 g, 53.96 mmol, 1 eq) was dissolved in water (40 mL) at 10° C. Ethyl isocyanate (5.75 g, 80.94 mmol, 6.41 mL, 1.5 eq) was added, heated to 25° C., and stirred for 6 hours. The raw materials were completely reacted, and the aqueous solution of compound 6-4 was obtained, which was directly fed to the next step without purification.

Step 4: Preparation of Compound 6-5

Sodium hydroxide aqueous solution (1.08 g, 13.50 mmol, content of 50%, 0.25 eq) was added dropwise to compound 6-4 (13.24 g, 53.98 mmol, 1 eq) aqueous solution (50 mL), and stirred at 90° C. for 6 hours. The raw materials were completely reacted, and hydrochloric acid aqueous solution (1 M) was added dropwise to the reaction solution and the pH was adjusted to 7.4; dichloromethane (50 mL*5) was added for extraction, and the organic phases were combined, washed with saturated brine (50 mL*2), dried over anhydrous sodium sulfate, filtered, and the filtrate was concentrated under reduced pressure to obtain compound 6-5. $^1$H NMR (400 MHz, $CD_3OD$) δ ppm 4.73 (t, J=3.51 Hz, 1H), 4.64 (d, J=12.80 Hz, 1H), 4.44 (d, J=12.80 Hz, 1H), 3.75-3.83 (m, 1H), 3.53-3.60 (m, 2H), 1.71-1.85 (m, 2H), 1.47-1.64 (m, 6H), 1.31 (t, J=7.28 Hz, 3H).

Step 5: Preparation of Compound 6-6

Compound 6-5 (3 g, 13.20 mmol, 1 eq) and 2,4,5-trifluorobenzonitrile (2.28 g, 14.52 mmol, 1.1 eq) were dissolved in acetonitrile (30 mL), then potassium phosphate (5.60 g, 26.40 mmol, 2 eq) was added, and the reaction solution was stirred at 70° C. for 12 hours. After the raw materials were completely reacted, the reaction solution was quenched by adding water (30 mL) to the reaction solution, extracted by adding ethyl acetate (30 mL*5). The organic phases were combined, washed with saturated brine (30 mL*2), dried over anhydrous sodium sulfate, filtered, and the filtrate was concentrated under reduced pressure. The crude product was purified by column chromatography (petroleum ether:ethyl acetate=1:0-2:1) to obtain compound 6-6. MS ESI calculated for $C_{17}H_{18}F_2N_4O_3$ $[M+H]^+$ 365, found 365. $^1$H NMR (400 MHz, DMSO-$d_6$) δ 8.22 (dd, J=5.75, 10.13 Hz, 1H), 7.88 (dd, J=5.94, 9.69 Hz, 1H), 4.77 (br s, 1H), 4.47-4.69 (m, 2H), 3.76 (q, J=6.96 Hz, 3H), 3.48-3.55 (m, 1H), 1.68 (br d, J=9.38 Hz, 2H), 1.50 (br d, J=7.00 Hz, 4H), 1.26 (t, J=7.19 Hz, 3H).

Step 6: Preparation of Compound 6-7

Compound 6-6 (2.96 g, 8.12 mmol, 1 eq) was dissolved in acetonitrile (30 mL), then (2S)-1,1,1-trifluoropropan-2-ol (1.39 g, 12.19 mmol, 1.5 eq) and potassium phosphate (3.45 g, 16.25 mmol, 2 eq) were added, and the reaction solution was stirred at 73° C. for 12 hours. The raw materials were completely reacted, and the reaction solution was quenched by adding water (30 mL) to the reaction solution, extracted by adding ethyl acetate (30 mL*5). The organic phases were combined, washed with saturated brine (30 mL*2), dried over anhydrous sodium sulfate, filtered, and the filtrate was concentrated under reduced pressure to the crude product of 6-7. MS ESI calculated for $C_{20}H_{22}F_4N_4O_4$ $[M+H]^+$ 459, found 459. $^1H$ NMR (400 MHz, DMSO-$d_6$) δ 8.08 (d, J=9.79 Hz, 1H), 7.75 (d, J=6.02 Hz, 1H), 5.44-5.53 (m, 1H), 4.79 (br s, 1H), 4.49-4.71 (m, 2H), 3.77-3.82 (m, 2H), 3.75 (br s, 1H), 3.51-3.56 (m, 1H), 1.70 (br d, J=8.78 Hz, 2H), 1.52 (br d, J=7.53 Hz, 4H), 1.48 (s, 3H), 1.28 (t, J=7.15 Hz, 3H).

Step 7: Preparation of Compound 6-8

Compound 6-7 (1 g, 2.18 mmol, 1 eq) was dissolved in dichloromethane (12 mL), and the reaction system was cooled down to −78° C. DIBAL-H (1 M, 6.54 mL, 3 eq) was added dropwise and stirred at −78° C. for 2 hours; hydrochloric acid (1 M, 10.91 mL, 5 eq) was added dropwise, slowly heated to 25° C. and continued to stir for 1 hour. The raw materials were completely reacted, and the reaction solution was quenched by adding saturated ammonium chloride aqueous solution (10 mL) to the reaction solution, and extracted by adding dichloromethane (10 mL*3). The organic phases were combined, washed with saturated brine (10 mL*3), dried over anhydrous sodium sulfate, filtered, and the filtrate was concentrated under reduced pressure to obtain the crude product of 6-8, which was directly fed to the next step without purification.

MS ESI calculated for $C_{15}H_{15}F_4N_3O_4$ $[M+H-84]^+$ 378, found 378.

Step 8: Preparation of Compound 6-9

Compound 6-8 (0.5 g, 1.08 mmol, 1 eq) was dissolved in methanol (8 mL), then 1-diazo-1-dimethoxyphosphonylpropan-2-one (312.27 mg, 1.63 mmol, 1.5 eq) and potassium carbonate (299.53 mg, 2.17 mmol, 2 eq) were added and stirred at 25° C. for 12 hours. The raw materials were completely reacted, and the reaction solution was concentrated under reduced pressure. Water (10 mL) was added, then ethyl acetate (10 mL*3) was added for extraction, and the organic phases were combined, washed with saturated brine (5 mL*3), dried over anhydrous sodium sulfate, filtered, and the filtrate was concentrated under reduced pressure. The crude product was purified by column chromatography (petroleum ether:ethyl acetate=1:0-3:1) to obtain 6-9. MS ESI calculated for $C_{21}H_{23}F_4N_3O_4$, $[M+H]^+$ 458, found 458.

Step 9: Preparation of Compound 6-10

Compound 6-9 (193 mg, 421.93 μmol, 1 eq) was dissolved in acetone (3 mL), then N-bromosuccinimide (112.65 mg, 632.90 μmol, 1.5 eq) and silver nitrate (7.17 mg, 42.19 μmol, 0.1 eq) were added and stirred at 25° C. for 1 hour. The raw materials were completely reacted, and the reaction solution was filtered, then the filtrate was collected and concentrated under reduced pressure to obtain the crude product of 6-10. MS ESI calculated for $C_{21}H_{22}BrF_4N_3O_4$, $[M+H]^+$ 538, found 538.

Step 10: Preparation of Compound 6-11

Compound 6-10 (200 mg, 372.92 μmol, 1 eq) was dissolved in acetonitrile (4 mL) and water (0.2 mL), then silver fluoride (189.25 mg, 1.49 mmol, 4 eq) was added and stirred at 80° C. for 12 hours. The raw materials were completely reacted, and the reaction solution was filtered, and water (5 mL) was added, then ethyl acetate (5 mL*3) was added for extraction. The organic phases were combined, washed with saturated brine (5 mL*3), dried over anhydrous sodium sulfate, filtered, and the filtrate was concentrated under reduced pressure. The crude product was purified by column chromatography (petroleum ether:ethyl acetate=1:0-2:1) to obtain compound 6-11. MS ESI calculated for $C_{21}H_{23}BrF_5N_3O_4$, $[M+H]^+$ 556, found 556. $^1H$ NMR (400 MHz, $CDCl_3$) δ 7.45 (d, J=11.29 Hz, 1H), 7.29 (s, 1H), 6.67-6.83 (m, 1H), 4.75-4.79 (m, 2H), 4.74 (s, 1H), 4.48 (d, J=12.80 Hz, 1H), 3.88-3.93 (m, 2H), 3.84-3.87 (m, 1H), 3.58-3.64 (m, 1H), 1.75-1.87 (m, 2H), 1.59-1.68 (m, 4H), 1.55 (s, 2H), 1.41 (t, J=7.28 Hz, 3H).

Step 11: Preparation of Compound 6-12

Compound 6-11 (43 mg, 77.29 μmol, 1 eq) was dissolved in a mixture of tetrahydrofuran (1 mL) and water (0.2 mL), then (2-methoxy-3-pyridyl)boronic acid (23.64 mg, 154.59 μmol, 2 eq), tetrakis(triphenylphosphine)palladium (8.93 mg, 7.73 μmol, 0.1 eq) and cesium carbonate (37.78 mg, 115.94 μmol, 1.5 eq) were added and stirred at 65° C. for 3 hours. The raw materials were completely reacted, and the reaction solution was filtered. Water (3 mL) was added, and ethyl acetate (3 mL*3) was added for extraction, and the organic phases were combined, washed with saturated brine (3 mL*3), dried over anhydrous sodium sulfate, filtered, and the filtrate was concentrated under reduced pressure to obtain the crude compound of 6-12. MS ESI calculated for $C_{27}H_{29}F_5N_4O_5$, $[M+H]^+$ 585, found 585.

Step 12: Preparation of Compound 6

Compound 6-12 (34 mg, 58.17 μmol, 1 eq) was dissolved in ethanol (1 mL), then phosphoric acid (336.00 mg, 3.43 mmol, 200 μL, 58.94 eq) was added and stirred at 65° C. for 1 hour. The raw materials were completely reacted, and the reaction solution was concentrated. Water (3 mL) was added, and ethyl acetate (3 mL*3) was added for extraction, and the organic phases were combined, washed with saturated brine (3 mL*3), dried over anhydrous sodium sulfate, filtered, and the filtrate was concentrated under reduced pressure. The crude product was purified by HPLC (Chromatographic column: Phenomenex Gemini-NX C18 75*30 mm*3 μm; mobile phase: [$H_2O$ (0.225% FA)-ACN]; ACN %: 45%-75%, 7 min) to obtain compound 6.

MS ESI calculated for $C_{22}H_{21}F_5N_4O_4$, $[M+H]^+$ 501, found 501. $^1H$ NMR (400 MHz, $CDCl_3$) δ 8.18 (br d, J=7.50 Hz, 1H), 8.06-8.12 (m, 1H), 7.53 (d, J=11.63 Hz, 1H), 7.30 (br d, J=6.00 Hz, 1H), 7.28 (d, J=44.00 Hz, 1H), 6.92-6.97 (m, 1H), 4.81 (td, J=5.96, 12.23 Hz, 1H), 4.68 (s, 2H), 4.00 (s, 3H), 3.92 (q, J=7.21 Hz, 3H), 1.61 (br s, 3H), 1.43 (br s, 3H).

Example 2: Synthesis of Compound 5

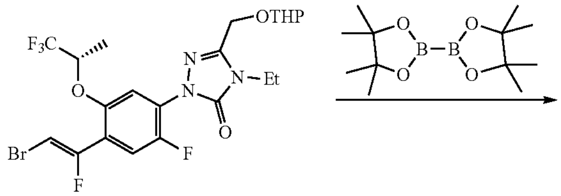

6-11

-continued

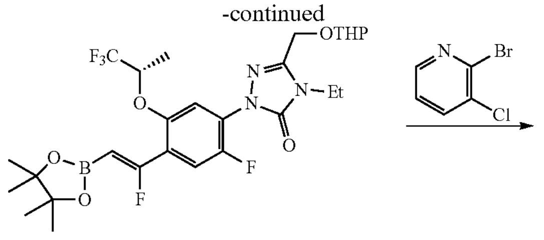

5-2

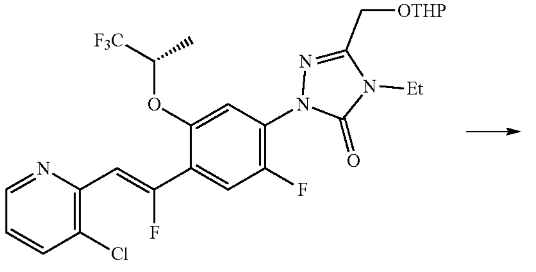

5-3

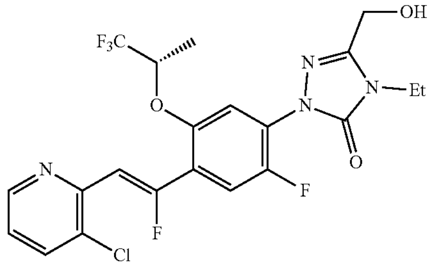

Compound 5

Step 1: Preparation of Compound 5-2

Compound 6-11 (105 mg, 188.74 μmol, 1 eq) and bis (pinacolato)diboron (95.86 mg, 377.48 μmol, 2 eq) were dissolved in dioxane (1.5 mL), then tris(dibenzylideneacetone)dipalladium (10.85 mg, 11.85 μmol, 6.28e-2 eq), tricyclohexylphosphine (21.17 mg, 75.50 μmol, 24.48 μL, 0.4 eq) and potassium acetate (74.09 mg, 754.96 μmol, 4 eq) were added and stirred at 90° C. for 16 hours. After the raw materials were completely reacted, the reaction was quenched by adding water (3 mL), extracted by adding ethyl acetate (30 mL*3), and the organic phases were combined, washed with saturated brine (3 mL*2), dried over anhydrous sodium sulfate, filtered, and the filtrate was concentrated under reduced pressure. The crude product was purified by column chromatography (petroleum ether:ethyl acetate=1: 0-3:1) to obtain the crude product of 5-2. MS ESI calculated for $C_{27}H_{35}BF_5N_3O_6$ $[M+H]^+$ 604, found 604; MS ESI calculated for borate MS: $C_{21}H_{25}BF_5N_3O_6$ $[M-82]^+$ 522, found 522.

Step 2: Preparation of Compound 5-3

Compound 5-2 (30 mg, 49.72 μmol, 1 eq) and 2-bromo-3-chloropyridine (14.35 mg, 74.58 μmol, 1.5 eq) were dissolved in a mixture of dioxane (0.5 mL) and water (0.1 mL), then [1,1-bis(diphenylphosphino)ferrocene]dichloropalladium (3.64 mg, 4.97 μmol, 0.1 eq) and potassium phosphate (21.11 mg, 99.44 μmol, 2 eq) were added and stirred at 100° C. for 3 hours. The raw materials were completely reacted, and the reaction was quenched by adding water (3 mL), extracted by adding ethyl acetate (3 mL*3). The organic phases were combined, washed with saturated brine (3 mL*2), dried over anhydrous sodium sulfate, filtered, and the filtrate was concentrated under reduced pressure. The crude product was purified by silica gel plate (petroleum ether:ethyl acetate=2:1) to obtain compound 5-3.

MS ESI calculated for $C_{26}H_{26}ClF_5N_4O_4$ $[M+H]^+$ 589, found 589.

Step 3: Preparation of Compound 5

Compound 5-3 (17 mg, 28.86 μmol, 1 eq) was dissolved in ethanol (0.5 mL), then phosphoric acid (168.00 mg, 1.71 mmol, 100 μL, 59.39 eq) was added and stirred at 60° C. for 1 hour. The raw materials were completely reacted, and the reaction solution was concentrated. Water (3 mL) was added, then ethyl acetate (3 mL*3) was added for extraction, and the organic phases were combined, washed with saturated brine (3 mL*3), dried over anhydrous sodium sulfate, filtered, and the filtrate was concentrated under reduced pressure. The crude product was purified by silica gel plate (petroleum ether:ethyl acetate=1:1) to obtain compound 5.

MS ESI calculated for $C_{21}H_{18}ClF_5N_4O_3$ $[M+H]^+$ 505, found 505. $^1$H NMR (400 MHz, $CDCl_3$) δ 8.62 (d, J=4.77 Hz, 1H), 7.75 (dd, J=1.51, 8.28 Hz, 1H), 7.63 (d, J=11.54 Hz, 1H), 7.39 (d, J=40.00 Hz, 1H), 7.37 (d, J=6.02 Hz, 1H), 7.19 (dd, J=4.64, 8.16 Hz, 1H), 4.83-4.91 (m, 1H), 4.69 (s, 2H), 3.93 (q, J=7.28 Hz, 2H), 1.63 (d, J=6.27 Hz, 3H), 1.43 (t, J=7.15 Hz, 3H).

Example 3: Synthesis of Compound 2

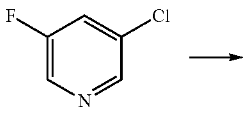

2-1

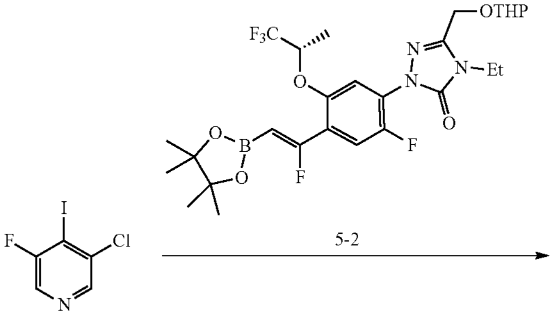

5-2

2-2

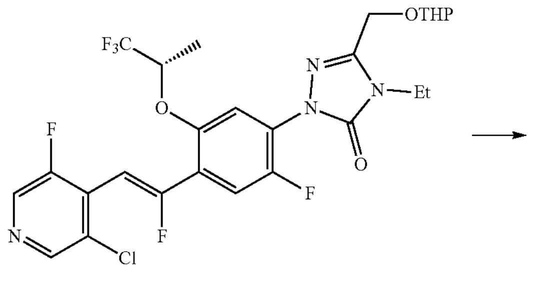

2-3

-continued

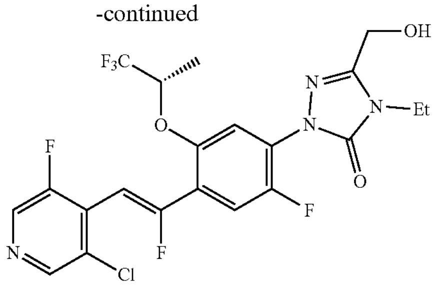

Compound 2

Step 1: Preparation of Compound 2-2

Compound 2-1 (200 mg, 1.52 mmol, 1 eq) was dissolved in tetrahydrofuran (3 mL) under nitrogen protection, and lithium diisopropylamide (2 M, 912.30 μL, 1.2 eq) was added slowly dropwise, and the reaction solution was stirred at −78° C. for 0.5 hours. A solution of iodine (578.88 mg, 2.28 mmol, 1.5 eq) in tetrahydrofuran (1 mL) was added at −78° C., and the reaction solution was slowly heated to 20° C. and stirred for 2 hours. The raw materials were completely reacted, and 1M dilute hydrochloric acid was added to the reaction solution to adjust the pH value to 7, and ethyl acetate (3 mL*3) was added for extraction, and the organic phases were combined, washed with saturated brine (3 mL*2), dried over anhydrous sodium sulfate, filtered, and the filtrate was concentrated under reduced pressure. The crude product was purified by column chromatography (petroleum ether:ethyl acetate=1:0-10:1) to obtain compound 2-2.

MS ESI calculated for $C_5H_2ClFIN$ $[M+H]^+$ 258, found 258. $^1H$ NMR (400 MHz, $CDCl_3$) δ 8.38 (s, 1H), 8.21 (s, 1H).

Step 2: Preparation of Compound 2-3

Intermediate 5-2 (10 mg, 16.57 μmol, 1 eq) and compound 2-2 (6.40 mg, 24.86 μmol, 1.5 eq) were dissolved in a mixture of dioxane (0.3 mL) and water (0.05 mL), then [1,1-bis(diphenylphosphino)ferrocene]dichloropalladium (1.21 mg, 1.66 μmol, 0.1 eq) and potassium phosphate (7.04 mg, 33.15 μmol, 2 eq) were added and stirred at 100° C. for 1 hour. The raw materials were completely reacted, and the reaction was quenched by adding water (1 mL); extracted by adding ethyl acetate (1 mL*3), and the organic phases were combined, washed with saturated brine (1 mL*2), dried over anhydrous sodium sulfate, filtered, and the filtrate was concentrated under reduced pressure. The crude product was purified by silica gel plate (petroleum ether:ethyl acetate=2:1) to obtain compound 2-3.

MS ESI calculated for $C_{26}H_{25}ClF_6N_4O_4$ $[M+H]^+$ 607, found 607.

Step 3: Preparation of Compound 2

Compound 2-3 (10 mg, 16.48 μmol, 1 eq) was dissolved in ethanol (0.5 mL), and phosphoric acid (168.00 mg, 1.71 mmol, 100 μL, 104.05 eq) was added and stirred at 60° C. for 1 hour. After the raw materials were completely reacted, the reaction solution was concentrated. Water (1 mL) was added, and ethyl acetate (1 mL*3) was added for extraction, and the organic phases were combined, washed with saturated brine (1 mL*3), dried over anhydrous sodium sulfate, filtered, and the filtrate was concentrated under reduced pressure. The crude product was purified by silica gel plate (petroleum ether:ethyl acetate=1:1) to obtain compound 2.

MS ESI calculated for $C_{21}H_{17}ClF_6N_4O_3$, $[M+H]^+$ 523, found 523. $^1H$ NMR (400 MHz, $CDCl_3$) δ 8.48 (s, 1H), 8.43 (s, 1H), 7.58 (d, J=11.54 Hz, 1H), 7.40 (br d, J=6.02 Hz, 1H), 6.86 (br d, J=40.00 Hz, 1H), 4.86 (td, J=6.27, 12.55 Hz, 1H), 4.69 (br d, J=5.02 Hz, 2H), 3.92 (br d, J=7.03 Hz, 2H), 1.63 (br s, 3H), 1.41-1.46 (m, 4H).

Example 4: Synthesis of Compound 21

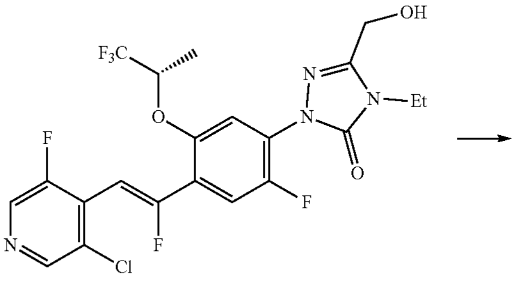

Compound 2

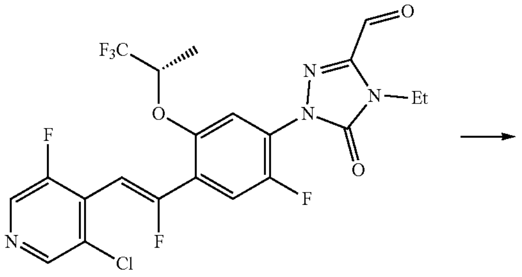

21-1

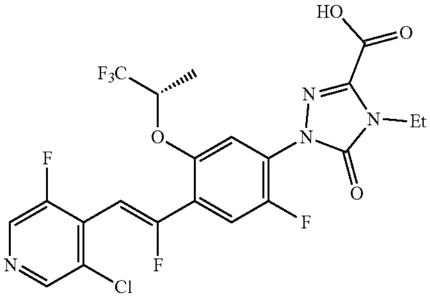

Compound 21

Step 1: Preparation of Compound 21-1

Compound 2 (18 mg, 34.43 μmol, 1 eq) was dissolved in dichloromethane (0.5 mL), then Dess-Martine periodinane (43.81 mg, 103.28 μmol, 31.98 μL, 3 eq) was added and stirred at 25° C. for 16 hours. The raw materials were completely reacted, and saturated sodium thiosulfate solution (2 mL) was added to the reaction solution and stirred for 5 min; dichloromethane (2 mL*3) was added for extraction, and the organic phases were combined, washed with saturated brine (2 mL*3), dried over anhydrous sodium sulfate, filtered, and the filtrate was concentrated under reduced pressure. The crude product was purified by silica gel plate (petroleum ether:ethyl acetate=2:1) to obtain compound 21-1.

MS ESI calculated for $C_{21}H_{15}ClF_6N_4O_3$ $[M+H]^+$ 521, found 521.

Step 2: Preparation of Compound 21

Compound 21-1 (15 mg, 28.80 μmol, 1 eq) and 2-methyl-2-butene (19.86 mg, 283.18 μmol, 30.00 μL, 9.83 eq) were dissolved in tert-butanol (0.6 mL), then a solution of sodium chlorite (26.05 mg, 288.01 μmol, 10 eq) and sodium dihydrogen phosphate (44.93 mg, 288.01 μmol, 10 eq) in water (0.25 mL) was added and stirred at 25° C. for 12 hours. The raw materials were completely reacted, and the reaction solution was filtered and concentrated, and the crude product was purified by silica gel plate (dichloromethane:methanol=10:1) to obtain compound 21.

MS ESI calculated for $C_{21}H_{15}ClF_6N_4O_4$ $[M+H]^+$ 537, found 537.

$^1$H NMR (400 MHz, $CDCl_3$) δ 8.52 (s, 1H), 8.49 (s, 1H), 7.63 (d, J=10.79 Hz, 1H), 7.59 (br d, J=5.52 Hz, 1H), 6.99-6.89 (d, J=40.0 Hz, 1H), 5.32 (td, J=6.27, 12.55 Hz, 1H), 4.20 (q, J=7.03 Hz, 2H), 1.60 (d, J=6.27 Hz, 3H), 1.33-1.36 (m, 3H).

Example 5: Synthesis of Compound 22

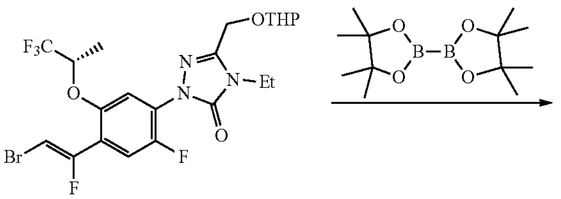

6-11

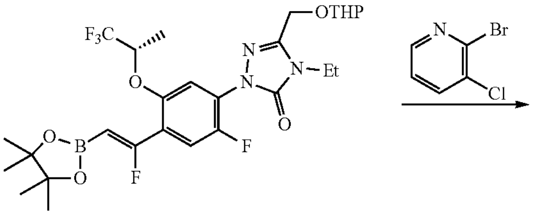

5-2

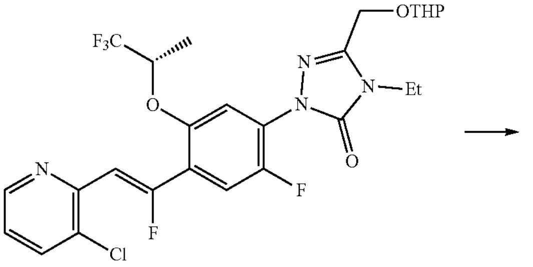

5-3

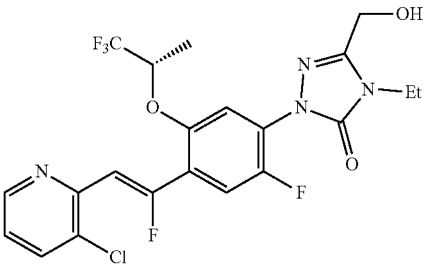

Compound 5

Step 1: Preparation of Compound 22-1

Methyltriphenylphosphonium bromide (58.07 mg, 162.55 μmol, 1.5 eq) was added to a solution of n-butyllithium (2.5 M, 65.02 μL, 1.5 eq) in tetrahydrofuran (1 mL) at −78° C. and stirred for 0.5 hours. A solution of compound 6-8 (50 mg, 108.36 μmol, 1 eq) in tetrahydrofuran (0.5 mL) was added and stirred for 0.5 hours; heated to 40° C. and continued to stir for 15 hours. The raw materials were completely reacted, quenched by adding saturated ammonium chloride solution (2 mL), extracted by adding ethyl acetate (2 mL*3), and the organic phases were combined, washed with saturated brine (2 mL*2), dried over anhydrous sodium sulfate, filtered, and the filtrate was concentrated under reduced pressure. The crude product was purified by silica gel plate (petroleum ether:ethyl acetate=2:1) to obtain compound 22-1.

MS ESI calculated for $C_{21}H_{25}F_4N_3O_4$ $[M+H]^+$ 460, found 460.

Step 2: Preparation of Compound 22-2

Compound 22-1 (27 mg, 58.77 μmol, 1 eq) and 2-bromo-3-chloropyridine (22.62 mg, 117.54 μmol, 2 eq) were dissolved in N,N-dimethylformamide (0.5 mL), then triphenylphosphine (3.08 mg, 11.75 μmol, 0.2 eq), triethylamine (17.84 mg, 176.30 μmol, 24.54 μL, 3 eq) and palladium acetate (1.32 mg, 5.88 μmol, 0.1 eq) were added, and the atmosphere was replaced three times with nitrogen, and the reaction was stirred at 120° C. for 18 hours. The raw materials were completely reacted, quenched by adding water (2 mL) to the reaction solution, filtered, and the filtrate was collected; extracted by adding ethyl acetate (2 mL*3), and the organic phases were combined, washed with saturated brine (2 mL*3), dried over anhydrous sodium sulfate, filtered, and the filtrate was concentrated under reduced pressure. The crude product was purified by silica gel plate (petroleum ether:ethyl acetate=2:1) to obtain compound 22-2.

Step 3: Preparation of Compound 2

Compound 22-2 (11 mg, 19.27 μmol, 1 eq) was dissolved in ethanol (0.5 mL), and phosphoric acid (168.00 mg, 1.71 mmol, 0.1 mL, 88.99 eq) was added and stirred at 60° C. for 1 hour. After the raw materials were completely reacted, the reaction solution was concentrated. Water (1 mL) was added, and ethyl acetate (1 mL*3) was added for extraction, and the organic phases were combined, washed with saturated brine (1 mL*3), dried over anhydrous sodium sulfate, filtered, and the filtrate was concentrated under reduced pressure. The crude product was purified by silica gel plate (petroleum ether:ethyl acetate=1:1) to obtain compound 22.

MS ESI calculated for $C_{21}H_{19}ClF_4N_4O_3$, $[M+H]^+$ 487, found 487.

$^1$H NMR (400 MHz, $CDCl_3$) δ 8.37 (dd, J=1.38, 4.64 Hz, 1H), 7.69 (dd, J=1.51, 8.03 Hz, 1H), 7.11-7.16 (m, 2H), 6.96-6.93 (m, 3H), 4.60-4.67 (m, 3H), 3.86-3.92 (m, 2H), 2.24 (br s, 1H), 1.48 (d, J=6.53 Hz, 3H), 1.38-1.44 (m, 3H).

Example 6: Synthesis of Compound 23

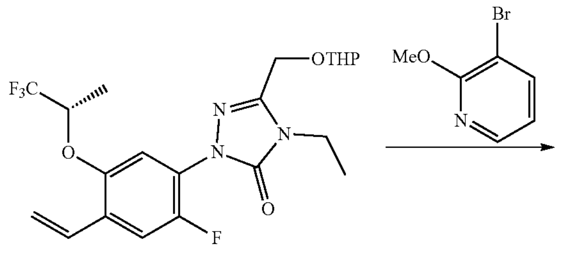

22-1

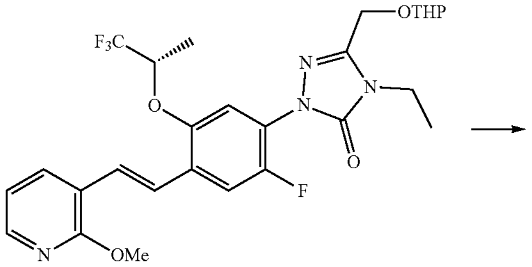

23-1

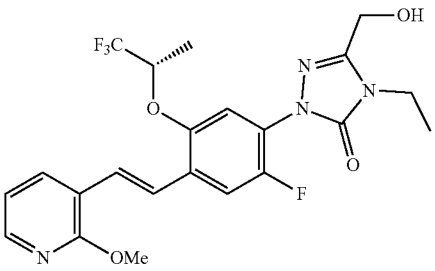

Compound 23

Step 1: Preparation of Compound 23-1

Compound 22-1 (30 mg, 65.30 μmol, 1 eq) and 3-bromo-2-methoxypyridine (24.55 mg, 130.60 μmol, 2 eq) were dissolved in N,N-dimethylformamide (0.5 mL), then triphenylphosphine (3.43 mg, 13.06 μmol, 0.2 eq), potassium carbonate (27.07 mg, 195.89 μmol, 3 eq) and palladium acetate (1.47 mg, 6.53 μmol, 0.1 eq) were added, and the atmosphere was replaced three times with nitrogen, and the reaction was stirred at 120° C. for 12 hours. The raw materials were completely reacted, quenched by adding water (4 mL), filtered, and the filter cake was washed with ethyl acetate (2 mL*3). The filtrate was collected, separated, and the organic phases were combined, washed with saturated brine (2 mL*3), dried over anhydrous sodium sulfate, filtered, and the filtrate was concentrated under reduced pressure. The crude product was purified by silica gel plate (petroleum ether:ethyl acetate=2:1) to obtain compound 23-1.

MS ESI calculated for $C_{27}H_{30}F_4N_4O_5$ $[M+H]^+$ 567, found 567.

Step 2: Preparation of Compound 23

Compound 23-1 (14 mg, 24.71 μmol, 1 eq) was dissolved in ethanol (0.5 mL), then phosphoric acid (215.50 mg, 2.20 mmol, 128.27 μL, 88.99 eq) was added and stirred at 60° C. for 1 hour. After the raw materials were completely reacted, the reaction solution was concentrated. Water (1 mL) was added, and ethyl acetate (1 mL*3) was added for extraction, and the organic phases were combined, washed with saturated brine (1 mL*3), dried over anhydrous sodium sulfate, filtered, and the filtrate was concentrated under reduced pressure. The crude product was purified by silica gel plate (petroleum ether:ethyl acetate=1:1) to obtain compound 23.

MS ESI calculated for $C_{22}H_{22}F_4N_4O_4$, $[M+H]^+$ 483, found 483.

$^1H$ NMR (400 MHz, $CDCl_3$) δ 8.10 (dd, J=1.76, 4.77 Hz, 1H), 7.79 (dd, J=1.76, 7.53 Hz, 1H), 7.52 (s, 1H), 7.49 (d, J=4.27 Hz, 1H), 7.30-7.26 (br d, J=16 Hz, 1H), 7.18 (d, J=6.27 Hz, 1H), 6.90-6.96 (m, 1H), 4.65 (s, 2H), 4.61-4.64 (m, 1H), 4.04 (s, 3H), 3.90 (q, J=7.11 Hz, 2H), 1.55 (d, J=6.53 Hz, 3H), 1.39-1.43 (m, 3H).

Example 7: Synthesis of Compound 24

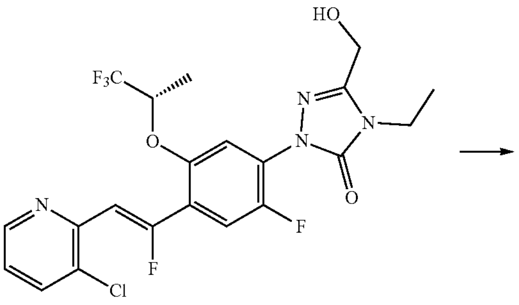

Compound 5

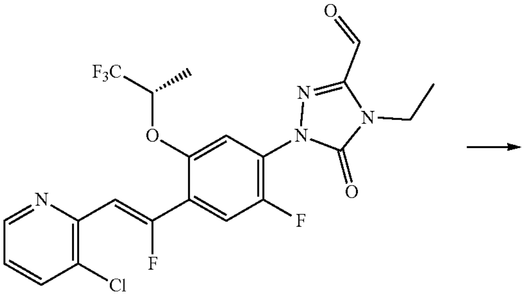

24-1

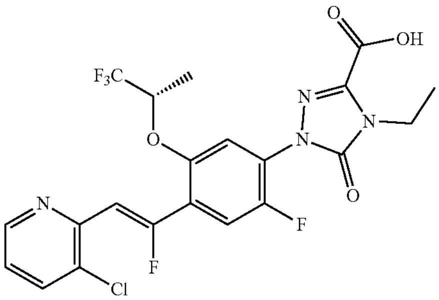

Compound 24

Step 1: Preparation of Compound 24-1

Compound 5 (30 mg, 59.43 μmol, 1 eq) was dissolved in dichloromethane (1 mL), then Dess-Martine periodinane (50.41 mg, 118.85 μmol, 36.80 μL, 2 eq) was added, and the reaction solution was stirred at 25° C. for 12 hours. The raw materials were completely reacted, and saturated sodium thiosulfate solution (2 mL) was added to the reaction solution and stirred for 5 min; saturated sodium bicarbonate solution (1 mL) was added, extracted with dichloromethane (5 mL×3), and the organic phases were combined, washed with saturated brine (5 mL), dried over anhydrous sodium sulfate, filtered, and the filtrate was concentrated to dryness under reduced pressure to obtain compound 24-1. MS ESI calculated for $C_{21}H_{16}ClF_5N_4O_3$ $[M+H]^+$ 503, found 503.

Step 2: Preparation of Compound 24

Compound 24-1 (29.2 mg, 58.07 μmol, 1 eq) and 2-methyl-2-butene (39.72 mg, 566.35 μmol, 60.00 μL, 9.75 eq) were dissolved in tert-butanol (1 mL), then a solution of sodium chlorite (52.52 mg, 580.72 μmol, 10 eq) and sodium dihydrogen phosphate (69.67 mg, 580.72 μmol, 10 eq) in water (0.4 mL) was added and the reaction solution was stirred at 25° C. for 12 hours. The raw materials were completely reacted, and the reaction solution was filtered and concentrated, and the crude product was purified by silica gel plate (dichloromethane:methanol=8:1) to obtain compound 24.

MS ESI calculated for $C_{21}H_{16}ClF_5N_4O_4$ $[M+H]^+$ 519, found 519.

$^1H$ NMR (400 MHz, $CD_3OD$) δ 8.54 (d, J=4.77 Hz, 1H), 7.93 (d, J=8.03 Hz, 1H), 7.65 (d, J=11.04 Hz, 1H), 7.57 (d, J=5.77 Hz, 1H), 7.41-7.31 (br d, J=40.00 Hz, 1H), 7.35 (dd, J=4.77, 8.28 Hz, 1H), 5.31 (td, J=6.27, 12.55 Hz, 1H), 4.20 (q, J=7.03 Hz, 2H), 1.60 (d, J=6.27 Hz, 3H), 1.35 (t, J=7.03 Hz, 3H).

Example 8: Synthesis of Compound 25

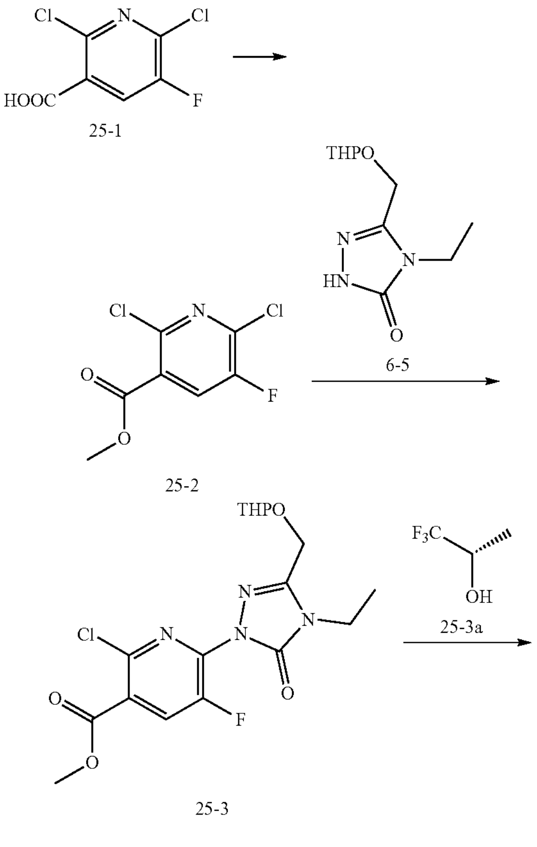

-continued

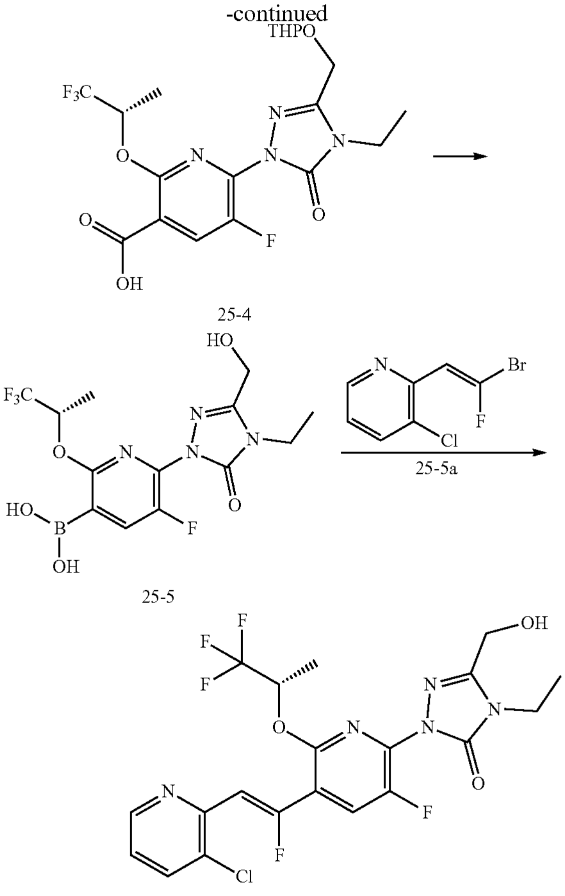

Compound 25

Step 1: Preparation of Compound 25-2

Compound 25-1 (0.5 g, 2.38 mmol, 1 eq) was dissolved in tetrahydrofuran (5 mL) at 0° C., then oxalyl chloride (604.44 mg, 4.76 mmol, 416.85 μL, 2 eq) was added, and N,N-dimethylformamide (0.05 mL) was added dropwise and stirred at 0° C. for 2 hours. Methanol (5 mL) was added and continued to stir for 0.5 hours. The raw materials were completely reacted, and the reaction solution was concentrated; water (5 mL) was added, ethyl acetate (5 mL*3) was added for extraction, and the organic phases were combined, washed with saturated brine (5 mL*3), dried over anhydrous sodium sulfate, filtered, and the filtrate was concentrated under reduced pressure. The crude product was purified by column chromatography (petroleum ether:ethyl acetate=1:0-10:1) to obtain compound 25-2.

MS ESI calculated for $C_7H_4Cl_2FNO_2$ $[M+H]^+$ 224, found 224.

Step 2: Preparation of Compound 25-3

Compound 25-2 (0.1 g, 446.39 μmol, 1 eq) and compound 6-5 (121.74 mg, 535.67 μmol, 1.2 eq) were dissolved in dimethyl sulfoxide (1 mL), and potassium carbonate (92.54 mg, 669.59 μmol, 1.5 eq) was added and stirred for 3 hours at 80° C. The raw materials were completely reacted, quenched by adding water (5 mL), extracted by adding ethyl acetate (5 mL*3), and the organic phases were combined, washed with saturated brine (5 mL*2), dried over anhydrous sodium sulfate, filtered, and the filtrate was concentrated under reduced pressure. The crude product was purified by column chromatography (petroleum ether:ethyl acetate=1: 0-100:5) to obtain compound 25-3.

MS ESI calculated for $C_{17}H_{20}ClFN_4O_5$ $[M+H]^+$ 415, found 415.

$^1H$ NMR (400 MHz, $CDCl_3$) δ 8.15 (d, J=8.78 Hz, 1H), 4.71-4.77 (m, 2H), 4.50 (d, J=12.80 Hz, 1H), 3.99 (s, 3H), 3.83-3.91 (m, 3H), 3.56-3.65 (m, 1H), 1.73-1.87 (m, 2H), 1.60-1.68 (m, 4H), 1.39 (t, J=7.15 Hz, 3H).

Step 3: Preparation of Compound 25-4

Potassium bis(trimethylsilyl)amide (1 M, 501.43 μL, 1.3 eq) was added dropwise to a solution of compound 25-3a (52.80 mg, 462.86 μmol, 1.2 eq) in tetrahydrofuran (1.5 mL) at −10° C. under nitrogen protection and stirred for 0.5 hours; a solution of compound 25-3 (160 mg, 385.71 μmol, 1 eq) in tetrahydrofuran (05 mL) was added and continued to stir at −10° C. under nitrogen protection for 4 hours. The raw materials were completely reacted, quenched by adding hydrochloric acid aqueous (1 M, 10 mL), extracted by adding ethyl acetate (5 mL*3), and the organic phases were combined, washed with saturated brine (5 mL*3), dried over anhydrous sodium sulfate, filtered and the filtrate was concentrated under reduced pressure to obtain the crude product of 25-4.

MS ESI calculated for $C_{19}H_{22}F_4N_4O_6$ $[M+H]^+$ 479, found 479.

Step 4: Preparation of Compound 25-5

Compound 25-4 (110 mg, 229.94 μmol, 1 eq) and bis (pinacolato)diboron (116.78 mg, 459.87 μmol, 2 eq) were dissolved in dioxane (2 mL), then 1,4-bis(diphenylphosphino)butane (19.61 mg, 45.99 μmol, 0.2 eq), triethylamine (34.90 mg, 344.90 μmol, 48.01 μL, 1.5 eq) and pivalic anhydride (64.24 mg, 344.90 μmol, 69.98 μL, 1.5 eq) were added, and the atmosphere was replaced three times with nitrogen. $Pd(OAc)_2$ (5.16 mg, 22.99 μmol, 0.1 eq) was added, and the atmosphere was replaced three times with nitrogen, and the reaction was stirred at 145° C. for 16 hours. The raw materials were completely reacted, and the reaction solution was quenched by adding water (4 mL), filtered, and the filter cake was washed with ethyl acetate (2 mL*3), and the filtrate was collected, separated, and the organic phases were combined, washed with saturated brine (2 mL*3), dried over anhydrous sodium sulfate, filtered, and the filtrate was concentrated under reduced pressure to obtain compound 25-5.

MS ESI calculated for $C_{13}H_{15}BF_4N_4O_5$ $[M+H]^+$ 395, found 395.

Step 5: Preparation of Compound 25

Compound 25-5 (50 mg, 126.88 μmol, 1 eq) and compound 25-5a (36.00 mg, 152.25 μmol, 1.2 eq) were dissolved in dioxane (1 mL) and water (0.2 mL), and cesium carbonate (82.68 mg, 253.75 μmol, 2 eq) was added, and the atmosphere was replaced three times with nitrogen; [1,1-bis (diphenylphosphino)ferrocene]dichloropalladium (9.28 mg, 12.69 μmol, 0.1 eq) was added, and the atmosphere was replaced three times with nitrogen, and the reaction was stirred at 100° C. for 2 hours. The raw materials were completely reacted, and the reaction solution was filtered; water (2 mL) was added, and ethyl acetate (2 mL*3) was added for extraction, and the organic phases were combined, washed with saturated brine (2 mL*3), dried over anhydrous sodium sulfate, filtered, and the filtrate was concentrated under reduced pressure. The reaction solution was concentrated. The crude product was purified by silica gel plate (petroleum ether:ethyl acetate=1:1) to obtain compound 25.

MS ESI calculated for $C_{20}H_{17}ClF_5N_5O_3$, $[M+H]^+$ 506, found 506.

$^1H$ NMR (400 MHz, $CDCl_3$) δ 8.62 (d, J=4.52 Hz, 1H), 7.99 (d, J=9.54 Hz, 1H), 7.75 (dd, J=1.51, 8.28 Hz, 1H), 7.63-7.53 (br d, J=40 Hz, 1H), 7.19 (dd, J=4.52, 8.03 Hz, 1H), 5.87 (td, J=6.53, 13.05 Hz, 1H), 4.68 (br s, 2H), 3.91 (q, J=7.11 Hz, 2H), 2.74 (br s, 1H), 1.63 (d, J=6.53 Hz, 3H), 1.42 (t, J=7.28 Hz, 3H).

Example 9: Synthesis of Compound 26

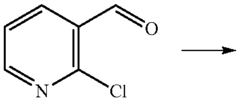

26-1

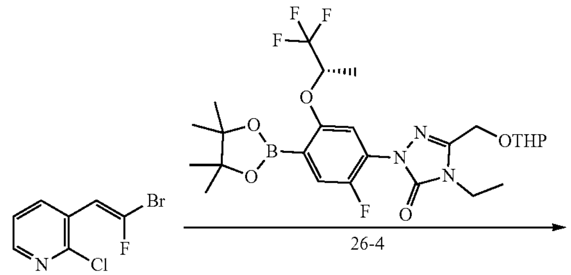

26-4

26-2

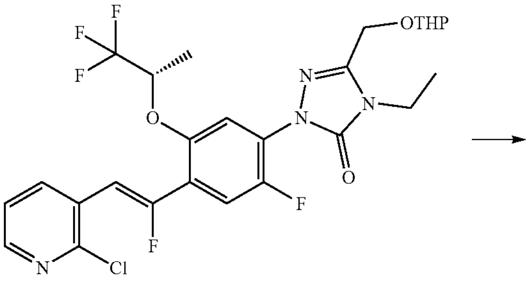

26-5

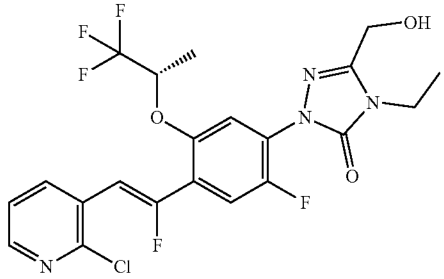

Compound 26

-continued

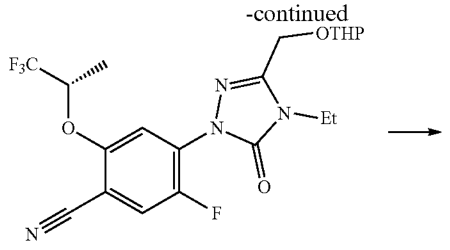

6-7

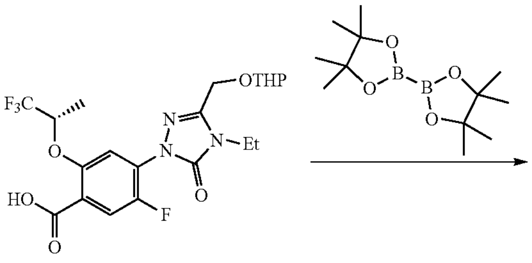

26-3

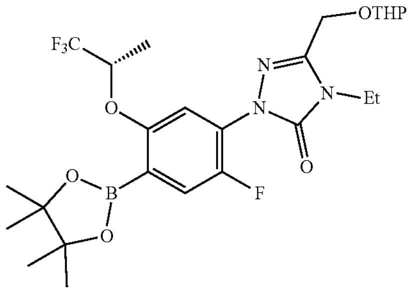

26-4

Step 1: Preparation of Compound 26-2

Compound 26-1 (300 mg, 2.12 mmol, 1 eq) was dissolved in ethanol (4.5 mL) at 0° C., then hydrazine hydrate (374.30 mg, 6.36 mmol, 363.40 μL, content of 85%, 3 eq) was added and the reaction solution was stirred at 25° C. for 2 hours. Ethylenediamine (381.97 mg, 6.36 mmol, 425.35 μL, 3 eq) and cuprous chloride (20.97 mg, 211.93 μmol, 0.1 eq) were added and stirred at 0° C. for 10 min, then tribromofluoromethane (1.43 g, 5.30 mmol, 2.5 eq) was added and the reaction solution was stirred at 25° C. for 1 hour. The raw materials were completely reacted, quenched by adding water (10 mL) to the reaction solution, extracted by adding ethyl acetate (10 mL×2), and the organic phases were combined, washed with saturated brine (10 mL), dried over anhydrous sodium sulfate, filtered, and the filtrate was concentrated to dryness under reduced pressure to obtain the crude product. The crude product was purified by fast silica gel column (0 to 15% ethyl acetate/petroleum ether) to obtain compound 26-2.

MS ESI calculated for $C_7H_4BrClFN$ $[M+H]^+$ 238, found 238.

$^1H$ NMR (400 MHz, $CDCl_3$) δ 8.32 (br s, 1H), 8.01 (d, J=7.53 Hz, 1H), 7.27-7.31 (m, 1H), 6.32-6.47 (m, 1H).

Step 2: Preparation of Compound 26-3

Compound 6-7 (2 g, 4.36 mmol, 1 eq) was dissolved in ethanol (20 mL), and sodium hydroxide (2 M, 6.54 mL, 3 eq) was added, and the reaction solution was stirred at 70° C. for 12 hours. After the raw materials were completely reacted, the reaction solution was concentrated under reduced pressure, diluted by adding water (10 mL), washed with methyl tert-butyl ether (10 mL×2) to remove impurities. The aqueous phase was adjusted to pH=6 with 1 M dilute hydrochloric acid, extracted with ethyl acetate (20 mL×3), and the organic phases were combined, washed with saturated brine (20 mL), dried over anhydrous sodium sulfate, filtered, and the filtrate was concentrated to dryness under reduced pressure to obtain the product. Compound 26-3 was obtained.

MS ESI calculated for $C_{20}H_{23}F_4N_3O_6$ $[M+H]^+$ 478, found 478.

Step 3: Preparation of Compound 26-4

Compound 26-3 (500 mg, 1.05 mmol, 1 eq) and bis(pinacolato)diboron (531.91 mg, 2.09 mmol, 2 eq) were dissolved in dioxane (10 mL), then palladium acetate (23.51 mg, 104.73 μmol, 0.1 eq), 1,4-bis(diphenylphosphino)butane (89.33 mg, 209.47 μmol, 0.2 eq), triethylamine (158.97 mg, 1.57 mmol, 218.66 uL, 1.5 eq) and pivalic anhydride (292.59 mg, 1.57 mmol, 318.73 μL, 1.5 eq) were added and the reaction solution was stirred at 145° C. under nitrogen protection for 12 hours. After the raw materials were completely reacted, the reaction solution was cooled down to 25° C., diluted by adding ethyl acetate (10 mL) to the reaction solution, filtered, and the filtrate was washed with water (10 mL×2) and saturated brine (10 mL), dried over anhydrous sodium sulfate, filtered, and the filtrate was concentrated to dryness under reduced pressure to obtain the crude product. The crude product was purified by fast silica gel column (0 to 50% ethyl acetate/petroleum ether) to obtain compound 26-4.

MS ESI calculated for $C_{25}H_{34}BF_4N_3O_6$ $[M+H]^+$ 560, found 560.

Step 4: Preparation of Compound 26-5

Compound 26-4 (100 mg, 178.78 μmol, 1 eq) and compound 26-2 (84.55 mg, 357.55 μmol, 2 eq) were dissolved in dioxane (2 mL) and water (0.4 mL), then [1,1-bis(diphenylphosphino)ferrocene]dichloropalladium (26.16 mg, 35.76 μmol, 0.2 eq) and cesium carbonate (233.00 mg, 715.11 μmol, 4 eq) were added, and the reaction solution was stirred at 100° C. under nitrogen protection for 2 hours. After the raw materials were completely reacted, the reaction solution was cooled down to 25° C., diluted by adding ethyl acetate (5 mL), filtered, and the filtrate was washed with water (5 mL×2) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:1) to obtain compound 26-5.

MS ESI calculated for $C_{26}H_{26}ClF_5N_4O_4$ $[M+H]^+$ 589, found 589.

$^1H$ NMR (400 MHz, $CDCl_3$) δ 8.29-8.33 (m, 1H), 8.28 (d, J=7.53 Hz, 1H), 7.54 (d, J=11.54 Hz, 1H), 7.35 (d, J=6.02 Hz, 1H), 7.28-7.32 (m, 1H), 7.19-7.29 (br d, J=40 Hz, 1H), 4.85 (td, J=5.87, 12.11 Hz, 1H), 4.77 (br s, 1H), 4.69-4.76 (m, 1H), 4.50 (d, J=12.80 Hz, 1H), 3.85-3.94 (m, 3H), 3.58-3.66 (m, 1H), 1.75-1.90 (m, 2H), 1.66 (br s, 1H), 1.63 (br d, J=6.53 Hz, 3H), 1.56-1.61 (m, 3H), 1.43 (t, J=7.03 Hz, 3H).

Step 5: Preparation of Compound 26

Compound 26-5 (52 mg, 88.29 μmol, 1 eq) was dissolved in ethanol (1 mL), then phosphoric acid (336.00 mg, 3.43 mmol, 0.2 mL, 38.83 eq) was added, and the reaction solution was stirred at 60° C. for 1 hour. After the raw materials were completely reacted, the reaction solution was cooled down to 25° C., and ethyl acetate (10 mL) was added to the reaction solution, and the organic phase was washed with water (5 mL×3) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:2) to obtain compound 26.

MS ESI calculated for $C_{21}H_{18}ClF_5N_4O_3$ $[M+H]^+$ 505, found 505.

$^1$H NMR (400 MHz, $CDCl_3$) δ 8.30 (br d, J=4.77 Hz, 1H), 8.28 (d, J=8.03 Hz, 1H), 7.55 (d, J=11.54 Hz, 1H), 7.36 (d, J=5.77 Hz, 1H), 7.28-7.32 (m, 1H), 7.19-7.28 (br d, J=44 Hz, 1H), 4.85 (td, J=6.24, 12.36 Hz, 1H), 4.69 (s, 2H), 3.92 (q, J=7.19 Hz, 2H), 1.63 (d, J=6.27 Hz, 3H), 1.43 (t, J=7.28 Hz, 3H).

Example 10: Synthesis of Compound 27

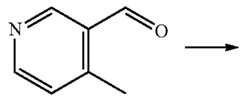

27-1

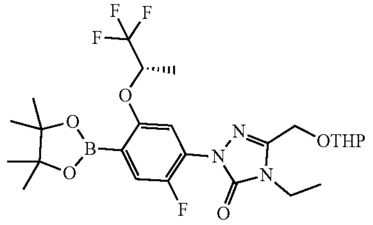

26-4

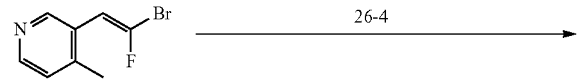

27-2

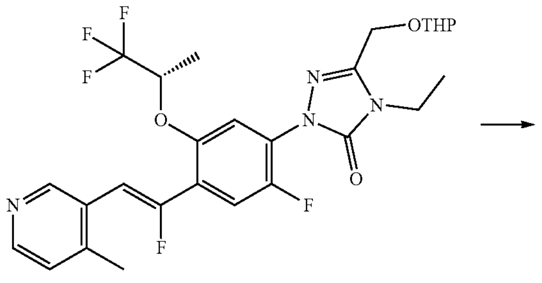

27-3

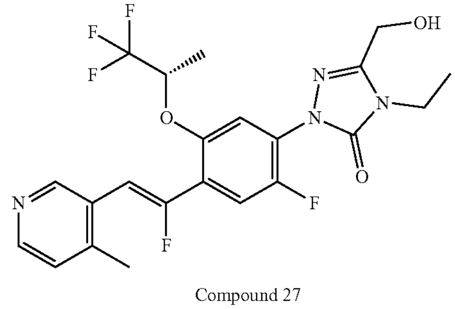

Compound 27

Step 1: Preparation of Compound 27-2

Compound 27-1 (300 mg, 2.48 mmol, 1 eq) was dissolved in ethanol (4.5 mL) at 0° C., then hydrazine hydrate (437.56 mg, 7.43 mmol, 424.82 μL, content of 85%, 3 eq) was added and the reaction solution was stirred at 25° C. for 2 hours; ethylenediamine (446.52 mg, 7.43 mmol, 497.24 μL, 3 eq) and cuprous chloride (24.52 mg, 247.65 μmol, 0.1 eq) were added and stirred at 0° C. for 10 min. Tribromofluoromethane (1.68 g, 6.19 mmol, 2.5 eq) was added and the reaction solution was stirred at 25° C. for 1 hour. After the raw materials were completely reacted, the reaction was quenched by adding water (10 mL) to the reaction solution, extracted by adding ethyl acetate (10 mL×2), and the organic phases were combined, washed with saturated brine (10 mL), dried over anhydrous sodium sulfate, filtered, and the filtrate was concentrated to dryness under reduced pressure to obtain the crude product. The crude product was purified by fast silica gel column (0 to 30% ethyl acetate/petroleum ether) to obtain 27-2.

MS ESI calculated for $C_8H_7BrFN$ $[M+H]^+$ 216, found 216.

$^1$H NMR (400 MHz, $CDCl_3$) δ 8.72 (s, 1H), 8.41 (d, J=5.13 Hz, 1H), 7.23 (d, J=5.00 Hz, 1H), 6.04-6.16 (m, 1H), 2.38 (s, 3H).

Step 2: Preparation of Compound 27-3

Compound 26-4 (100 mg, 178.78 μmol, 1 eq) and compound 27-2 (77.25 mg, 357.56 μmol, 2 eq) were dissolved in dioxane (2 mL) and water (0.4 mL), then [1,1-bis(diphenylphosphino)ferrocene]dichloropalladium (26.16 mg, 35.76 μmol, 0.2 eq) and cesium carbonate (233.00 mg, 715.12 μmol, 4 eq) were added, and the reaction solution was stirred at 100° C. under nitrogen protection for 2 hours. After the raw materials were completely reacted, the reaction solution was cooled down to 25° C., diluted by adding ethyl acetate (5 mL), filtered, and the filtrate was washed with water (5 mL×2) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:2) to obtain compound 27-3.

MS ESI calculated for $C_{27}H_{29}F_5N_4O_4[M+H]^+$ 569, found 569.

Step 3: Preparation of Compound 27

Compound 27-3 (50.20 mg, 88.29 μmol, 1 eq) was dissolved in ethanol (1 mL), then phosphoric acid (336.00 mg, 3.43 mmol, 0.2 mL, 38.83 eq) was added and the reaction solution was stirred at 60° C. for 1 hour. After the raw materials were completely reacted, the reaction solution was cooled down to 25° C., and ethyl acetate (10 mL) was added to the reaction solution, then the organic phase was washed with water (5 mL×3) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=0:1) to obtain compound 27.

MS ESI calculated for $C_{22}H_{21}F_5N_4O_3[M+H]^+$ 485, found 485.

$^1$H NMR (400 MHz, $CDCl_3$) δ 8.93 (s, 1H), 8.36 (br d, J=5.27 Hz, 1H), 7.38-7.44 (m, 2H), 7.35 (br d, J=4.77 Hz, 1H), 6.87-7.00 (m, 1H), 4.87 (quin, J=6.15 Hz, 1H), 4.69 (s, 2H), 3.94 (q, J=7.03 Hz, 2H), 2.45 (s, 3H), 1.61 (d, J=6.27 Hz, 3H), 1.43 (t, J=7.15 Hz, 3H).

Example 11: Synthesis of Compound 28

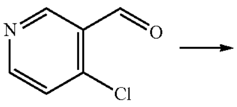

28-1

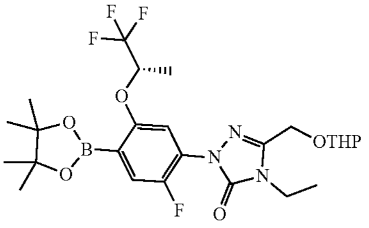

26-4

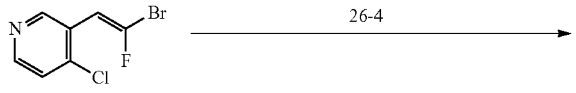

28-2

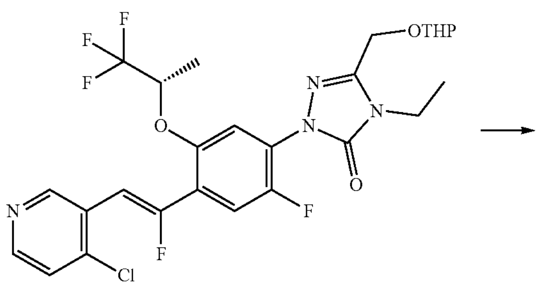

28-3

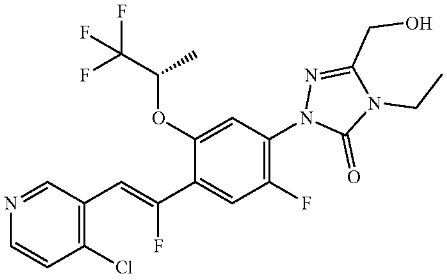

Compound 28

Step 1: Preparation of Compound 28-2

Compound 28-1 (300 mg, 2.12 mmol, 1 eq) was dissolved in ethanol (4.5 mL) at 0° C. Hydrazine hydrate (374.30 mg, 6.36 mmol, 363.40 μL, concentration of 85%, 3 eq) was added and the reaction solution was stirred at 25° C. for 2 hours. Ethylenediamine (381.97 mg, 6.36 mmol, 425.35 μL, 3 eq) and cuprous chloride (20.97 mg, 211.93 μmol, 5.07 μL, 0.1 eq) were added and stirred at 0° C. for 10 min, and tribromofluoromethane (1.43 g, 5.30 mmol, 2.5 eq) was added and the reaction solution was stirred at 25° C. for 1 hour. The raw materials were completely reacted, quenched by adding water (10 mL) to the reaction solution, extracted by adding ethyl acetate (10 mL×2), and the organic phases were combined and washed with saturated brine (10 mL), dried with anhydrous sodium sulfate, filtered, and the filtrate was concentrated to dryness under reduced pressure to obtain the crude product. The crude product was purified by fast silica gel column (0 to 15% ethyl acetate/petroleum ether) to obtain compound 28-2.

MS ESI calculated for $C_7H_4BrClFN$ $[M+H]^+$ 238, found 238.1.

$^1H$ NMR (400 MHz, $CDCl_3$) δ 8.89 (s, 1H), 8.43 (br d, J=5.27 Hz, 1H), 7.40 (d, J=5.52 Hz, 1H), 6.26-6.42 (m, 1H).

Step 2: Preparation of Compound 28-3

Compound 26-4 (100 mg, 178.78 μmol, 1 eq) and compound 28-2 (84.55 mg, 357.56 μmol, 2 eq) were dissolved in dioxane (2 mL) and water (0.4 mL), then 1,1-bis(diphenylphosphino)ferrocene dichloropalladium (26.16 mg, 35.76 μmol, 0.2 eq) and cesium carbonate (233.00 mg, 715.12 μmol, 4 eq) were added, and the reaction solution was stirred at 100° C. under nitrogen protection for 2 hours. After the raw materials were completely reacted, the reaction solution was cooled down to 25° C., diluted by adding ethyl acetate (5 mL), filtered, and the filtrate was washed with water (5 mL×2) and saturated brine (5 mL), dried over anhydrous sodium sulfate, filtered, and the filtrate was concentrated under reduced pressure to obtain the crude product. The crude product was purified by silica gel plate (petroleum ether:ethyl acetate=1:1) to obtain compound 28-3.

MS ESI calculated for $C_{26}H_{26}ClF_5N_4O_4$ $[M+H]^+$ 589, found 589.

Step 3: Preparation of Compound 28

Compound 28-3 (52 mg, 88.29 μmol, 1 eq) was dissolved in ethanol (1 mL), then phosphoric acid (336.00 mg, 3.43 mmol, 0.2 mL, 38.83 eq) was added, and the reaction solution was stirred at 60° C. for 1 hour. After the raw materials were completely reacted, the reaction solution was cooled down to 25° C., and ethyl acetate (10 mL) was added to the reaction solution, and the organic phase was washed with water (5 mL×3) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:2) to obtain compound 28.

MS ESI calculated for $C_{21}H_{18}ClF_5N_4O_3$ $[M+H]^+$ 505, found 505.

$^1H$ NMR (400 MHz, $CDCl_3$) δ 9.14 (br s, 1H), 8.41 (br d, J=4.77 Hz, 1H), 7.55 (br d, J=5.27 Hz, 1H), 7.49 (d, J=11.54 Hz, 1H), 7.42 (d, J=6.02 Hz, 1H), 7.18-7.28 (br d, J=44 Hz, 1H), 4.87 (quin, J=6.09 Hz, 1H), 4.69 (s, 2H), 3.93 (q, J=7.19 Hz, 2H), 1.62 (d, J=6.27 Hz, 3H), 1.43 (t, J=7.15 Hz, 3H).

Example 12: Synthesis of Compound 29

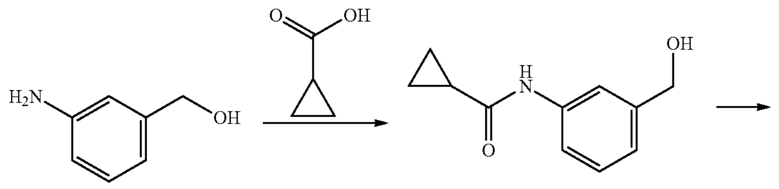

29-1 29-2

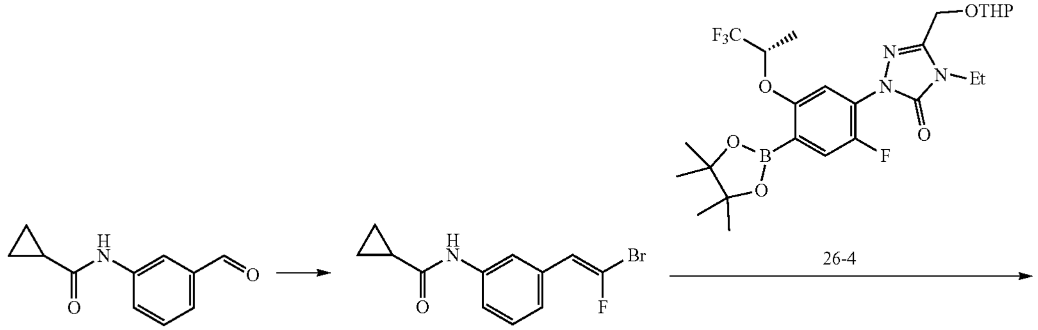

29-3 29-4

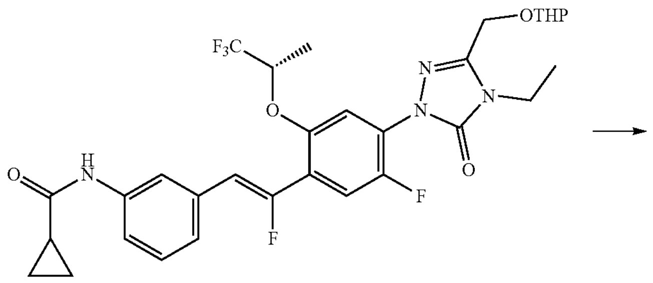

29-5

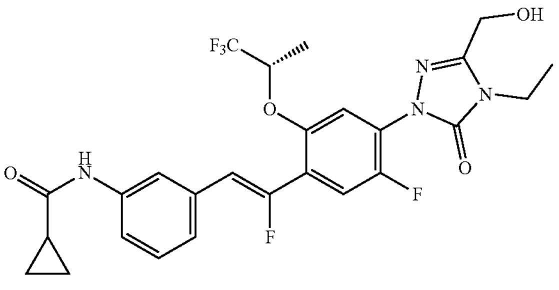

Compound 29

Step 1: Preparation of Compound 29-2

Cyclopropyl carboxylic acid (167.77 mg, 1.95 mmol, 153.92 μL, 1.2 eq) was dissolved in N,N-dimethylformamide (2 mL), then compound 29-1 (200 mg, 1.62 mmol, 1 eq) was added, ad then N,N-diisopropylethylamine (314.84 mg, 2.44 mmol, 424.31 μL, 1.5 eq) and O-(7-azabenzotriazol-1-yl)-N,N,N,N-tetramethyluronium hexafluorophosphate (HATU) (926.24 mg, 2.44 mmol, 1.5 eq) were added, and the reaction solution was stirred at 25° C. for 2 hours. After the raw materials were completely reacted, the reaction solution was diluted by adding ethyl acetate (10 mL), and the organic phase was washed with water (10 mL×2) and saturated brine (10 mL×2), dried over anhydrous sodium sulfate, filtered, and the filtrate was concentrated to dryness under reduced pressure to obtain the crude product. The crude product was purified by fast silica gel column (0-60% ethyl acetate/petroleum ether) to obtain compound 29-2.

MS ESI calculated for $C_{11}H_{13}NO_2$ $[M+H]^+$ 192, found 192.

Step 2: Preparation of Compound 29-3

Compound 29-2 (200 mg, 1.05 mmol, 1 eq) was dissolved in dichloromethane (2 mL), then manganese dioxide (909.26 mg, 10.46 mmol, 10 eq) was added, and the reaction solution was stirred at 25° C. for 12 hours. After the raw materials were completely reacted, the reaction solution was diluted by adding dichloromethane (10 mL), filtered, and the filtrate was concentrated to dryness under reduced pressure to obtain the crude product. The crude product was purified by fast silica gel column (0 to 50% ethyl acetate/petroleum ether) to obtain compound 29-3.

MS ESI calculated for $C_{11}H_{11}NO_2$ $[M+H]^+$ 190, found 190.

$^1H$ NMR (400 MHz, $CDCl_3$) δ 9.99 (s, 1H), 8.02 (s, 1H), 7.86 (br d, J=7.78 Hz, 1H), 7.63 (br d, J=7.53 Hz, 1H), 7.59 (br s, 1H), 7.44-7.54 (m, 1H), 1.51-1.58 (m, 1H), 1.08-1.19 (m, 2H), 0.86-0.95 (m, 2H).

Step 3: Preparation of Compound 29-4

Compound 29-3 (80 mg, 422.81 μmol, 1 eq) was dissolved in ethanol (2 mL), then hydrazine hydrate (74.70 mg, 1.27 mmol, 72.53 μL, purity of 85%, 3 eq) was added and the reaction solution was stirred at 25° C. for 2 hours, and ethylenediamine (76.23 mg, 1.27 mmol, 84.89 μL, 3 eq) and cuprous chloride (4.19 mg, 42.28 μmol, 1.01 μL, 0.1 eq) were added and stirred for 10 min, then tribromofluoromethane (286.16 mg, 1.06 mmol, 2.5 eq) was added at 0° C. and the reaction solution was stirred at 25° C. for 1 hour. After the raw materials were completely reacted and the reaction was quenched by adding water (2 mL) to the reaction solution, and ethyl acetate (5 mL×3) was added for extraction, and the organic phases were combined, washed with saturated brine (5 mL), dried over anhydrous sodium sulfate, filtered, and the filtrate was concentrated to dryness under reduced pressure to obtain the crude product. The crude product was purified by silica gel plate (petroleum ether: ethyl acetate=2:1) to obtain compound 29-4.

MS ESI calculated for $C_{12}H_{11}BrFNO$ $[M+H]^+$ 284, found 284.

Step 4: Preparation of Compound 29-5

Compound 26-4 (60 mg, 107.27 μmol, 1 eq) and compound 29-4 (33.52 mg, 117.99 μmol, 1.1 eq) were dissolved in dioxane (1 mL) and water (0.2 mL), then 1,1-bis(diphenylphosphino)ferrocene dichloropalladium (15.70 mg, 21.45 μmol, 0.2 eq) and cesium carbonate (139.80 mg, 429.06 μmol, 4 eq) were added and the reaction solution was stirred at 100° C. under nitrogen protection for 2 hours. After the raw materials were completely reacted, the reaction solution was cooled down to 25° C., diluted by adding ethyl acetate (10 mL), filtered, and the filtrate was washed with water (5 mL×2) and saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:1) to obtain compound 29-5.

MS ESI calculated for $C_{31}H_{33}F_5N_4O_5$ $[M+H]^+$ 637, found 637.

$^1H$ NMR (400 MHz, $CDCl_3$) δ 7.68 (s, 1H), 7.63 (br s, 1H), 7.51 (d, J=11.29 Hz, 1H), 7.42 (br s, 1H), 7.31-7.36 (m, 2H), 7.28 (br s, 1H), 6.76-6.91 (m, 1H), 4.76-4.82 (m, 2H), 4.73 (d, J=12.80 Hz, 1H), 4.49 (d, J=12.80 Hz, 1H), 3.85-3.93 (m, 3H), 3.58-3.65 (m, 1H), 1.75-1.89 (m, 2H), 1.59-1.70 (m, 4H), 1.57 (s, 2H), 1.40-1.44 (m, 3H), 1.25 (s, 2H), 1.10-1.15 (m, 2H), 0.87 (qd, J=3.73, 7.62 Hz, 2H).

Step 5: Preparation of Compound 29

Compound 29-5 (40.6 mg, 63.78 μmol, 1 eq) was dissolved in ethanol (1 mL), then phosphoric acid (336.00 mg, 3.43 mmol, 0.2 mL, 53.76 eq) was added, and the reaction solution was stirred at 60° C. for 1 hour. After the raw materials were completely reacted, the reaction solution was cooled down to 25° C., diluted by adding water (2 mL), extracted with ethyl acetate (5 mL×3), and the organic phases were combined, washed with saturated brine (5 mL), dried over anhydrous sodium sulfate, filtered, and the filtrate was concentrated to dryness under reduced pressure to obtain the crude product. The crude product was purified by silica gel plate (petroleum ether:ethyl acetate=1:2) to obtain compound 29.

MS ESI calculated for $C_{26}H_{25}F_5N_4O_4$ $[M+H]^+$ 553, found 553.

$^1H$ NMR (400 MHz, $CDCl_3$) δ 7.67 (br s, 1H), 7.61 (br s, 1H), 7.52 (s, 1H), 7.50 (d, J=11.54 Hz, 1H), 7.29-7.35 (m, 2H), 7.27-7.28 (br d, J=4.00 Hz, 1H), 6.76-6.89 (m, 1H), 4.77 (spt, J=6.19 Hz, 1H), 4.66 (d, J=5.77 Hz, 2H), 3.91 (q, J=7.28 Hz, 2H), 2.53 (br s, 1H), 1.57 (d, J=6.53 Hz, 3H), 1.54 (br s, 1H), 1.42 (t, J=7.15 Hz, 3H), 1.09-1.14 (m, 2H), 0.84-0.90 (m, 2H).

Example 13: Synthesis of Compound 30

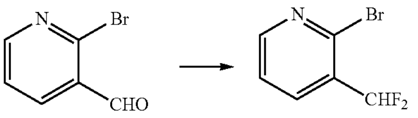

30-A 30-1

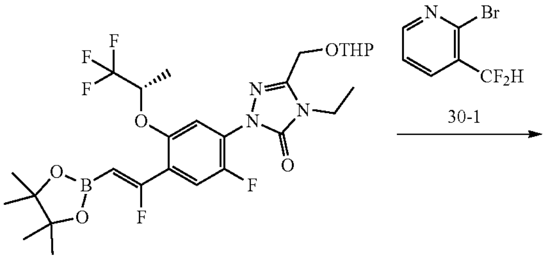

5-2

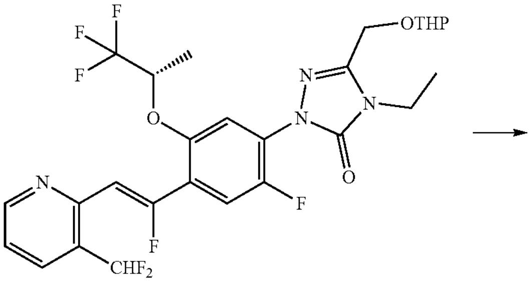

30-2

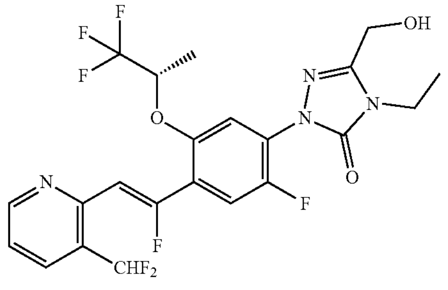

Compound 30

Step 1: Preparation of Compound 30-1

Dichloromethane (10 mL) and compound 30-A (0.5 g, 2.69 mmol, 1 eq) were added to a reaction flask and started to stir; then after the temperature was cooled down to 0-5° C., and (2-methoxyethyl)aminosulfur trifluoride (1.49 g, 6.72 mmol, 1.47 mL, 2.5 eq) was added dropwise thereto and reacted for 2 hours. After the reaction solution was poured into 10 mL of saturated sodium bicarbonate solution, 20 mL of dichloromethane was added for extraction; the obtained organic phase was dried over anhydrous sodium sulfate, filtered, and the filtrate was subjected to rotary evaporation under reduced pressure at 45° C. The crude product was purified by silica gel column chromatography (gradient elution:petroleum ether:ethyl acetate=100:0-70:30) to obtain compound 30-1.

Step 2: Preparation of Compound 30-2

1,4-Dioxane (3 mL), water (0.6 mL), compound 5-2 (150 mg) and compound 30-1 (38.78 mg, 186.45 μmol) were added to a reaction flask and started to stir; then anhydrous potassium phosphate (65.96 mg, 310.75 μmol) was added thereto, and after nitrogen displacement, [1,1-bis(diphenylphosphino)ferrocene]dichloropalladium (9.10 mg, 12.43 μmol) was added, heated to 90° C., and reacted for 0.5 hours. 5 mL of water and 5 mL of ethyl acetate were added to the reaction system, and the solution was separated; the obtained organic phase was washed once with 5 mL of saturated brine, dried over anhydrous sodium sulfate, filtered, and the filtrate was subjected to rotary evaporation under reduced pressure at 45° C. The crude product was purified by silica gel column chromatography (gradient elution:petroleum ether:ethyl acetate=100:0 to 50:50) to obtain compound 30-2.

MS ESI calculated for $C_{27}H_{27}F_7N_4O_4$, $[M+H]^+$ 605.5, found 605.4.

$^1H$ NMR (400 MHz, $CDCl_3$) δ=8.81 (d, J=4.4 Hz, 1H), 7.98 (d, J=7.6 Hz, 1H), 7.60 (d, J=11.2 Hz, 1H), 7.36-7.33 (m, 2H), 7.12 (d, J=37.6 Hz, 1H), 6.85 (t, J=54.8 Hz, 1H), 4.91-4.81 (m, 1H), 4.77-4.72 (m, 2H), 4.51-4.48 (m, 1H), 3.93-3.86 (m, 3H), 3.63-3.60 (m, 1H), 1.87-1.76 (m, 2H), 1.67-1.59 (m, 7H), 1.43 (t, J=7.2 Hz, 3H).

Step 3: Preparation of Compound 30

Ethanol (1.5 mL), compound 30-2 (15 mg, 24.81 μmol) were added to a reaction flask and started to stir; then phosphoric acid (48.63 mg, 496.27 μmol, 28.95 μL) was added thereto, heated to 60° C. and reacted for 12 hours. After the reaction solution was cooled down to room temperature, the pH value was adjusted to 7 by adding saturated sodium bicarbonate solution to the reaction system, and the reaction solution was subjected to rotary evaporation under reduced pressure at 45° C.; the obtained aqueous solution was extracted by adding 5 mL of ethyl acetate, and the organic phase was washed once with 5 mL of saturated brine, dried over anhydrous sodium sulfate, filtered, and the filtrate was subjected to rotary evaporation under reduced pressure at 45° C. The crude product was purified by thin-layer chromatography (the developing solvent was petroleum ether:ethyl acetate=1:2) to obtain the product. Compound 30 was obtained.

MS ESI calculated for $C_{22}H_{19}F_7N_4O_3$, $[M+H]^+$ 521.4, found 521.1.

$^1H$ NMR (400 MHz, $CDCl_3$) δ=8.81 (d, J=4.4 Hz, 1H), 7.99 (d, J=7.6 Hz, 1H), 7.60 (d, J=11.6 Hz, 1H), 7.38-7.34 (m, 2H), 7.13 (d, J=37.6 Hz, 1H), 6.85 (t, J=54.8 Hz, 1H), 4.89-4.83 (m, 1H), 4.69 (s, 2H), 3.95-3.83 (m, 2H), 2.24 (s, 1H), 1.62 (d, J=6.8 Hz, 3H), 1.43 (t, J=7.2 Hz, 3H).

Example 14: Synthesis of Compound 31

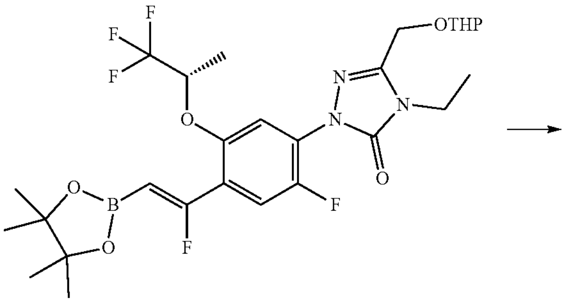

5-2

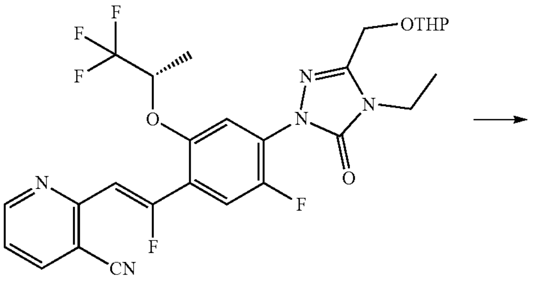

31-1

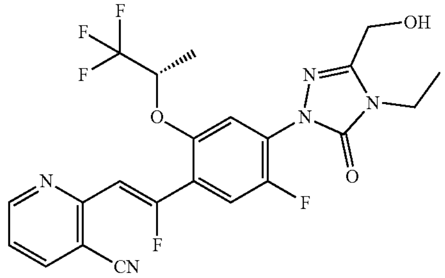

Compound 31

Step 1: Preparation of Compound 31-1

1,4-Dioxane (1 mL), water (0.2 mL), compound 5-2 (40 mg, 66.29 μmol), and 2-bromo-3-cyanopyridine (30.33 mg, 165.73 μmol) were added to a reaction flask and started to stir; then anhydrous potassium phosphate (35.18 mg, 165.73 μmol, 2.5 eq) was added thereto, after nitrogen displacement, (2-dicyclohexylphosphino-2,4,6-triisopropyl-1,1-biphenyl)[2-(2-amino-1,1-biphenyl)]palladium methanesulfonate (11.22 mg, 13.26 μmol) was added thereto, heated to 90° C. and reacted for 0.5 hours. 5 mL of water and 5 mL of ethyl acetate were added to the reaction system, and the solution was separated; the resulting organic phase was washed once with 5 mL of saturated brine, dried over anhydrous sodium sulfate, filtered, and the filtrate was subjected to rotary evaporation under reduced pressure at 45° C. The crude product was separated and purified by silica gel column chromatography (gradient elution:petroleum ether:ethyl acetate=100:0-50:50) to obtain compound 31-1.

MS ESI calculated for $C_{27}H_{26}F_5N_5O_4$, $[M+H]^+$ 580.5, found 580.3.

Step 2: Preparation of Compound 31

Ethanol (3 mL), compound 31-1 (15 mg, 25.88 μmol) were added to a reaction flask and started to stir; then phosphoric acid (50.73 mg, 517.67 μmol, 30.20 μL) was added thereto, heated to 65° C. and reacted for 15 hours. After the reaction solution was combined with the small test reaction solution, the reaction solution was cooled down to room temperature and the pH value was adjusted to 7 by adding saturated sodium bicarbonate solution to the reaction system, and the reaction solution was subjected to rotary evaporation under reduced pressure at 45° C.; the resulting aqueous solution was extracted by adding 5 mL of ethyl acetate, and the organic phase was washed once with 5 mL of saturated brine, dried over anhydrous sodium sulfate, filtered, and the filtrate was subjected to rotary evaporation under reduced pressure at 45° C. The crude product was separated and purified by thin-layer chromatography (the developing solvent was petroleum ether:ethyl acetate=1:2) to obtain compound 31.

MS ESI calculated for $C_{22}H_{18}F_5N_5O_3$, $[M+H]^+$ 496.4, found 496.0.

$^1H$ NMR (400 MHz, $CDCl_3$) δ=8.89 (d, J=4.8 Hz, 1H), 7.99 (dd, J=7.6 and 1.6 Hz, 1H), 7.63 (d, J=11.6 Hz, 1H), 7.42-7.41 (m, 2H), 7.32-7.29 (m, 1H), 4.90-4.82 (m, 1H), 4.69 (s, 2H), 3.95-3.89 (m, 2H), 2.14 (s, 1H), 1.68 (d, J=6.4 Hz, 3H), 1.43 (t, J=7.2 Hz, 3H).

Example 15: Synthesis of Compound 32

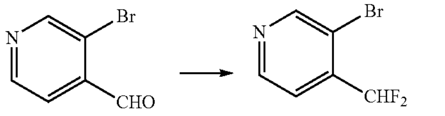

32-A 32-B

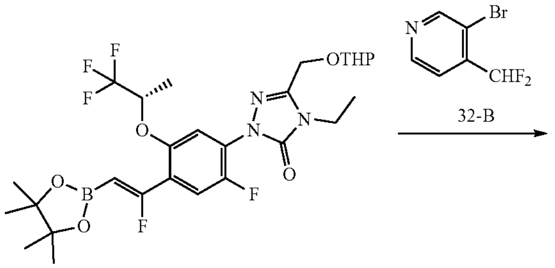

5-2

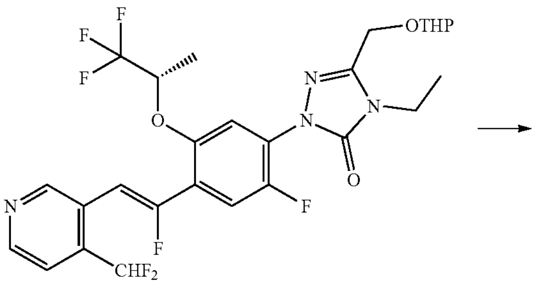

32-1

-continued

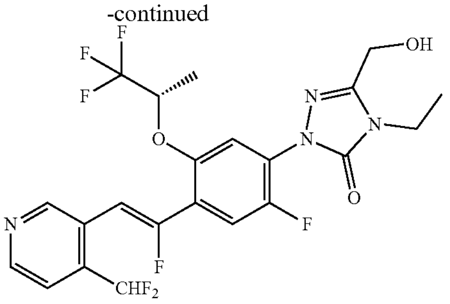

32

Step 1: Preparation of Compound 32-B

Compound 32-A (2 g, 10.75 mmol) was dissolved in dichloromethane (100 mL), and (2-methoxyethyl)aminosulfur trifluoride (9.04 g, 40.86 mmol, 8.95 mL) was added at 0° C., heated naturally to 15° C. and stirred for 2 hours. After 20 mL of saturated sodium bicarbonate aqueous solution was added to the reaction solution, 80 mL of water was added to extract once, and the organic phase was dried over anhydrous sodium sulfate and concentrated. The crude product was purified by silica gel column chromatography separation (gradient elution:petroleum ether:ethyl acetate=100:0-3:1) to obtain compound 32-B.

Step 2: Preparation of Compound 32-1

1,4-Dioxane (3 mL), water (0.6 mL), compound 5-2 (170 mg) and compound 32-B (35.16 mg, 169.05 μmol) were added to a reaction flask and started to stir; then anhydrous potassium phosphate (44.85 mg, 211.31 μmol) was added thereto, and after nitrogen displacement, [1,1-bis(diphenylphosphino)ferrocene]dichloropalladium (6.18 mg, 8.45 μmol) was added thereto, heated to 90° C. and reacted for 0.5 hours. After combining with the small test reaction solution, 5 mL of water and 5 mL of ethyl acetate were added to the reaction system, and the reaction solution was separated; and the resulting organic phase was washed once with 5 mL of saturated brine, dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0-50:50) to obtain compound 32-1.

MS ESI calculated for $C_{27}H_{27}F_7N_4O_4$, $[M+H]^+$ 605.5, found 605.3.

$^1H$ NMR (400 MHz, $CDCl_3$) δ=9.10 (s, 1H), 8.66 (d, J=4.8 Hz, 1H), 7.59-7.53 (m, 2H), 7.36 (d, J=5.6 Hz, 1H), 7.02 (d, J=39.6 Hz, 1H), 6.78 (d, J=54.8 Hz, 1H), 4.91-4.82 (m, 1H), 4.77-4.71 (m, 2H), 4.51-4.48 (m, 1H), 3.93-3.85 (m, 3H), 3.63-3.60 (m, 1H), 1.87-1.76 (m, 2H), 1.67-1.59 (m, 7H), 1.42 (t, J=7.2 Hz, 3H).

Step 3: Preparation of Compound 32

Ethanol (1.5 mL), compound 32-1 (18 mg, 29.78 μmol) were added to a reaction flask and started to stir; then phosphoric acid (68.66 mg, 595.52 μmol, 40.87 μL,) was added thereto, heated to 65° C. and reacted for 15 hours. After the reaction solution was cooled down to room temperature, the pH value was adjusted to 7 by adding saturated sodium bicarbonate solution to the reaction system, and the reaction solution was subjected to rotary evaporation under reduced pressure at 45° C. The resulting aqueous solution was extracted by adding 5 mL of ethyl acetate, and the organic phase was washed once with 5 mL of saturated brine, dried over anhydrous sodium sulfate, filtered, and the filtrate was subjected to rotary evaporation under reduced pressure at 45° C. The crude product was separated and purified by high performance liquid chromatography, the high performance liquid chromatography (HPLC) method: ACSTJ-GX-z preparative chromatograph; chromatographic column: Waters Xbridge BEH C18 100*30 mm*10 μm; mobile phase A: $H_2O$ (10 mM $NH_4HCO_3$), mobile phase B: acetonitrile; running gradient: B %: 30%-60%, running for 10 min. Compound 32 was obtained.

MS ESI calculated for $C_{22}H_{19}F_7N_4O_3$, $[M+H]^+$ 521.4, found 521.1.

$^1$H NMR (400 MHz, $CDCl_3$) δ=9.09 (s, 1H), 8.64 (s, 1H), 7.56 (d, J=4.8 Hz, 1H), 7.48 (d, J=11.6 Hz, 1H), 7.42 (d, J=5.6 Hz, 1H), 7.02 (d, J=39.6 Hz, 1H), 6.78 (d, J=54.4 Hz, 1H), 4.90-4.84 (m, 1H), 4.69 (s, 2H), 3.96-3.91 (m, 2H), 1.62 (d, J=6.4 Hz, 3H), 1.44 (t, J=7.2 Hz, 3H).

Example 16: Synthesis of Compound 33

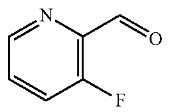

33-1

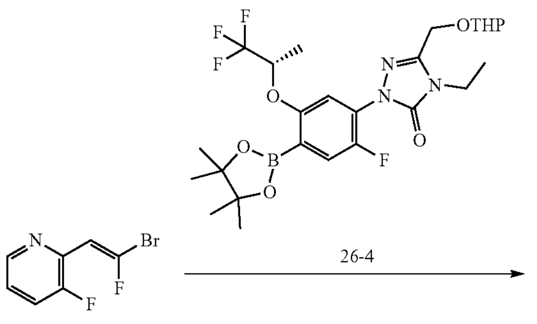

33-2

26-4

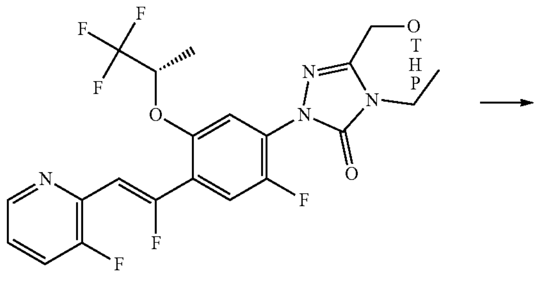

33-3

-continued

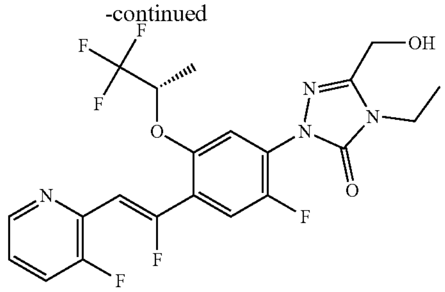

Compound 33

Step 1: Preparation of Compound 33-2

Compound 33-1 (400 mg, 3.20 mmol), triphenylphosphine (1.26 g, 4.80 mmol), tribromofluoromethane (1.30 g, 4.80 mmol) and tetrahydrofuran (8 mL) were added to a pre-washed and dry reaction flask, cooled down to 0° C. after nitrogen displacement three times; diethylzinc (1 M, 4.80 mL, 1.5 eq) was added, naturally heated to 25° C. and reacted for 2 hours. The reaction was completed, quenched by adding saturated ammonium chloride aqueous solution (10 mL), extracted with ethyl acetate (20 mL*3), and the organic phases were washed with saturated brine (10 mL), dried over anhydrous sodium sulfate, filtered and concentrated under reduced pressure to obtain the crude product. The crude product was purified by column chromatography (petroleum ether:ethyl acetate=100:0-100:10) to obtain compound 33-2.

Step 2: Preparation of Compound 33-4

Compound 26-4 (100 mg, 178.78 μmol), dioxane (1 mL), water (0.2 mL), compound 33-2 (78.67 mg, 357.55 μmol) and cesium carbonate (233.00 mg, 715.11 μmol) were added to a reaction flask, after nitrogen displacement three times, [1,1-bis(diphenylphosphino)ferrocene]dichloropalladium (26.16 mg, 35.76 μmol) was added and stirred at 100° C. for 4 hours. After the reaction was completed, the reaction solution was added with water (5 mL), extracted three times using ethyl acetate (10 mL), and the organic phase was collected; the organic phase was dried over anhydrous sodium sulfate, filtered, and concentrated under reduced pressure to obtain the crude product. The crude product was purified by column chromatography (petroleum ether:ethyl acetate=100:0-50:50) to obtain compound 33-3.

$^1$H NMR (400 MHz, $CD_3OD$) δ ppm 8.45 (d, J=4.88 Hz, 1H), 7.63-7.68 (m, 2H), 7.51-7.56 (m, 1H), 7.41 (dt, J=8.60, 4.39 Hz, 1H), 7.13-7.26 (m, 1H), 5.25 (dt, J=12.63, 6.19 Hz, 1H), 4.81 (m, 1H), 4.75 (d, J=12.88 Hz, 1H), 4.56 (d, J=12.88 Hz, 1H), 3.91 (q, J=7.09 Hz, 3H), 3.54-3.65 (m, 1H), 1.72-1.90 (m, 2H), 1.52-1.68 (m, 7H), 1.39 (t, J=7.19 Hz, 3H).

Step 3: Preparation of Compound 33

Compound 33-3 (30 mg, 52.40 μmol), ethanol (1 mL) and phosphoric acid (97.57 mg, 995.64 μmol, 58.08 μL) were added to a reaction flask with nitrogen replacement three times, and stirred at 60° C. for 16 hours. After the reaction was completed, the reaction solution was added with water (5 mL) and adjusted with saturated sodium bicarbonate aqueous solution to pH=7, and then extracted three times with ethyl acetate (10 mL). The organic phase was collected and washed three times with saturated brine (10 mL), dried over anhydrous sodium sulfate, filtered and concentrated under reduced pressure to obtain the crude product. The crude product was purified by TLC (petroleum ether:ethyl acetate=1:2), and then 1 mL of petroleum ether and 0.2 mL of ethyl acetate were added to the product, stirred for 10 min, filtered, and the filter cake was collected and concentrated under reduced pressure to obtain compound 33.

MS ESI calculated for $C_{21}H_{18}F_6N_4O_3$ $[M+H]^+$ 489, found 489.

$^1$H NMR (400 MHz, $CDCl_3$) δ ppm 8.54 (d, J=4.38 Hz, 1H), 7.62 (d, J=11.51 Hz, 1H), 7.43 (t, J=9.07 Hz, 1H), 7.34 (d, J=6.00 Hz, 1H), 7.17-7.26 (m, 2H), 4.82 (dt, J=12.16, 5.99 Hz, 1H), 4.69 (d, J=6.25 Hz, 2H), 3.92 (q, J=7.17 Hz, 2H), 2.17 (t, J=6.38 Hz, 1H), 1.61 (d, J=6.38 Hz, 3H), 1.43 (t, J=7.19 Hz, 3H).

Example 17: Synthesis of Compound 1

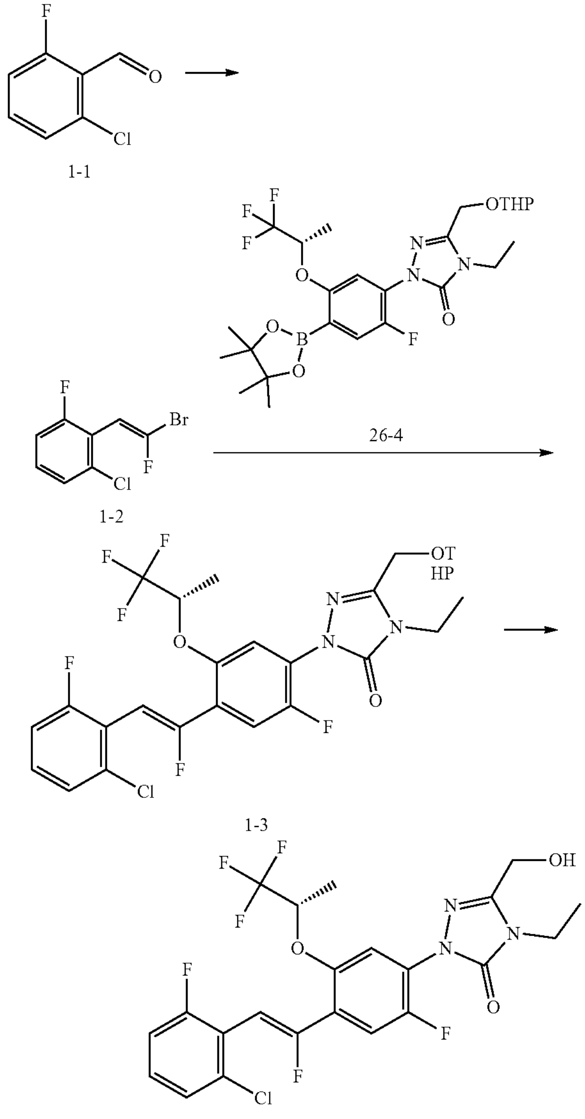

1-1

26-4

1-2

1-3

Compound 1

Step 1: Preparation of Compound 1-2

Compound 1-1 (400 mg, 2.52 mmol), triphenylphosphine (992.54 mg, 3.78 mmol), diethylzinc (1 M, 3.78 mL), and tetrahydrofuran (8 mL) were added to a pre-washed and dry reaction flask with nitrogen displacement three times, cooled down to 0° C., and tribromofluoromethane (1.02 g, 3.78 mmol) was added, naturally heated to 25° C. and reacted for 2 hours. The reaction was completed, quenched by adding saturated ammonium chloride aqueous solution (10 mL), extracted three times with ethyl acetate (20 mL), and the organic phases were washed with saturated brine (10 mL), dried over anhydrous sodium sulfate, filtered and concentrated under reduced pressure to obtain the crude product. The crude product was purified by column chromatography (petroleum ether:ethyl acetate=100:0-100:10) to obtain compound 1-2.

$^1$H NMR (400 MHz, $CDCl_3$) δ ppm 7.16-7.21 (m, 1H), 7.00-7.09 (m, 1H), 6.46 (d, J=10.51 Hz, 1H), 5.99-6.10 (m, 1H).

Step 2: Preparation of Compound 1-3

Compound 26-4 (100 mg, 178.78 μmol), compound 1-2 (58.91 mg, crude), dioxane (1.5 mL), water (0.3 mL) were added to a reaction flask with nitrogen displacement three times, then [1,1-bis(diphenylphosphino)ferrocene]dichloropalladium (26.16 mg, 35.76 μmol) and cesium carbonate (233.00 mg, 715.11 μmol) were added with nitrogen displacement three times and stirred at 100° C. for 4 hours. After the reaction solution was cooled to room temperature, water (5 mL) was added to the reaction solution, extracted with ethyl acetate (20 mL*3), and the organic phases were collected, dried over anhydrous sodium sulfate, filtered, and concentrated under reduced pressure to obtain the crude product. The crude product was purified by column chromatography (petroleum ether:ethyl acetate=100:0-50:50) to obtain compound 1-3.

MS ESI calculated for $C_{22}H_{18}ClF_6N_3O_3$ $[M+H]^+$ 606, found 606.

$^1$H NMR (400 MHz, $CD_3OD$) δ ppm 7.59 (d, J=11.13 Hz, 1H), 7.52 (d, J=5.63 Hz, 1H), 7.30-7.40 (m, 2H), 7.13-7.19 (m, 1H), 6.83-6.97 (m, 1H), 5.25 (dt, J=12.57, 6.22 Hz, 1H), 4.82 (m, J=2.75 Hz, 1H), 4.76 (d, J=12.88 Hz, 1H), 4.56 (d, J=12.88 Hz, 1H), 3.85-3.96 (m, 3H), 3.55-3.66 (m, 1H), 1.74-1.92 (m, 2H), 1.56-1.67 (m, 7H), 1.39 (t, J=7.13 Hz, 3H).

Step 3: Preparation of Compound 1

Compound 1-3 (100 mg, 165.03 μmol), ethanol (1 mL) and phosphoric acid (307.28 mg, 3.14 mmol, 182.91 μL) were added to a reaction flask with nitrogen displacement three times and stirred at 60° C. for 1 hour. After the reaction was completed, the reaction solution was added with water (5 mL) and adjusted with saturated sodium bicarbonate aqueous solution to pH=7 and extracted three times with ethyl acetate (10 mL). The organic phases were collected and washed three times with saturated brine (10 mL), dried over anhydrous sodium sulfate, filtered and concentrated under reduced pressure to obtain the crude product. The crude product was purified by column chromatography (petroleum ether:ethyl acetate=100:0-10:20), and the resulting product was stirred with 2 mL of petroleum ether and 0.4 mL of ethyl acetate for 10 min, then filtered, and the filter cake was concentrated under reduced pressure to obtain compound 1.

MS ESI calculated for was $C_{22}H_{18}ClF_6N_3O_3$ $[M+H]^+$ 522, and the found was 522.

Example 18: Synthesis of Compound 35

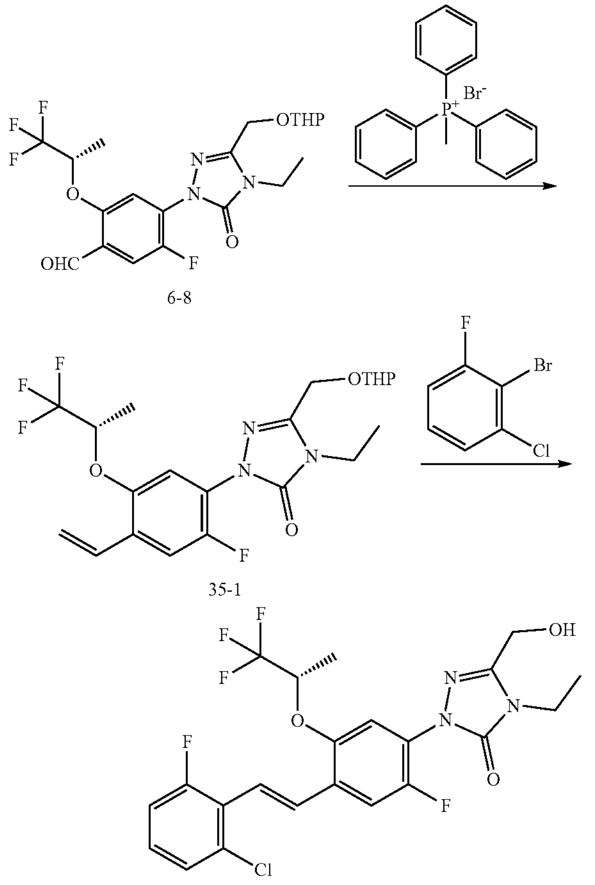

6-8

35-1

Compound 35

Step 1: Preparation of Compound 35-1

Tetrahydrofuran (15 mL), methyltriphenylphosphonium bromide (232.76 mg, 651.58 μmol) were added to a reaction flask and started to stir; then the temperature was cooled down to −30° C., and potassium tert-butoxide (73.11 mg, 651.58 μmol) was added thereto, heated to 15° C. and reacted for 1.5 hours. Then compound 6-8 (150 mg, 325.79 μmol) dissolved in tetrahydrofuran (3 mL) was added dropwise thereto and reacted at 15° C. for 0.5 hours. The reaction solution was quenched by adding saturated ammonium chloride aqueous solution (20 mL) to the reaction solution and extracted by adding ethyl acetate (10 mL×2); the organic phases were combined, washed with saturated brine (15 mL×1), dried over anhydrous sodium sulfate, filtered, and the filtrate was concentrated under reduced pressure. The crude product was purified by silica gel column chromatography separation (gradient elution:petroleum ether:ethyl acetate=100:0-70:30) to obtain compound 35-1.

MS ESI calculated for $C_{21}H_{25}F_4N_3O_4$, $[M+H]^+$ 460.2, found 460.1.

$^1H$ NMR (400 MHz, $CDCl_3$) δ=7.51 (d, J=11.2 Hz, 1H), 7.29 (d, J=6.0 Hz, 1H), 7.04-6.96 (m, 1H), 5.89 (d, J=18.0 Hz, 1H), 5.42 (d, J=11.2 Hz, 1H), 5.00-4.94 (m, 1H), 4.80-4.72 (m, 2H), 4.54 (d, J=13.2 Hz, 1H), 3.92-3.87 (m, 3H), 3.60-3.57 (m, 1H), 1.87-1.77 (m, 2H), 1.65-1.59 (m, 4H), 1.50 (d, J=6.4 Hz, 3H), 1.38 (t, J=7.2 Hz, 3H).

Step 2: Preparation of Compound 35

N-Methylpyrrolidone (1 mL), compound 35-1 (50 mg, 108.83 μmol), 2-chloro-6-fluorobromobenzene (56.98 mg, 272.07 μmol) were added to a reaction flask and started to stir; after nitrogen displacement, triethylamine (44.05 mg, 435.32 μmol, 60.59 μL) and bis(tri-tert-butylphosphine) palladium(0) (5.56 mg, 10.88 μmol) were added thereto, heated to 140° C. and reacted for 12 hours. After the reaction solution was reduced to room temperature, combined with the reaction solution of the small test, and the reaction solution was poured into 5 mL of saturated ammonium chloride solution and then extracted by adding 5 mL of ethyl acetate; the resulting organic phase was washed with saturated brine (5 mL×3), dried over anhydrous sodium sulfate, filtered, and the filtrate was concentrated under reduced pressure at 45° C. The crude product was separated and purified by high performance liquid chromatography (HPLC); high performance liquid preparation method: ACSTJ-GX-AB preparative chromatograph; chromatographic column: Waters Xbridge BEH C18 100*30 mm*10 μm; mobile phase A: $H_2O$ (10 mM $NH_4HCO_3$), mobile phase B: acetonitrile; running gradient: B %: 45%-75%, which was run for 8 min to obtain compound 35.

MS ESI calculated for $C_{22}H_{19}ClF_5N_3O_3$, $[M+H]^+$ 504.1, found 504.0.

$^1H$ NMR (400 MHz, $CDCl_3$) δ=7.66 (d, J=16.0 Hz, 1H), 7.52 (d, J=16.0 Hz, 1H), 7.28-7.21 (m, 3H), 7.20-7.15 (m, 1H), 7.08-7.04 (m, 1H), 4.69-4.67 (m, 2H), 4.65-4.59 (m, 1H), 3.91 (dd, J=14.4 Hz, 7.2 Hz, 2H), 2.01 (brs, 1H), 1.56-1.55 (m, 3H), 1.43 (t, J=7.2 Hz, 3H).

Example 19: Synthesis of Compound 36

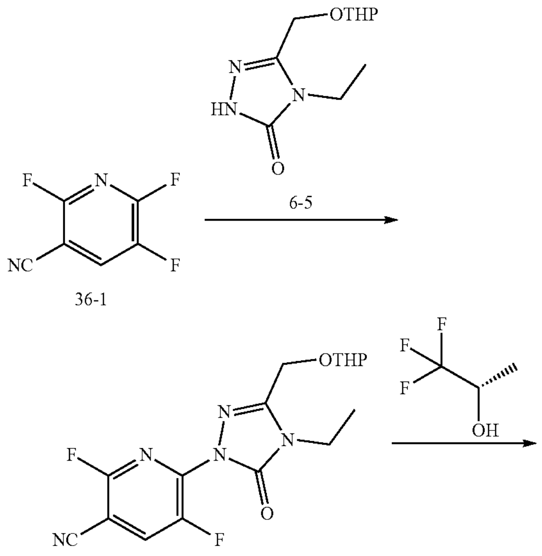

36-1

36-2

-continued

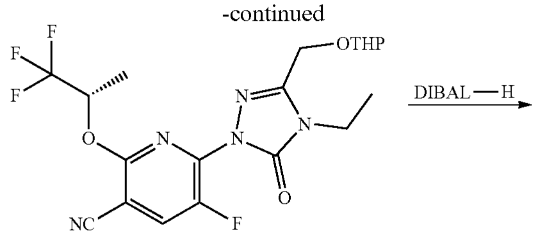

36-3

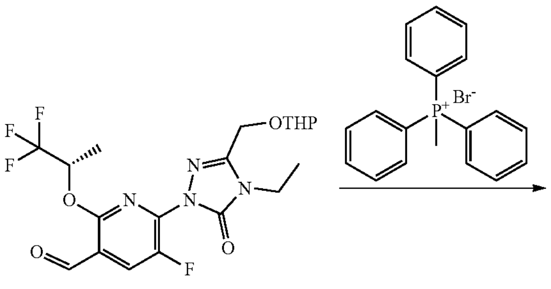

36-4

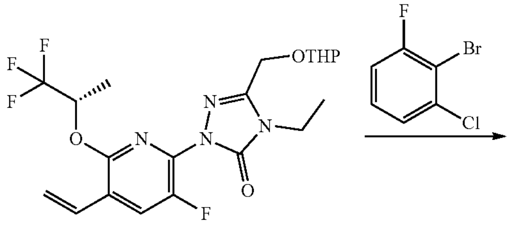

36-5

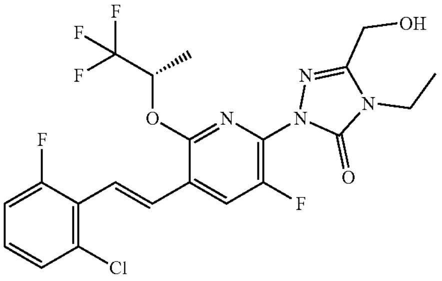

Compound 36

Step 1: Preparation of Compound 36-2

Acetonitrile (5 mL), compound 36-1 (0.5 g, 3.16 mmol) and compound 6-5 (653.46 mg, 2.88 mmol) were added to a reaction flask and started to stir; then anhydrous potassium phosphate (1.22 g, 5.75 mmol) was added thereto, heated to 70° C. and reacted for 12 hours. 15 mL of water and 10 mL of ethyl acetate were added to the reaction system and the solution was separated; the resulting organic phase was washed once with 15 mL of saturated brine, dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0-50:50) to obtain compound 36-2.

MS ESI calculated for $C_{16}H_{17}F_2N_5O_3$, $[M+H]^+$ 366.1, found 366.2.

$^1$H NMR (400 MHz, $CDCl_3$) δ=7.99-7.95 (m, 1H), 4.75-4.72 (m, 2H), 4.50 (d, J=13.2 Hz, 1H), 3.92-3.83 (m, 3H), 3.63-3.59 (m, 1H), 1.85-1.75 (m, 2H), 1.68-1.56 (m, 4H), 1.40 (t, J=7.2 Hz, 3H).

Step 2: Preparation of Compound 36-3

Acetonitrile (5 mL) and compound 36-2 (450 mg, 1.23 mmol) were added to a reaction flask and started to stir; then anhydrous potassium phosphate (522.93 mg, 2.46 mmol) and (2S)-1,1,1-trifluoro-2-propanol (210.75 mg, 1.85 mmol) were added thereto, heated to 73° C. and reacted for 12 hours. 15 mL of water and 10 mL of ethyl acetate were added to the reaction system and the solution was separated; the resulting organic phase was washed once with 15 mL saturated brine, dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0-50:50) to obtain compound 36-3.

MS ESI calculated for $C_{19}H_{21}F_4N_5O_4$, $[M+Na]^+$ 482.1, found 482.3.

$^1$H NMR (400 MHz, $CDCl_3$) δ=7.85 (d, J=8.4 Hz, 1H), 5.78-5.68 (m, 1H), 4.77-4.72 (m, 2H), 4.51-4.48 (m, 1H), 3.92-3.84 (m, 3H), 3.63-3.59 (m, 1H), 1.89-1.76 (m, 2H), 1.68-1.58 (m, 7H), 1.41 (d, J=7.2 Hz, 3H).

Step 3: Preparation of Compound 36-4

Dichloromethane (9 mL) and compound 36-3 (0.6 g, 1.31 mmol) were added to a reaction flask and started to stir; then the temperature was cooled down to −70° C., and diisobutylaluminium hydride (1 M, 3.92 mL) was added dropwise thereto and reacted for 1 hour. Then hydrochloric acid (1 M, 6.53 mL) was added dropwise thereto, slowly heated to 20° C. and reacted for 15 hours. The reaction solution was quenched by adding saturated ammonium chloride aqueous solution (10 mL), and extracted by adding dichloromethane (10 mL*2); the organic phases were combined, washed with saturated brine (10 mL×2), dried over anhydrous sodium sulfate, filtered, and the filtrate was concentrated under reduced pressure. The crude product was purified by silica gel column chromatography separation (gradient elution: petroleum ether:ethyl acetate=100:0-60:40) to obtain compound 36-4.

MS ESI calculated for $C_{19}H_{22}F_4N_4O_5$, [M+H]+ 463.1, found 463.1.

$^1$H NMR (400 MHz, $CDCl_3$) δ=10.31 (d, J=2.8 Hz, 1H), 8.06 (d, J=8.4 Hz, 1H), 5.84-5.77 (m, 1H), 4.77-4.73 (m, 2H), 4.52-4.49 (m, 1H), 3.93-3.85 (m, 3H), 3.63-3.60 (m, 1H), 1.85-1.76 (m, 2H), 1.66-1.56 (m, 7H), 1.41 (t, J=7.2 Hz, 3H).

Step 4: Preparation of Compound 36-5

Tetrahydrofuran (5 mL), methyltriphenylphosphonium bromide (46.35 mg, 129.76 μmol) were added to a reaction flask and started to stir; then the temperature was cooled down to −30° C., potassium tert-butoxide (14.56 mg, 129.76 μmol) was added thereto, heated to 15° C. and reacted for 1.5 hours. Then the temperature was cooled down to 0° C. and compound 36-4 (30 mg, 64.88 μmol) dissolved in 0.2 mL of tetrahydrofuran was added dropwise thereto, heated to 15° C. and reacted for 12 hours. After combining with the reaction solution of the small test, the reaction solution was quenched by adding saturated ammonium chloride solution (15 mL), and extracted by adding ethyl acetate (10 mL×2). The organic phases were combined, washed with saturated brine (15 mL×1), dried over anhydrous sodium sulfate, filtered, and the filtrate was concentrated under reduced pressure. The crude product was purified by silica gel column chromatography separation (gradient elution:petroleum ether:ethyl acetate=100:0-40:60) to obtain compound 36-5.

MS ESI calculated for $C_{20}H_{24}F_4N_4O_4$, $[M+H]^+$ 461.2, found 461.1.

Step 5: Preparation of Compound 36

N-Methylpyrrolidone (0.7 mL), compound 36-5 (30 mg, 65.16 μmol) and 2-chloro-6-fluorobromobenzene (40.94 mg, 195.47 μmol) were added to a reaction flask and started to stir; after nitrogen displacement, triethylamine (23.08 mg, 228.05 μmol, 31.74 μL) and bis(tri-tert-butylphosphine) palladium(0) (6.66 mg, 13.03 μmol) were added thereto, heated to 140° C. and reacted for 12 hours. The reaction solution was poured into 5 mL of saturated ammonium chloride solution and extracted by adding 5 mL of ethyl acetate. The resulting organic phase was washed with saturated brine (5 mL×3), dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0-50:50) to obtain compound 36.

MS ESI calculated for $C_{21}H_{18}ClF_5N_4O_3$, $[M+H]^+$ 505.1, found 505.0.

$^1H$ NMR (400 MHz, $CDCl_3$) δ=7.80 (d, J=9.2 Hz, 1H), 7.51-7.40 (m, 2H), 7.25-7.17 (m, 2H), 7.09-7.04 (m, 1H), 5.76-5.69 (m, 1H), 4.69 (d, J=6.4 Hz, 2H), 3.94-3.89 (m, 2H), 2.06-2.01 (m, 1H), 1.57-1.55 (m, 3H), 1.44 (t, J=7.2 Hz, 3H).

Example 20: Synthesis of Compound 37

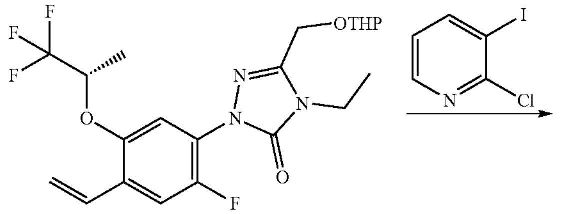

35-1

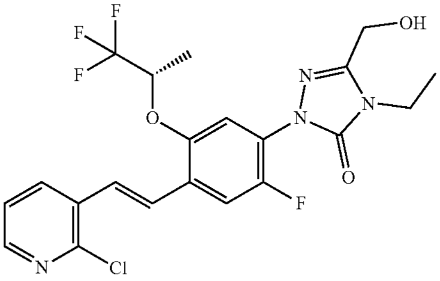

Compound 37

Step 1: Preparation of Compound 37

N-Methylpyrrolidone (0.7 mL), compound 35-1 (30 mg, 65.30 μmol) and 2-chloro-3-iodopyridine (39.09 mg, 163.24 μmol) were added to a reaction flask and started to stir; after nitrogen replacement, triethylamine (26.43 mg, 261.19 μmol, 36.35 μL) and bis(tri-tert-butylphosphine)palladium (0) (3.34 mg, 6.53 μmol) were added thereto, heated to 135° C. and reacted for 10 hours. After pouring the reaction into 10 mL of saturated ammonium chloride solution, ethyl acetate (10 mL×3) was added for extraction; the resulting organic phases were washed with saturated brine (10 mL×3), dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0 to 30:70) to obtain the crude product. The crude product was dissolved in 0.4 mL of dichloromethane, and petroleum ether (0.9 mL) was added dropwise and stirred for 30 min, then filtered, and the filter cake was washed with dichloromethane/petroleum ether (1/2, 0.5 mL×2), and then subjected to rotary evaporation under reduced pressure at 45° C. to obtain compound 37.

MS ESI calculated for $C_{21}H_{19}ClF_4N_4O_3$, $[M+H]^+$ 487.1, found 487.1.

$^1H$ NMR (400 MHz, $CD_3OD$) δ=8.31-8.29 (m, 1H), 8.18-8.16 (m, 1H), 7.66-7.59 (m, 2H), 7.46-7.42 (m, 2H), 7.36 (d, J=6.4 Hz, 1H), 5.10-5.14 (m, 1H), 4.60 (s, 2H), 3.94-3.89 (m, 2H), 1.56 (d, J=6.4 Hz, 3H), 1.39 (t, J=7.2 Hz, 3H).

Example 21: Synthesis of Compound 38

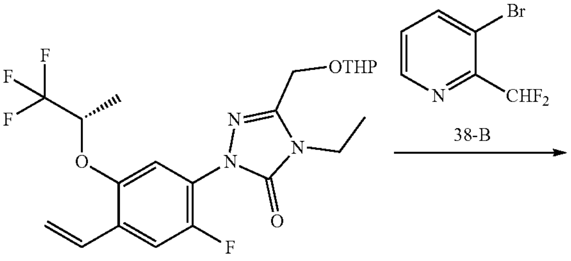

35-1

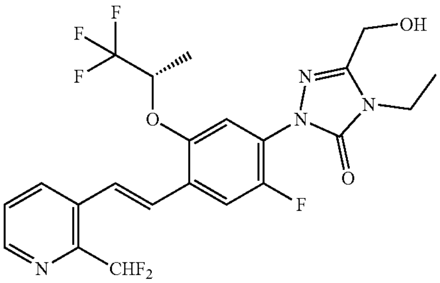

Compound 38

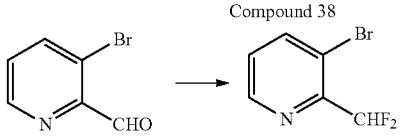

38-A 38-B

Step 1: Preparation of Compound 38-B

Compound 38-A (1.54 g, 8.26 mmol) was dissolved in dichloromethane (20 mL), and bis(2-methoxyethyl)aminosulfur trifluoride (2.66 g, 12.03 mmol, 2.64 mL) was added dropwise at 0° C., heated naturally to 15° C. and stirred for 2 hours. 20 mL of saturated sodium bicarbonate aqueous solution was added to the reaction solution, stood, and separated; the organic phase was dried over anhydrous sodium sulfate, filtered, and the filtrate was concentrated under reduced pressure. The crude product was separated and purified by silica gel column chromatography (gradient elution:petroleum ether:ethyl acetate=100:0 to 3:1) to obtain compound 38-B.

Step 2: Preparation of Compound 38

N-Methylpyrrolidone (0.5 mL), compound 35-1 (30 mg, 65.30 μmol) and compound 38-B (33.96 mg, 163.25 μmol) were added to a reaction flask and started to stirred; after nitrogen replacement, triethylamine (26.43 mg, 261.20 μmol, 36.35 μL, 4 eq) and bis(tri-t-butylphosphine)palladium(0) (3.34 mg, 6.53 μmol) were added, heated to 135° C. and stirred for 12 hours. After pouring the reaction into 10 mL of saturated ammonium chloride solution, ethyl acetate (10 mL×3) was added for extraction; the resulting organic phases were washed with saturated brine (10 mL×3), dried over anhydrous sodium sulfate, filtered, and the filtrate was subjected to rotary evaporation under reduced pressure at 45° C. The crude product was and purified by silica gel column chromatography separation (gradient elution:petroleum ether:ethyl acetate=100:0 to 30:70) to obtain the crude product. The crude product was dissolved in 0.4 mL of dichloromethane, and petroleum ether (0.9 mL) was added dropwise and stirred for 30 min, filtered, and the filter cake was washed with dichloromethane/petroleum ether (1/2, 0.5 mL×2), and then subjected to rotary evaporation under reduced pressure at 45° C. to obtain compound 38.

MS ESI calculated for $C_{22}H_{20}F_6N_4O_3$, $[M+H]^+$ 503.1, found 503.1.

$^1H$ NMR (400 MHz, $CD_3OD$) δ=8.55-8.54 (m, 1H), 8.23 (d, J=8.4 Hz, 1H), 7.73-7.69 (m, 1H), 7.63-7.59 (m, 2H), 7.43 (d, J=16.4 Hz, 1H), 7.36 (d, J=6.4 Hz, 1H), 6.96 (t, J=54.0 Hz, 1H), 5.09-5.03 (m, 1H), 4.60 (s, 2H), 3.94-3.89 (m, 2H), 1.55 (d, J=6.4 Hz, 3H), 1.39 (t, J=7.2 Hz, 3H).

Example 22: Synthesis of Compound 39

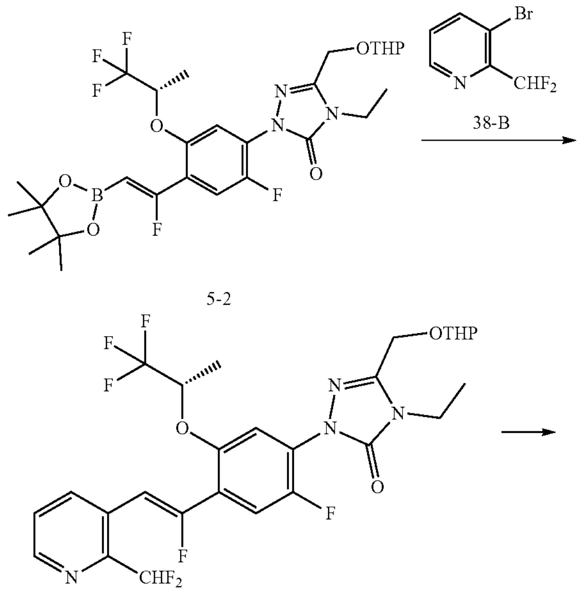

5-2

39-1

-continued

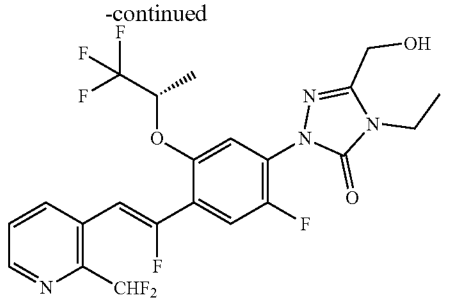

Compound 39

Step 1: Preparation of Compound 39-1

1,4-Dioxane (2 mL), water (0.4 mL), compound 5-2 (115 mg) and compound 38-B (23.79 mg, 114.35 μmol) were added to a reaction flask and started to stir; then anhydrous potassium phosphate (30.34 mg, 142.94 μmol) was added thereto, after nitrogen replacement, [1,1-bis(diphenylphosphino)ferrocene]dichloropalladium (4.18 mg, 5.72 μmol) was added thereto, heated to 90° C. and reacted for 0.5 hours. 5 mL of water and 5 mL of ethyl acetate were added to the reaction system and the solution was separated; the resulting organic phase was washed once with 5 mL of saturated brine, dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0 to 50:50) to obtain compound 39-1.

MS ESI calculated for $C_{27}H_{27}F_7N_4O_4$, $[M+H]^+$ 605.2, found 605.3.

$^1H$ NMR (400 MHz, $CDCl_3$) δ=8.53 (d, J=4.0 Hz, 1H), 8.31 (d, J=8.0 Hz, 1H), 7.54 (d, J=11.2 Hz, 1H), 7.47-7.44 (m, 1H), 7.36-7.25 (m, 2H), 6.75 (t, J=54.4 Hz, 1H), 4.90-4.82 (m, 1H), 4.77-4.71 (m, 2H), 4.51-4.46 (m, 1H), 3.93-3.85 (m, 3H), 3.63-3.60 (m, 1H), 1.87-1.76 (m, 2H), 1.66-1.54 (m, 7H), 1.42 (t, J=7.2 Hz, 3H).

Step 2: Preparation of Compound 39

Ethanol (0.5 mL) and compound 39-1 (20 mg, 33.08 μmol) were added to a reaction flask and started to stirred; then phosphoric acid (76.29 mg, 661.69 μmol, 45.41 μL, concentration of 85%) was added thereto, heated to 65° C. and reacted for 2 hours. After the reaction solution was cooled down to room temperature, the pH was adjusted to 7 by adding saturated sodium bicarbonate solution to the reaction system, and the reaction solution was subjected to rotary evaporation under reduced pressure at 45° C.; the resulting aqueous solution was extracted by adding 5 mL of ethyl acetate, and the organic phase was washed once with 5 mL of saturated brine, dried over anhydrous sodium sulfate, filtered, and the filtrate was subjected to rotary evaporation under reduced pressure at 45° C. The crude product was purified by silica gel column chromatography separation (gradient elution:petroleum ether:ethyl acetate=100:0 to 30:70) to obtain compound 39.

MS ESI calculated for $C_{22}H_{19}F_7N_4O_3$, $[M+H]^+$ 521.1, found 521.1.

$^1H$ NMR (400 MHz, $CD_3OD$) δ=8.53 (d, J=4.4 Hz, 1H), 8.36 (d, J=8.0 Hz, 1H), 7.63-7.58 (m, 2H), 7.51 (d, J=6.0 Hz, 1H), 7.29 (d, J=39.2 Hz, 1H), 6.83 (t, J=54.4 Hz, 1H), 5.28-5.22 (m, 1H), 4.60 (s, 2H), 3.94-3.89 (m, 2H), 1.59 (d, J=6.4 Hz, 3H), 1.39 (d, J=7.2 Hz, 3H).

Example 23: Synthesis of Compound 40

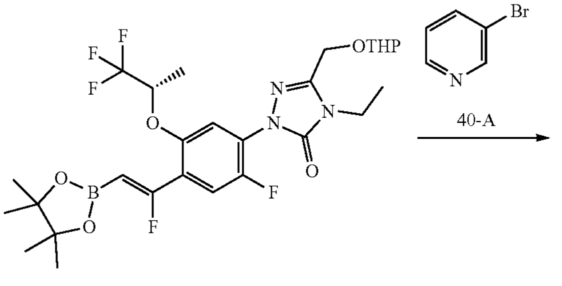

5-2

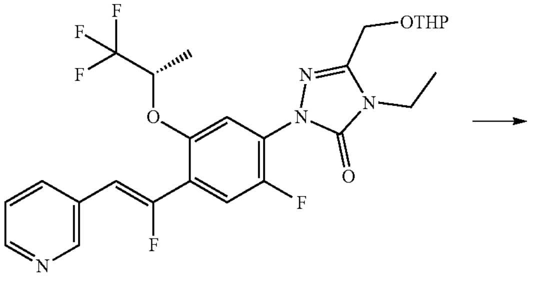

40-1

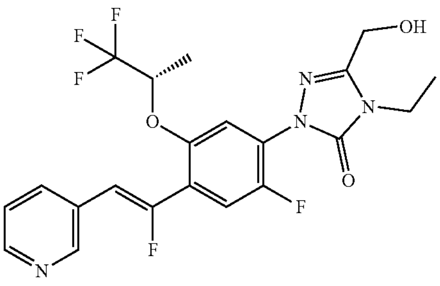

Compound 40

Step 1: Preparation of Compound 40-1

1,4-Dioxane (1 mL), water (0.2 mL), compound 5-2 (55 mg, 99 μmol) and compound 40-A (41 mg, 197 μmol) were added to a reaction flask and started to stir; then anhydrous potassium phosphate (52 mg, 247 μmol) and 1,1'-bis(diphenylphosphino)ferrocene-palladium(II)dichloride dichloromethane complex (16 mg, 19 μmol) were added thereto, heated to 90° C. and reacted for 1 hour. 5 mL of water and 5 mL of ethyl acetate were added to the reaction system and the solution was separated; the resulting organic phase was washed once with 5 mL saturated brine, dried over anhydrous sodium sulfate and filtered. The filtrate was subjected to rotary evaporation under reduced pressure at 45° C. The crude product was separated and purified by silica gel column chromatography (gradient elution:petroleum ether: ethyl acetate=100:0 to 40:60) to obtain compound 40-1.

MS ESI calculated for $C_{26}H_{27}F_5N_4O_4$, $[M+H]^+$ 555.2, found 555.2.

$^1$H NMR (400 MHz, $CD_3OD$) δ=8.75 (s, 1H), 8.51 (d, J=3.6 Hz, 1H), 8.03 (d, J=8.0 Hz, 1H), 7.55 (d, J=11.6 Hz, 1H), 7.35-7.30 (m, 2H), 6.89 (d, J=42.8 Hz, 1H), 4.84-4.68 (m, 3H), 4.49 (d, J=12.8 Hz, 1H), 3.95-3.85 (m, 2H), 3.71-3.60 (m, 2H), 1.87-1.76 (m, 2H), 1.66-1.59 (m, 7H), 1.42 (d, J=7.2 Hz, 3H).

Step 2: Preparation of Compound 40

Ethanol (1 mL) and compound 40-1 (20 mg, 36.07 μmol) were added to a reaction flask and started to stir; then phosphoric acid (83 mg, 721.36 μmol, 49.51 μL, content of 85%) was added thereto, heated to 65° C. and reacted for 2.5 hours. After the reaction solution was cooled down to room temperature, the pH was adjusted to 7 by adding saturated sodium bicarbonate solution to the reaction system, and the reaction solution was subjected to rotary evaporation under reduced pressure at 45° C.; the resulting aqueous solution was extracted by adding 5 mL of ethyl acetate, and the organic phase was washed once with 5 mL of saturated brine, dried over anhydrous sodium sulfate, filtered, and the filtrate was subjected to rotary evaporation under reduced pressure at 45° C. The resulting yellow oil was dissolved in 0.4 mL of dichloromethane, and petroleum ether (0.9 mL) was added dropwise under stirring and stirred for 30 min, filtered, and the filter cake was washed with dichloromethane/petroleum ether (1/2, 0.5 mL×2) and then subjected to rotary evaporation under reduced pressure at 45° C. to obtain compound 40.

MS ESI calculated for $C_{21}H_{19}F_5N_4O_3$, $[M+H]^+$ 471.1, found 471.1.

$^1$H NMR (400 MHz, $CD_3OD$) δ=8.69 (s, 1H), 8.45 (d, J=3.6 Hz, 1H), 8.13 (d, J=8.0 Hz, 1H), 7.62 (d, J=11.2 Hz, 1H), 7.51-7.47 (m, 2H), 6.92 (d, J=42.0 Hz, 1H), 5.25-5.18 (m, 1H), 4.60 (s, 2H), 3.95-3.89 (m, 2H), 1.59 (d, J=6.4 Hz, 3H), 1.39 (t, J=7.2 Hz, 3H).

Part of Biology

Experiment Example 1: Enzymology Experiment Data

The DHODH inhibitory activity of the compounds was detected by the following experimental method, and the experimental results are as shown in Table 1.

DHODH uses flavin mononucleotide FMN to catalyze the oxidation of dihydrooratic acid DHO to produce oratic acid, while the re-oxidation of FMN requires the participation of coenzyme CoQ. In the experiment of detecting the DHODH enzyme activity, CoQ was replaced by Resazurin dye as the final electron acceptor in the enzyme activity reaction. Resazurin solution is blue, and the resorufin generated after reduction has red fluorescence, and the fluorescence signal can be detected under the 535 nm of excitation wavelength and the 590 nm of emission wavelength. The components of the reaction buffer used in the experiment were 100 mM Hepes pH 7.0, 150 mM NaCl, 0.3% CHAPS, 0.5 mg/mL BSA, 0.1 μM FMN and 1% DMSO. The final concentration of DHODH enzyme in the reaction system was 5 nM, and the final concentration of substrate L-DHO was 15 μM, the final concentration of indicator Resazurin was 80 μM. The components of the reaction stop buffer were 100 mM Hepes pH 7.0 and 5 mM Orotate. The specific method was as follows: 2-fold final concentration of the DHODH enzyme solution was mixed with the compound, incubated at room temperature for 20 min, 2-fold final concentration of the substrate mixture solution of L-DHO and resazurin was added and reacted, incubated at room temperature away from light for 45 min. Then the reaction was stopped by adding 2-fold final concentration of the reaction stop buffer to the reaction system, and incubated at room temperature for 10 min, the fluorescence signal of the reaction system was detected with EnVision under the condition of Ex/Em=535/590 nm.

TABLE 1

| Inhibitory activity on DHODH enzyme in vitro test | |
|---|---|
| Test Compounds | Inhibitory Activity $IC_{50}$ (nM) |
| Compound 1 | 0.71 |
| Compound 2 | 3.9 |
| Compound 5 | 3.5 |
| Compound 6 | 12.4 |
| Compound 21 | 9 |
| Compound 22 | 121 |
| Compound 23 | 9 |
| Compound 24 | 8 |
| Compound 25 | 6 |
| Compound 26 | 1.5 |
| Compound 27 | 1.5 |
| Compound 28 | 2.4 |
| Compound 29 | 4.7 |
| Compound 30 | 8.0 |
| Compound 32 | 3.9 |
| Compound 35 | 2.6 |
| Compound 36 | 1.5 |
| Compound 37 | 31.8 |
| Compound 38 | 26.5 |
| Compound 39 | 1.3 |
| Compound 40 | 7.3 |

Conclusion: The compounds of the present disclosure have excellent DHODH enzyme inhibitory activity.

Experiment Example 2: Influenza Virus Cytopathic Effect (CPE) Experiment

The antiviral activity of the compounds against influenza virus (IFV) was evaluated by testing the median effective concentration ($EC_{50}$) values of the compounds. Cytopathic effect experiment was widely used to detect the protective effect of compounds on virus-infected cells to reflect the antiviral activity of compounds.

MDCK cells were seeded at a density of 2000 cells per well into a black 384-well cell culture plate and subsequently incubated overnight at 37° C. in a 5% $CO_2$ incubator. The compounds were diluted and added to the cell wells by Echo555 non-contact nano-upgrade acoustic liquid handler (triple multiple proportions dilution, 8 test concentration points). Influenza virus A/Weiss/43 (H1N1) strain was subsequently added to the cell culture wells at 1-2 90% tissue culture infective dose (TCID90) per well, and the final concentration of DMSO in the culture medium is 0.5%. Virus control wells (with DMSO and virus, without compound), cell control wells (with DMSO, without compound and virus) and culture medium control wells (with medium only, without cells) were set up. The cytotoxicity assay for the compounds was performed in parallel with the antiviral activity assay, and the experimental conditions were consistent with the antiviral activity detection except that no virus was added. Cell plate was incubated at 37° C. for 5 days in a 5% $CO_2$ incubator. Cell activity was tested after 5 days of incubation using the cell viability detection kit CCK8. Raw data were used to calculate the antiviral activity and cytotoxicity of the compounds.

The antiviral activity and cytotoxicity of the compound are expressed by the inhibition rate (%) of the compound on the cell-virus effect caused by the virus. The calculating formula is as follows:

$$\%\ \text{Inhibitory Activity} = \left(\frac{\text{Sample Value} - \text{Virus Control Average}}{\text{Cell Control Average} - \text{Virus Control Average}}\right) \times 100$$

The inhibition rate and cytotoxicity of the compounds were analyzed by nonlinear fitting using GraphPad Prism software to obtain the $EC_{50}$ values of the compounds. The experimental results are as shown in Table 2.

TABLE 2

| Test results of the compounds of the present disclosure on influenza virus A/Weiss/43 (H1N1) in vitro | |
|---|---|
| Test Compounds | $EC_{50}$ (nM) |
| Compound 1 | <1 |
| Compound 2 | 20 |
| Compound 5 | 70 |
| Compound 6 | 67 |
| Compound 26 | 2.4 |
| Compound 28 | 43 |
| Compound 35 | 42 |
| Compound 36 | 10 |
| Compound 39 | 42 |

Conclusion: The compounds of the present disclosure show positive effects in the experiment of inhibiting influenza virus replication at the cell level.

Experiment Example 3: Proliferation Inhibition Experiment of Peripheral Blood Mononuclear Cells Flow cytometry was used to detect cell proliferation of human peripheral blood mononuclear cells.

3.1 Reagent Preparation

Cell complete medium: 445 mL of RPMI1640 cell culture+50 mL of fetal bovine serum+5 mL of double antibody Buffer 1: 9.9 mL of phosphate buffer+0.1 mL of 10% bovine serum protein Buffer 2: 10 mL of fetal bovine serum+490 mL of phosphate buffer 3.2 Cell Thawing 3.2.1 20 mL of cell complete medium was added to a 50 mL of centrifuge tube and pre-heated in a 37° C. water bath for 5 minutes;

3.2.2 the cell cryotubes were removed from the liquid nitrogen storage tank and placed on dry ice for 5-10 minutes to allow the liquid nitrogen to evaporate fully;

3.2.3 the cell cryotubes were clamped with forceps and placed in the water bath, and shaken gently to thaw the frozen cells quickly;

3.2.4 the thawed cells were transferred to the pre-heated cell complete medium with a pipette, centrifuged at 350 g for 5 min, then the supernatant was discarded, and the cells was resuspended by adding 10 mL of phosphate buffer;

3.2.5 counting by cell counter, and cell viability and cell count were recorded.

3.3 Cell Labeling 3.3.1 Cell proliferation labeling solution (CellTrace™ Violet, 1:1000 dilution) was prepared 3.3.2 the above mixture was centrifuged at 350 g for 5 minutes, and the supernatant was discarded, then the cells ($20\times10^6$/mL) were resuspended by adding Buffer 1, and the resuspended cells were gently blown by pipette, and an equal volume of cell proliferation labeling solution (prepared in 3.3.1) was added, and gently blown well by pipette;

3.3.3 incubating in a 5% $CO_2$, 37° C. cell incubator for 18 minutes;

3.3.4 the 5-fold volume of cell complete medium was added and leaved at room temperature for 5 minutes to terminate the staining reaction;

3.3.5 the above mixture was centrifuged at 350 g for 5 minutes, and the supernatant was discarded, then the cells were resuspended by adding 10 mL of cell complete medium, counted by cell counter, and cell viability and cell count were recorded;

3.3.6 the above mixture was centrifuged at 350 g for 5 minutes, and the supernatant was discarded, then the corresponding volume of cell complete medium was added according to the cell counting results, and the density of the resuspended cells was $2\times10^6$/mL and was to be used.

3.4 Cell Proliferation Stimulation 3.4.1 50 μL/well prepared cell suspension ($1\times10^5$ cells/well), 50 μL of 4×PHA-M (the final concentration is 5 μg/mL), 50 μL of 4×test compound, 50 μL of cell complete medium were added to the wells of 96-well cell culture plate, and the corresponding control group was set up; (total volume of the reaction system is 200 μL)

3.4.2 the cell culture plate was placed and incubated in a 5% $CO_2$, 37° C. cell incubator for 48 hours.

3.5 Cell Proliferation Detection 3.5.1 the above mixture was centrifuged at 350 g for 5 minutes and the supernatant was transferred to a new cell culture plate and stored at −80° C.;

3.5.2 200 μL of Buffer 2 was add to the wells of the culture plate, and the above mixture was centrifuged at 350 g and the supernatant was discarded;

3.5.3 cell dead or living staining solution (7-AAD, 1:100 dilution) was prepared with Buffer 2;

3.5.4 100 μL/well of dead or living staining solution was added, and gently blown and mixed well by pipette, and stained at room temperature for 10 min;

3.5.5 cell proliferation was detected by flow cytometry analyzer and analyzed by Flowjo software.

TABLE 3

Inhibition effect of the compounds of the present disclosure on PBMC cell proliferation in vitro

| Test Compounds | $IC_{50}$ (nM) |
|---|---|
| Compound 5 | 0.8 |
| Compound 25 | 2 |
| Compound 26 | 4.6 |
| Compound 28 | 8.4 |
| Compound 36 | 5.9 |
| Compound 39 | 14.4 |

Conclusion: The compounds of the present disclosure can effectively inhibit the proliferation of activated PBMC and have excellent anti-inflammatory activity in vitro.

Experiment Example 4: Permeability Evaluation of the Compounds of the Present Disclosure 4.1. Cell Lines The MDR1-MDCK II cell line licensed from the laboratory of Piet Borst at the Netherlands Cancer Institute was used as an in vitro model for permeability evaluation experiments, and was seeded in Transwell-96-well cell plate at a density of $2.3\times10^5$ cells/$cm^2$ and cultured in a $CO_2$ incubator for 4-7 days before being used for transport experiments.

4.2. Experimental Conditions

Administration concentration of the test sample: 2.00 μM

Test direction and number of parallel samples: bidirectional A-B and B-A, 2 parallels Transport buffer (TB): HBSS solution (pH 7.40±0.05) containing 10 mM HEPES Incubation conditions: 37±1° C., 5% $CO_2$, 150 min incubation Control compounds: Nadolol and metoprolol were used as low and high permeability control compounds and digoxin was used as a substrate for P-glycoprotein. Administration concentration of nadolol and metoprolol were 2.00 μM, and administration concentration of digoxin was 10.0 μM.

4.3. Integrity Test of Monolayer Cell Membrane

After the transport experiments, the Lucifer Yellow Rejection Assay was used to test the integrity of the MDR1-MDCK II cell layer. The remaining solution in the apical and basolateral wells was removed, and 75 μL of TB containing 100 μM Lucifer Yellow was added to the apical wells and 250 μL of TB was added to the basolateral wells, respectively, and the cell plate was incubated in a cell incubator at 37±1° C., 5% $CO_2$ and saturated humidity for 30 min, then the 20 μL of sample was taken from the apical wells and mixed with 60 μL of TB, and 80 μL of sample was taken from the basolateral wells, and the relative fluorescence unit (RFU) was detected at 425/528 nm (excitation/emission) spectra using a microplate reader.

4.4. Sample Analysis

The sample analysis of the test samples and control compounds nadolol, metoprolol and digoxin in this experiment was carried out by the method of liquid chromatography-tandem mass spectrometry (LC-MS/MS). The retention times of analytes and internal standards, chromatogram acquisition and integration were processed using the software Analyst (Sciex, Framingham, MA, USA). The sample analysis was performed using semi-quantitative determination of peak areas of analytes and internal standards.

4.5. Data Analysis $$P_{app} = \frac{V_R}{\text{Area}\times\text{Time}} \times \frac{[\text{drug}]_{receiver}}{[\text{drug}]_{initial,donor}} = \frac{V_R}{\text{Area}\times\text{Time}} \times \frac{C_R}{C_0}$$

$$\text{Efflux Ratio} = \frac{P_{app}(B \text{ to } A)}{P_{app}(A \text{ to } B)}$$

$$\%\ \text{Solution Recovery} = \frac{C_R \times V_R + C_D \times V_D}{C_0 \times V_D} \times 100$$

$V_R$ is the volume of the solution at the receiving end (0.075 mL for side A and 0.25 mL for side B); Area is the relative surface area of the cell monolayer (0.0804 $cm^2$); Time is the incubation time (9000 s); $C_0$ is the peak area ratio of the compound at the administration end; $V_D$ is the volume at the administration end (0.075 mL for side A and 0.25 mL for side B); $C_D$ and $C_R$ are the peak area ratios of compounds at the administration side and the receiving side, respectively.

Lucifer yellow transmittance (% Lucifer Yellow) was calculated using the following equation:

$$\%\ \text{Lucifer Yellow} = \frac{V_{Basolateral} \times RFU_{Basolateral}}{V_{Apical} \times RFU_{Apical} + V_{Basolateral} \times RFU_{Basolateral}} \times 100$$

$RFU_{Apical}$ and $RFU_{Basolateral}$ are the relative fluorescence intensities of Lucifer yellow at the apical end and basolateral end, respectively. $V_{Apical}$ and $V_{Basolateral}$ are the sample loading volumes at the apical end and basolateral end, respectively (0.0750 and 0.250 mL, respectively).

4.6. Test Results of the Compounds of the Present Disclosure

The results of the permeability test of the compounds of the present disclosure on the MDR1-MDCK II cell line are shown in Table 4.

TABLE 4

Summary of permeability evaluation of the compounds of the present disclosure

| Compounds | Permeability $P_{app}$ ($10^{-6}$ cm/s) A to B | B to A | Efflux ratio | Permeability conclusion |
|---|---|---|---|---|
| Compound 5 | 13.29 | 18.19 | 1.37 | High permeability |
| Compound 6 | 3.72 | 3.55 | 0.95 | Medium permeability |
| Compound 26 | 8.59 | 7.76 | 0.90 | High permeability |
| Compound 28 | 8.65 | 10.73 | 1.24 | High permeability |
| Compound 39 | 10.14 | 13.91 | 1.37 | High permeability |

Note:
low permeability: $P_{app} \leq 1.0$ ($\times 10^{-6}$ cm/s); medium permeability $1.0 < P_{app} < 5.5$ ($\times 10^{-6}$ cm/s); high permeability: $P_{app} \geq 5.5$ ($\times 10^{-6}$ cm/s).

Conclusion: The compounds of the present disclosure have excellent membrane permeability in the study of cell membrane permeability.

Experiment Example 5: Pharmacokinetic Evaluation of the Compounds of the Present Disclosure Experiment process: 0.04 mg/mL of a clarified solution of the test compound in 5% DMSO/10% Solutol solution/85% water was injected into female Balb/c mice (overnight fasting, 7-9 weeks of age) via tail vein, with dosage of 0.2 mg/kg. 0.1 mg/mL of the test compound in 5% DMSO/10% Solutol solution/0.2% Tween80/84.8% water was administered by gavage to female Balb/c mice (overnight fasting, 7-9 weeks of age), with dosage of 1 mg/kg. About 30 μL of blood was collected from the jugular vein at 0.0833, 0.25, 0.5, 1.0, 2.0, 4.0, 8.0, 10 and 24 h and from the tail vein at 0.25, 0.5, 1.0, 2.0, 4.0, 8.0 and 24 h after administration for both groups of animals, and were placed in anticoagulation tubes with EDTA-K2, and the blood was separated by centrifugation to obtain plasma. Plasma concentrations were detected by LC-MS/MS, and relevant pharmacokinetic parameters were calculated using WinNonlin™ Version 6.3 (Pharsight, Mountain View, CA) pharmacokinetic software with a non-compartmental model linear logarithmic trapezoid method.

Experimental Data Analysis.

TABLE 5

Summary of pharmacokinetic data

| PK parameters | Compound 5 IV | Compound 5 PO | Compound 6 IV | Compound 6 PO | Compound 26 IV | Compound 26 PO | Compound 39 IV | Compound 39 PO |
|---|---|---|---|---|---|---|---|---|
| $C_0$ (nM) | 354 | — | 640 | — | 451 | — | 419 | — |
| $C_{max}$ (nM) | — | 794 | — | 935 | — | 872 | — | 787 |
| $T_{max}$ (h) | — | 2.00 | — | 2.00 | — | 1.00 | — | 1.50 |
| $T_{1/2}$ (h) | 5.83 | 5.36 | 6.83 | 9.19 | 9.68 | 14.8 | 10.4 | 8.86 |
| $Vd_{SS}$ (L/kg) | 2.02 | — | 1.53 | — | 1.93 | — | 2.31 | — |
| Cl (mL/min/kg) | 4.38 | — | 3.14 | — | 2.32 | — | 2.86 | — |
| $T_{last}$ (h) | 24.0 | 24.0 | 24.0 | 24.0 | 24 | 24.%0 | 24.0 | 24.0 |
| $AUC_{0\text{-}last}$ (nM · h) | 1425 | 6867 | 1961 | 7786 | 2295 | 9204 | 1837 | 8950 |
| $AUC_{0\text{-}inf}$ (nM · h) | 1507 | 7215 | 2128 | 9084 | 2858 | 13044 | 2243 | 10610 |
| $MRT_{0\text{-}last}$ (h) | 6.24 | 6.99 | 5.93 | 7.76 | 8.04 | 8.90 | 7.83 | 8.67 |
| F (%) | — | 95.8% | — | 85.4% | — | 80.2% | — | 97.4% |

Note:
— indicates not tested.

Conclusion: The compounds of the present disclosure have excellent metabolic stability in vivo (Cl), show long half-lives ($T_{1/2}$) for both IV and PO, have good drug exposure (AUC), and very high oral absorption bioavailability. The compounds of the present disclosure have excellent pharmacokinetic properties.

Experimental Example 6: Pharmacodynamic Evaluation In Vivo of the Compounds of the Present Disclosure 6.1 Purpose of the study: In order to verify the effect of the test sample on dextran sulfate sodium (DSS) induced colitis model in C57B3L/6 mice.

6.2 Experimental design for inducing colitis: The mice in the vehicle and administration groups were administered on Day 0 for 1 h, and the mice freely drank water containing 3% DSS until Day 7, after Day 8, the mice were euthanized and their colon was taken for analysis. C57BL/6 mice, 8 weeks of age, 18-20 g, female. Administration was started on Day 0 to Day 7 for both the vehicle and administration groups.

6.3 Drinking water containing DSS: The appropriate amount of DSS powder was dissolved in autoclaved drinking water and configured as a 3% DSS solution.

6.4 Administration: Animals of group 1 were given the vehicle, animals of group 2 were given compound 5, and animals of group 3 were given normal drinking water and the vehicle, the vehicle was 5% DMSO/10% Solutol solution/0.2% Tween80/84.8% aqueous solution, with twice a day.

6.5 Measurement 6.5.1 Weight

Recording frequency was once a day, Days 0 to 8.

6.5.2 Disease Activity Index (DAI)

The recording frequency is once a day, Days 0 to 8, and is rated at 4 grades according to the following criteria:

Weight change (0, ≤1%; 1, 1-5%; 2, 6-10%; 3, 11-20%; 4, >20%).

Hematochezia (0, negative; 1, weakly positive for occult blood; 2, positive for occult blood; 3, significant hematochezia; 4, massive hematochezia)

Stool score (0, normal; 1, soft stool; 2, flaccid stool; 3, loose stool; 4, diarrhea)

The daily disease index is obtained by adding the scores of the above three parts.

6.5.3 Colonic Collection

On Day 8, all animals received an overdose of $CO_2$ and were executed by cervical dislocation. The abdominal cavity was cut open and the colon of the mice was taken, the tissue around the colon was removed, and the longitudinal length from the ileocecum to the anus was measured and the whole was photographed. The colon was dissected, the intestinal contents were cleaned, weighed separately, and the stool consistency was recorded.

6.5.4 Sample Treatment

The colonic tissue was divided into two longitudinally and one was fixed in 10% neutral paraformaldehyde in the form of "Swiss" rolls.

The other was quickly frozen in liquid nitrogen and then stored in a refrigerator at −80° C. for detection and analysis to be selected.

6.6 Statistical Analysis

The experimental data were expressed as mean±standard error (S.E.M.). Data were adopted by GraphPad Prism and analyzed by ANOVA statistical method. $P<0.05$ was considered as statistical difference.

6.7 Experimental Results 6.7.1 Animal Weight Results

Figure 21:
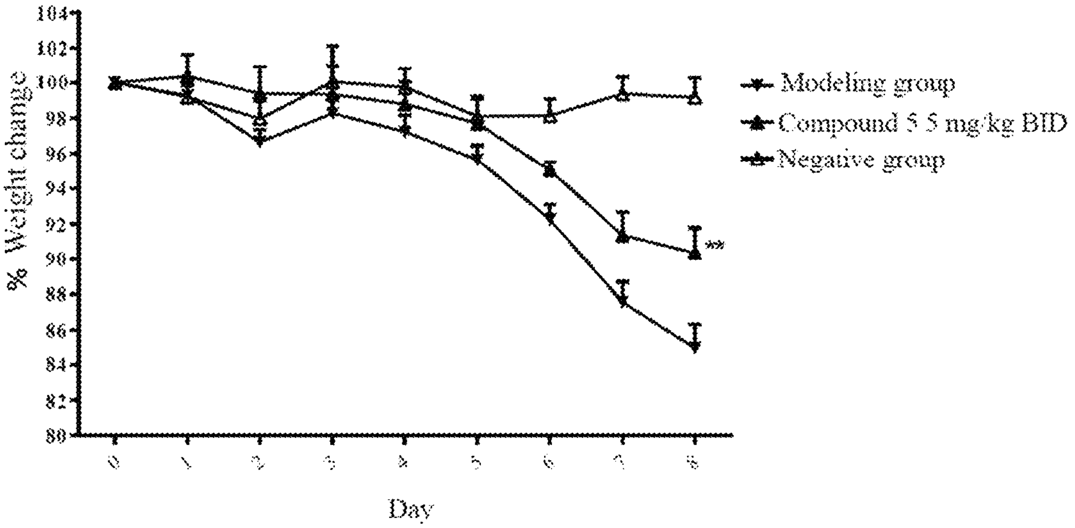
FIG. 21 is the curve of animal weight change with administration time during administration.

From Days 0 to 8, the animals were weighed once a day and the changes in weight are as shown in FIG. 21. Compared with the modeling group, compound 5 can significantly slow down the weight loss of mice, and has a statistically significant difference ($p<0.01$) on Day 8, which has a significant protective effect on weight of mice.

6.7.2 Daily Disease Index (DAI)

Figure 22:
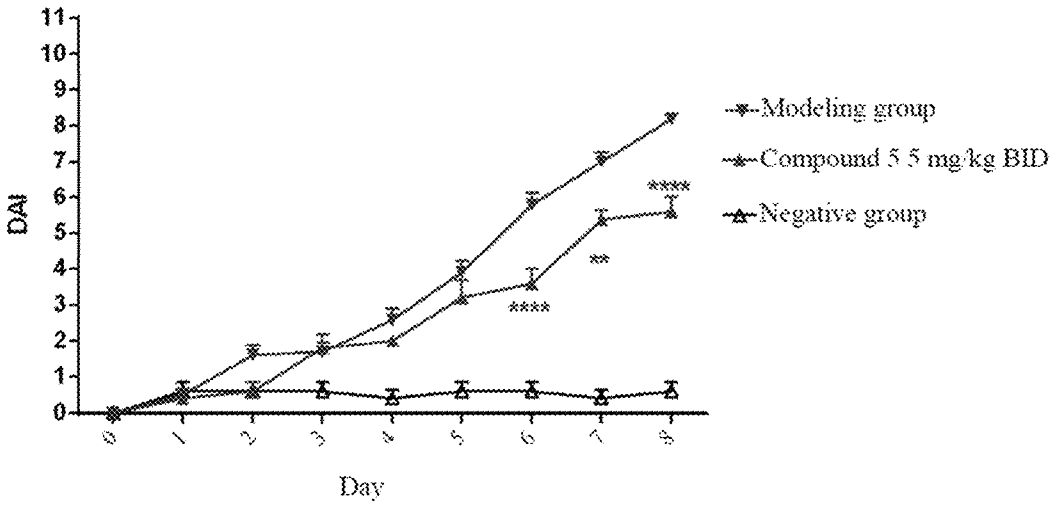
FIG. 22 is DAI (Disease Activity Index) evaluation, *$p<0.05$ $p<0.01$ *$p<0.005$ ****$p<0.0001$, compared with the modeling group, ANOVA.

From Days 0 to 8, the weight, hematochezia and stool scores were combined, and the evaluation results of DAI (Daily disease index) are as shown in FIG. 22. Compared to the modeling group, the disease score of mice is significantly improved by administrating compound 5 for 6 days, and the effect of reducing DAI score on Day 8 shows a high significant difference compared to the modeling group, $p<0.0001$.

6.7.3 Analysis Results of Colonic Density and Length

Figure 23:
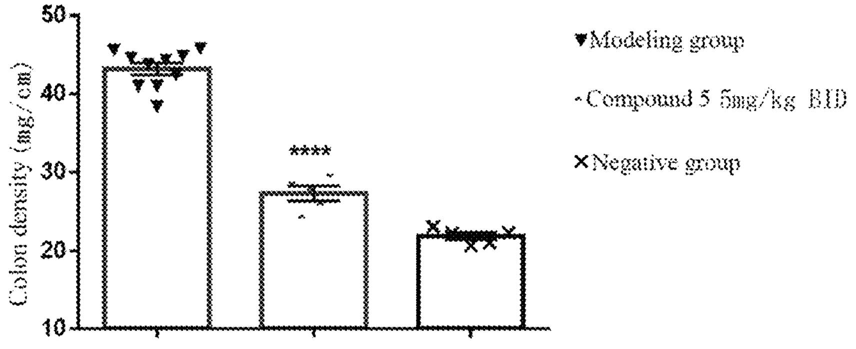
FIG. 23 is the colon density at the end of the experiment; *$p<0.05$ $p<0.01$ *$p<0.005$ ****$p<0.0001$, compared with the modeling group, ANOVA.
Figure 24:
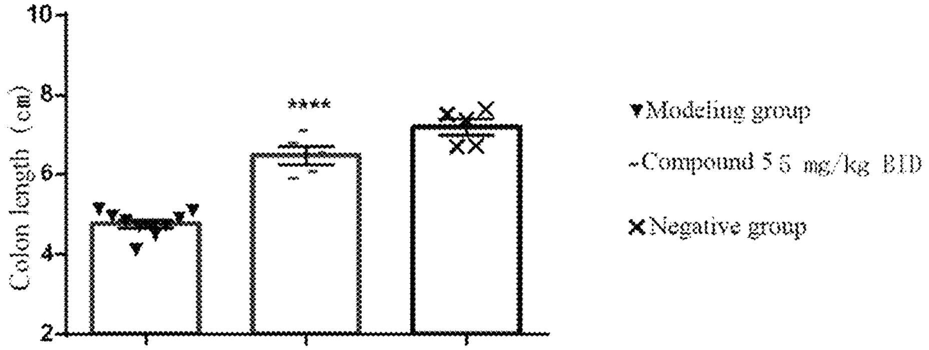
FIG. 24 is the colon length at the end of the experiment: *$p<0.05$ $p<0.01$ *$p<0.005$ ****$p<0.0001$, compared with the modeling group, ANOVA.

Compared with the modeling group, compound 5 at a dose of 5 mpk/BID significantly improves the inflammation-induced increase of colonic density as well as the tendency of colonic shortening at the experimental endpoint, and has a significant difference, $p<0.0001$, as shown in FIG. 23 and FIG. 24.

6.7.4 PD Study and Analysis Results of Colonic Mucosal Inflammatory Factor

Figure 25:
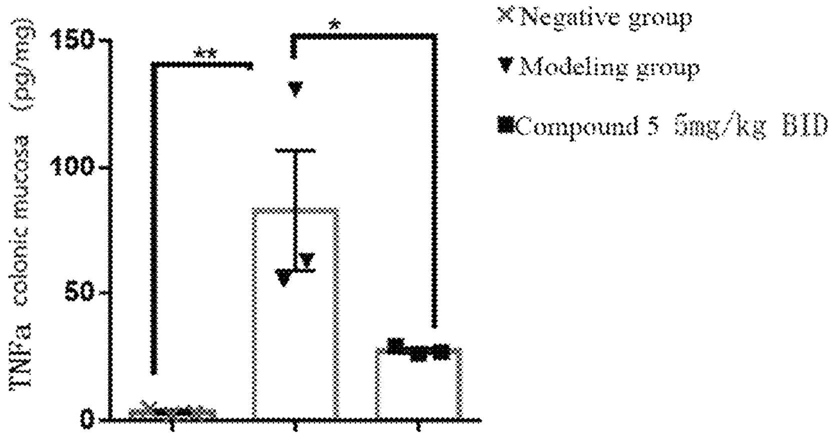
FIG. 25 is the cytokines of colonic mucosa at the end of the experiment; *$p<0.05$ $p<0.01$ *$p<0.005$ ****$p<0.0001$, compared with the modeling group, ANOVA.

On Day 8 of the experiment, colonic mucosal tissues were taken and tested for inflammatory factor TNF-α, and the results are as shown in FIG. 25. Compound 5 at a dose of 5 mg/kg BID, effectively reduces the level of inflammatory factor TNF-α in the colonic mucosa of mice, and has a significant difference $p<0.05$ compared with the modeling group.

To sum up, compound 5 shows significant anti-inflammatory effects on the DSS-induced colitis (IBD) model in mice, which can significantly slow down the weight loss of mice with enteritis and improve the disease health status and score associated with diarrhea and hematochezia; and can also improve the inflammation-induced increase of colonic density as well as the tendency of colonic shortening, which is consistent with the DAI score results; while PD study shows that compound 5 can also significantly reduce the levels of the inflammatory cytokine TNF-α in the colonic mucosa.

Experiment Example 7: Enzyme Selectivity In Vitro of the Compounds of the Present Disclosure 7.1 Experimental Process This experiment aims to study the activity and selectivity of the compounds towards kinases selected from the Eurofins KinaseProfiler™ platform. The compounds against each selected kinase were tested using the KinaseProfiler™ experimental procedure of Eurofins standard, which follows the relevant standard operating procedures. Protein kinases (except ATM(h) and DNA-PK(h)) were tested by radiation dose, while lipid kinases, ATM(h), ATR/ATRIP(h) and DNA-PK(h) were tested by HRTF®.

Compound powders were prepared into 10 mM mother liquor through 100% DMSO solution and then diluted to 50× liquid.

An appropriate amount of 50× storage solution of the test compound was taken into the test wells, and then the kinase and substrate were added and mixed well. A certain concentration of ATP was added to start the reaction. The kinase and substrate did not need to be pre-incubated with the compound before adding ATP.

7.2 Data Analysis

Data were processed using custom in-house analysis software. The results showed the percentage of remaining enzyme activity to the enzyme activity of the DMSO control group, which can be calculated by the following equation:

(mean of sample group−mean of blank group)/mean of control group 7.3 Summary of Experimental Results The kinase off-target study in vitro of compound 5 of the present disclosure was carried out to evaluate the inhibitory activity against 15 common kinases at a concentration of 1 μM of the drug, and the results are as shown in Table 6.

TABLE 6

Experimental studies on the selectivity of compounds for common kinases

| Kinases | ATP concentration (μM) | Residual enzyme activity for compound 5 at 1 μM (%) |
|---|---|---|
| Abl(h) | 45 | 88 |
| ALK(h) | 200 | 94 |
| CDK1/cyclinB(h) | 45 | 91 |
| CDK2/cyclinA(h) | 45 | 72 |
| CDK9/cyclin T1(h) | 45 | 95 |
| Flt3(h) | 200 | 84 |
| Fyn(h) | 70 | 121 |
| GSK3β(h) | 15 | 126 |
| JAK2(h) | 45 | 81 |

TABLE 6-continued

Experimental studies on the selectivity of compounds for common kinases

| Kinases | ATP concentration (μM) | Residual enzyme activity for compound 5 at 1 μM (%) |
|---|---|---|
| KDR(h) | 90 | 90 |
| LOK(h) | 120 | 108 |
| MLK1(h) | 45 | 111 |
| MST1(h) | 90 | 96 |
| Rsk1(h) | 45 | 88 |
| TNIK(h) | 70 | 84 |

Conclusion: The compound of the present disclosure has weak inhibition or no inhibition on 15 common kinases, has excellent DHODH target selectivity, and can avoid side effects caused by off-target.

What is claimed is:

1. A compound represented by formula (V) or a pharmaceutically acceptable salt thereof,

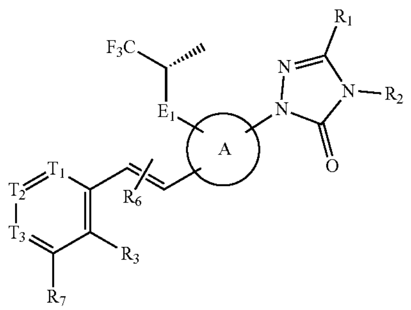

(V)

wherein, ring A is selected from phenyl, pyridinyl, pyrrolyl, pyrazolyl, imidazolyl and 1,2,4-triazolyl, and the phenyl, pyridinyl, pyrrolyl, pyrazolyl and imidazolyl are optionally substituted by 1, 2 or 3 $R_a$;

$E_1$ is selected from $CH_2$ and O;

$T_1$ is selected from $CR_4$ and N;

$T_2$ is selected from CH and N;

$T_3$ is selected from $C_R$ and N;

$R_1$ is selected from $CH_2OH$, COOH and $CONH_2$;

$R_2$ is selected from $C_{1-3}$ alkyl, and the $C_{1-3}$ alkyl is optionally substituted by 1, 2 or 3 $R_b$;

$R_3$ and $R_4$ are each independently selected from H, F, Cl, CN, $CH_3$ and $OCH_3$, and the $CH_3$ and $OCH_3$ are optionally substituted by 1, 2 or 3 $R_c$;

$R_5$ is selected from H, F, Cl and CN;

$R_6$ is selected from H and F;

$R_7$ is selected from H and

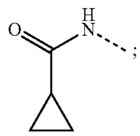

;

each $R_a$ is independently selected from F and Cl;

each $R_b$ is independently selected from F, Cl and Br;

each $R_c$ is independently selected from F, Cl and Br.

2. The compound or the pharmaceutically acceptable salt thereof according to claim 1, wherein, $R_2$ is selected from $CH_3$ and $CH_2CH_3$.

3. The compound or the pharmaceutically acceptable salt thereof according to claim 1, wherein, the ring A is selected from

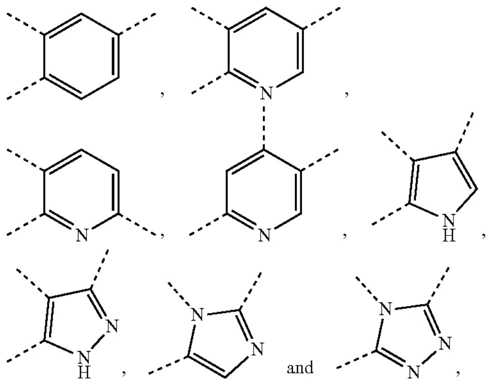

and the

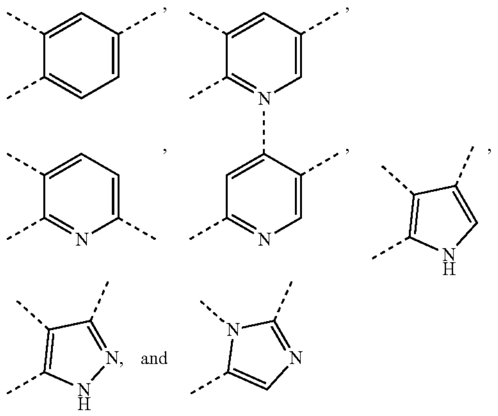

are optionally substituted by 1, 2 or 3 $R_a$.

4. The compound or the pharmaceutically acceptable salt thereof according to claim 3, wherein, the ring A is selected from

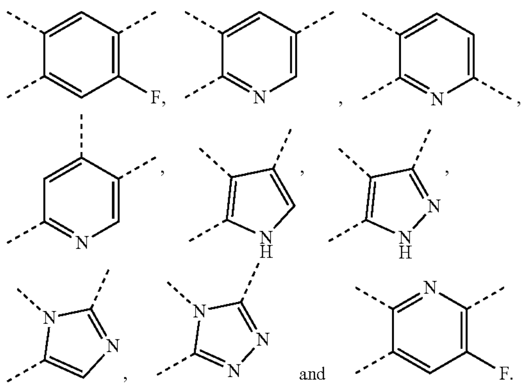

5. The compound or the pharmaceutically acceptable salt thereof according to claim 1, wherein, the structural moiety

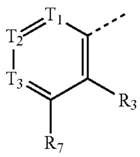

is selected from

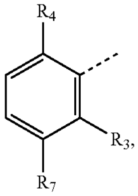
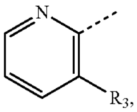
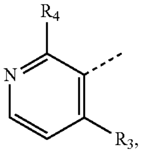
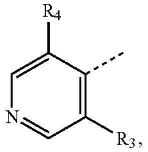
and
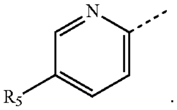
.

6. The compound or the pharmaceutically acceptable salt thereof according to claim 1, wherein, the structural moiety

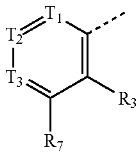

is selected from

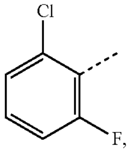
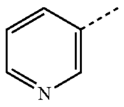
,
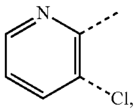
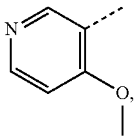
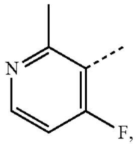
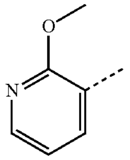
,
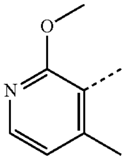
,
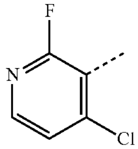
, -continued

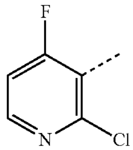
,
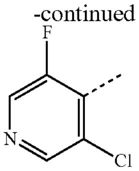
,
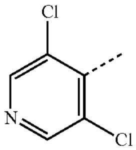
,
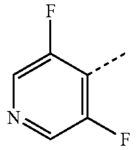
,
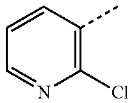
,
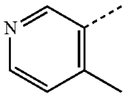
,
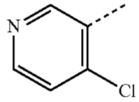
,
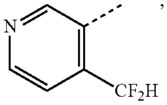
,
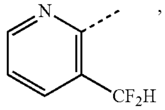
,
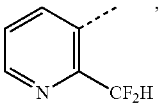
,
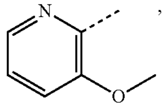
,
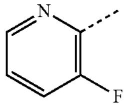
,
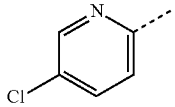
,
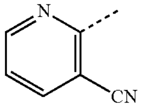
and
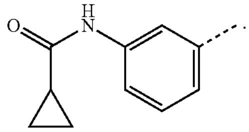
.

7. The compound or the pharmaceutically acceptable salt thereof according to claim 1, wherein the compound is selected from, (I-1)

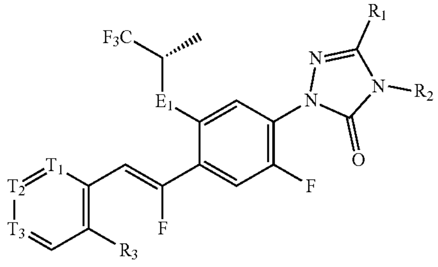

(I-3)

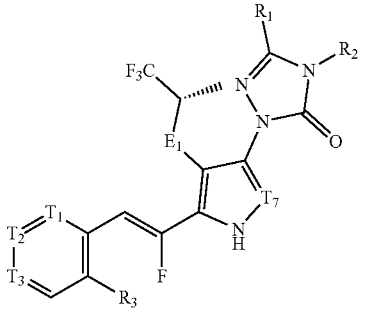

and

-continued
(IV-1)
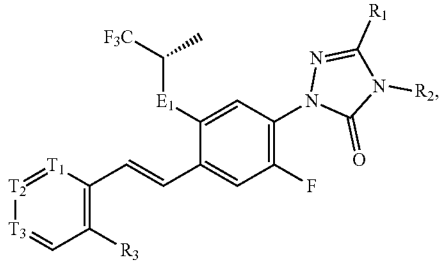
wherein,
$T_7$ is selected from CH and N.
8. A compound represented by the following formula or a pharmaceutically acceptable salt thereof, selected from:
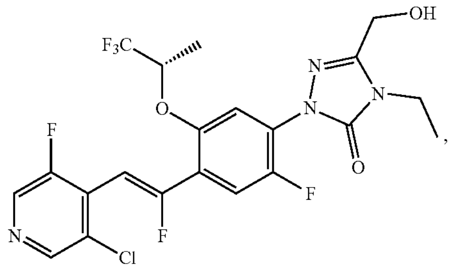
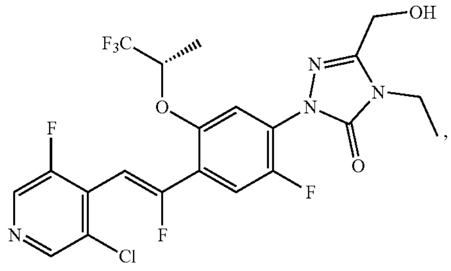
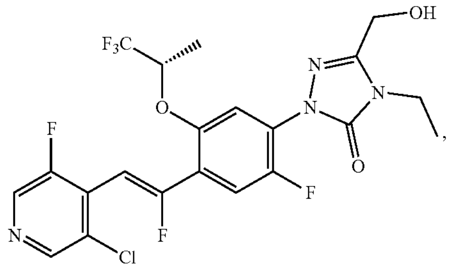
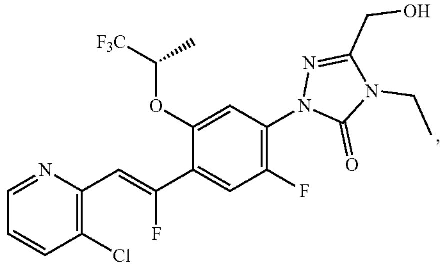
-continued
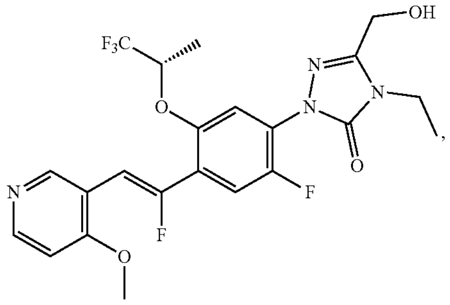
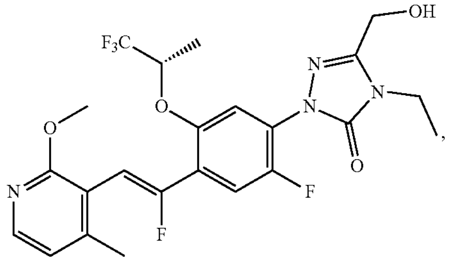
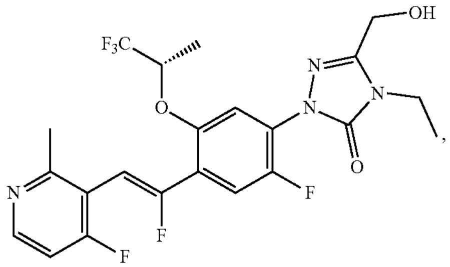
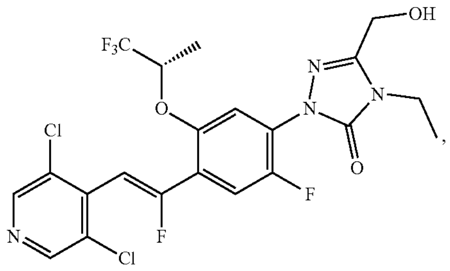
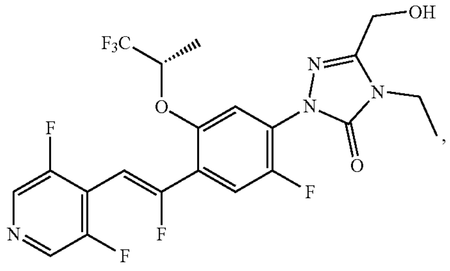
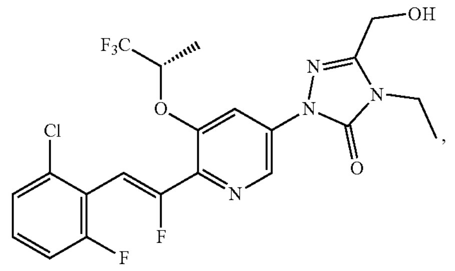

-continued
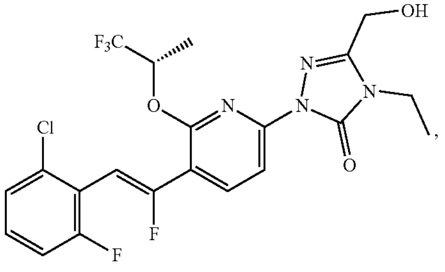
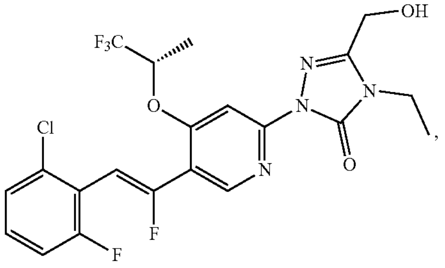
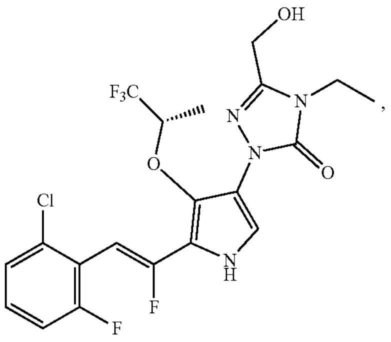
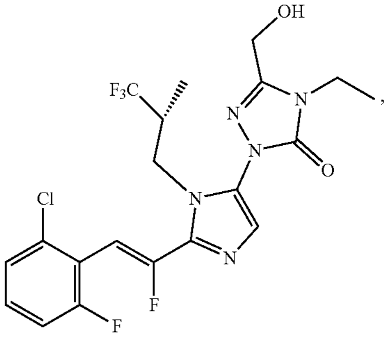
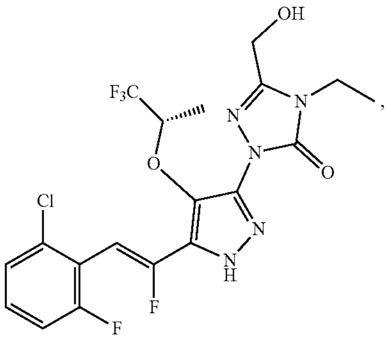
-continued
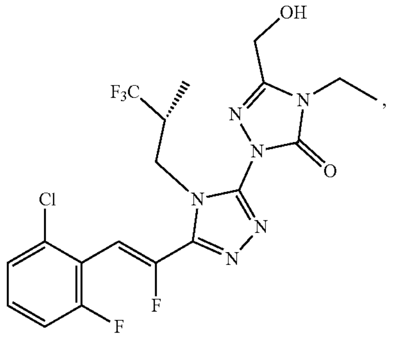
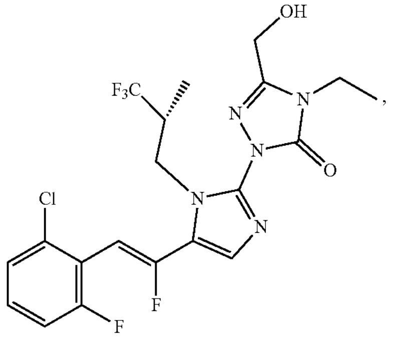
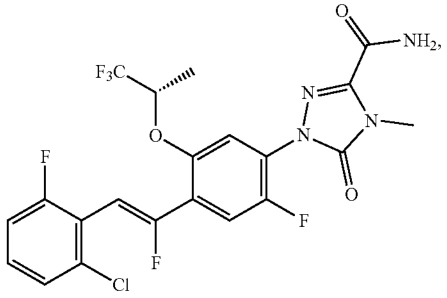
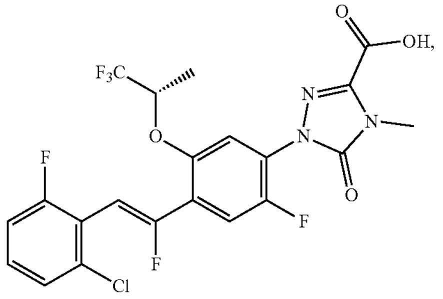
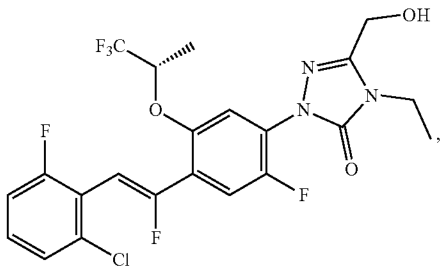

-continued
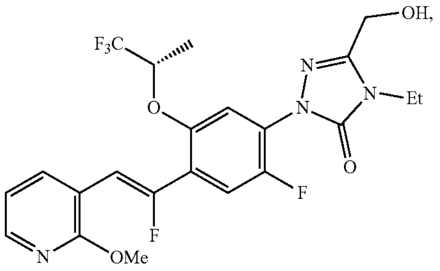
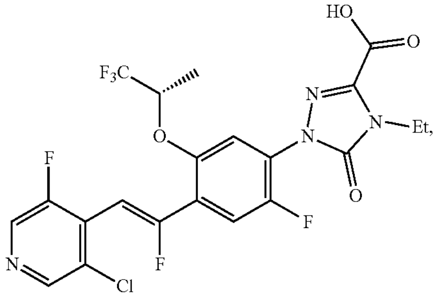
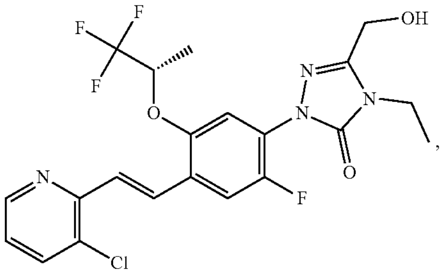
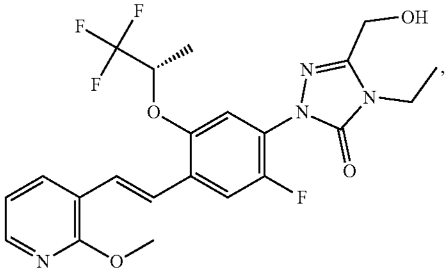
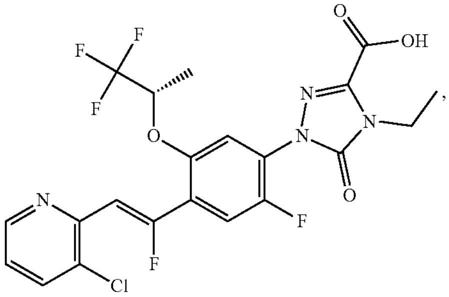
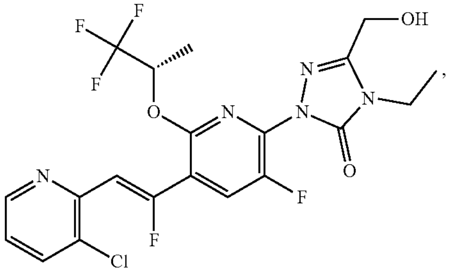
-continued
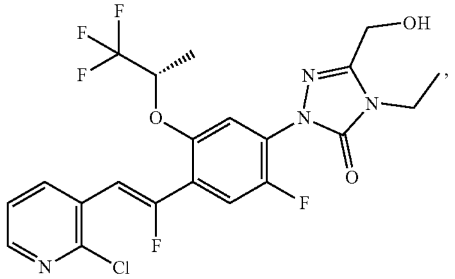
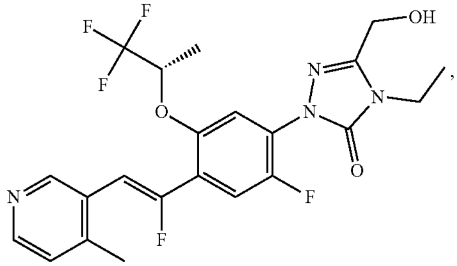
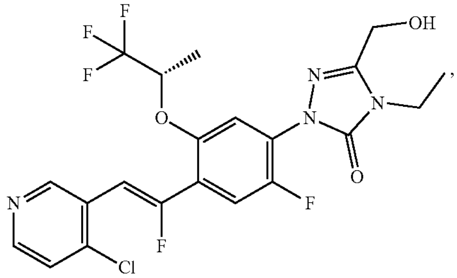
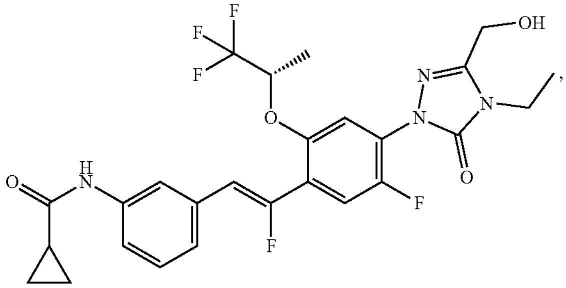
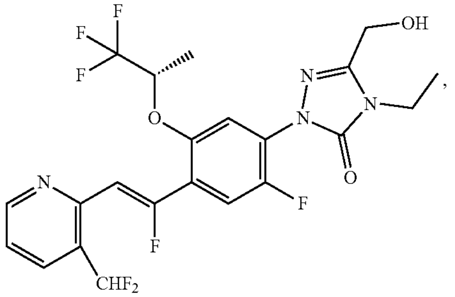
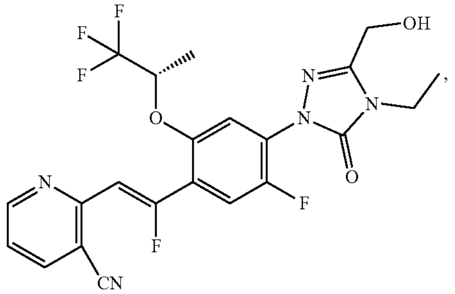

-continued

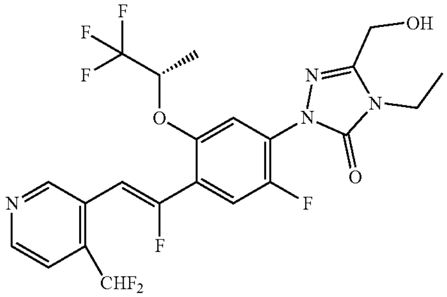
,
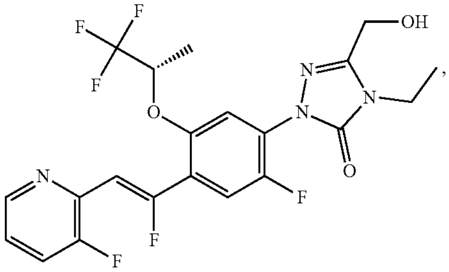
,
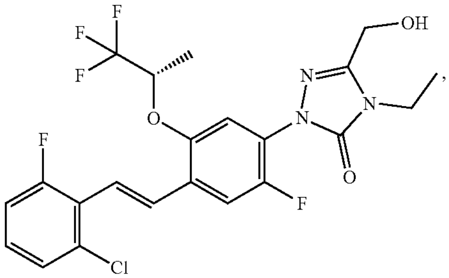
,
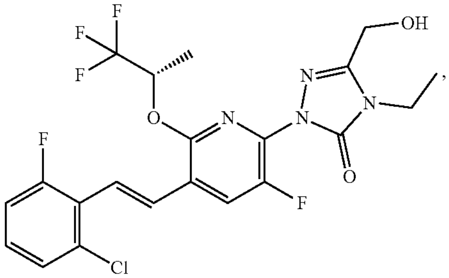
,
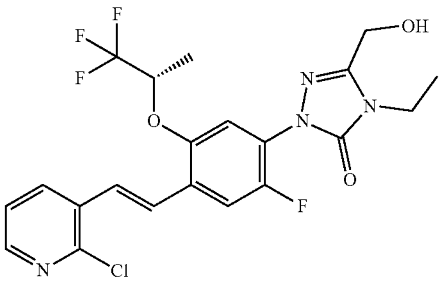
,
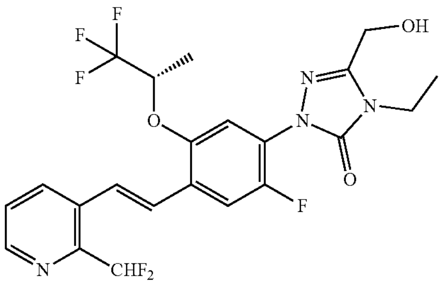
, -continued

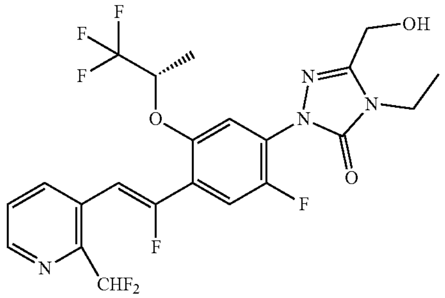
and
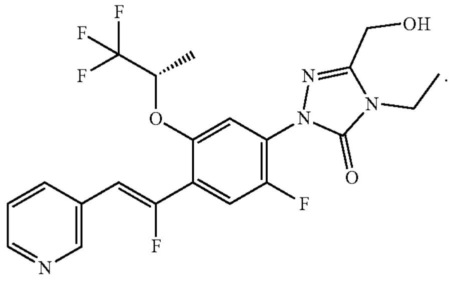
.

9. A method for treating diseases related to DHODH in a subject in need thereof, comprising: administering an effective amount of the compound or the pharmaceutically acceptable salt thereof according to claim 1 to the subject.

10. A method for treating diseases related to DHODH in a subject in need thereof, comprising: administering an effective amount of the compound or the pharmaceutically acceptable salt thereof according to claim 8 to the subject.

11. The compound or the pharmaceutically acceptable salt thereof according to claim 5, wherein, the structural moiety

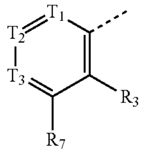

is selected from

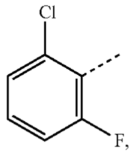
,
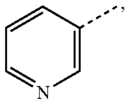
,
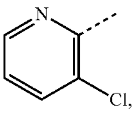
,
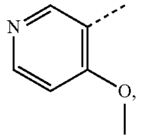
,
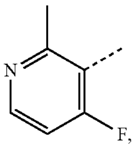
,

-continued
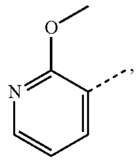
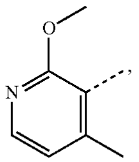
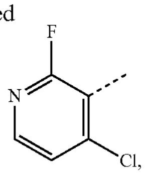
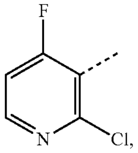
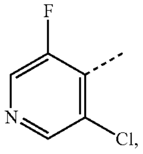
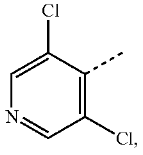
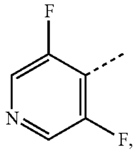
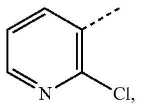
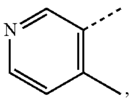
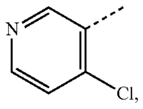
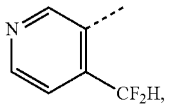
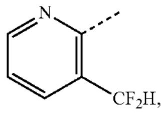
-continued
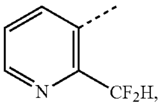
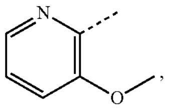
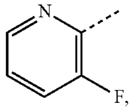
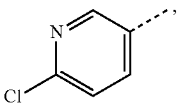
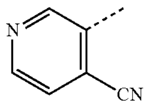
and
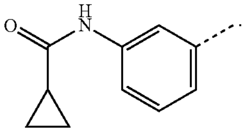
* * * * *